US012161901B2

(12) United States Patent
Dale et al.

(10) Patent No.: US 12,161,901 B2
(45) Date of Patent: Dec. 10, 2024

(54) NON-TOXIC FIRE EXTINGUISHING COMPOSITIONS, DEVICES AND METHODS OF USING SAME

(71) Applicant: Neozyme International, Inc., Costa Mesa, CA (US)

(72) Inventors: Parker David Dale, Newport Beach, CA (US); Jay Johnston, Pottsville, PA (US)

(*) Notice: Subject to any disclaimer, the term of this patent is extended or adjusted under 35 U.S.C. 154(b) by 678 days.

(21) Appl. No.: 17/240,925

(22) Filed: Apr. 26, 2021

(65) Prior Publication Data

US 2021/0331017 A1 Oct. 28, 2021

Related U.S. Application Data

(60) Provisional application No. 63/015,640, filed on Apr. 26, 2020.

(51) Int. Cl.
| | | |
|---|---|---|
| *A62D 1/00* | (2006.01) | |
| *A62D 1/02* | (2006.01) | |
| *C09K 21/00* | (2006.01) | |
| *C09K 21/06* | (2006.01) | |
| *C12P 1/02* | (2006.01) | |

(52) U.S. Cl.
CPC ........... *A62D 1/005* (2013.01); *A62D 1/0014* (2013.01); *A62D 1/0042* (2013.01); *A62D 1/0064* (2013.01); *A62D 1/0078* (2013.01); *C09K 21/00* (2013.01); *C09K 21/06* (2013.01); *C12P 1/02* (2013.01)

(58) Field of Classification Search
CPC .... A62D 1/005; A62D 1/0014; A62D 1/0042; A62D 1/0064; A62D 1/0078; C12P 1/02; C09K 21/00; C09K 21/06
See application file for complete search history.

(56) References Cited

U.S. PATENT DOCUMENTS

| | | | |
|---|---|---|---|
| 3,635,797 A | 1/1972 | Battistoni et al. | |
| 4,052,858 A | 10/1977 | Jeppson | |
| 4,459,213 A * | 7/1984 | Uchida ................ | A62D 1/0078 252/2 |
| 4,541,986 A | 9/1985 | Schwab et al. | |
| 4,666,606 A | 5/1987 | Heinicke | |
| 4,758,353 A | 7/1988 | Spence et al. | |
| 4,804,478 A | 2/1989 | Tamir | |
| 5,071,765 A | 12/1991 | Wiatr | |
| 5,075,008 A | 12/1991 | Chigusa et al. | |
| 5,139,945 A | 8/1992 | Liu | |
| 5,179,003 A | 1/1993 | Wolf et al. | |
| 5,227,067 A | 7/1993 | Runyon | |
| 5,284,844 A | 2/1994 | Lorenz et al. | |
| 5,308,449 A | 5/1994 | Fuentes et al. | |
| 5,326,477 A | 7/1994 | Fuqua et al. | |
| 5,369,031 A | 11/1994 | Middleditch et al. | |
| 5,407,577 A | 4/1995 | Nghiem | |
| 5,462,868 A | 10/1995 | Britt et al. | |
| 5,500,306 A | 3/1996 | Hsu et al. | |
| 5,616,479 A | 4/1997 | Marchal et al. | |
| 5,654,192 A | 8/1997 | Ducreux et al. | |
| 5,736,209 A | 4/1998 | Andersen et al. | |
| 5,807,464 A | 9/1998 | Jobbins et al. | |
| 5,820,758 A | 10/1998 | Dale et al. | |
| 5,849,566 A | 12/1998 | Dale et al. | |
| 5,866,376 A | 2/1999 | Rocha et al. | |
| 5,879,913 A | 3/1999 | Marchal et al. | |
| 5,879,928 A | 3/1999 | Dale et al. | |
| 5,885,590 A | 3/1999 | Hunter et al. | |
| 5,885,950 A | 3/1999 | Dale et al. | |
| 5,942,552 A * | 8/1999 | Cox .................... | A62D 3/02 521/65 |
| 6,001,218 A | 12/1999 | Hsu et al. | |
| 6,699,391 B2 | 3/2004 | Baldridge et al. | |
| 6,783,679 B1 | 8/2004 | Rozich | |
| 6,841,572 B2 | 1/2005 | Horst et al. | |
| 6,884,351 B1 | 4/2005 | Lytal | |
| 7,165,561 B2 | 1/2007 | Baldridge et al. | |
| 7,476,529 B2 | 1/2009 | Podella et al. | |
| 7,645,730 B2 | 1/2010 | Baldridge et al. | |
| 7,658,848 B2 | 2/2010 | Baldridge et al. | |
| 7,659,237 B2 | 2/2010 | Baldridge et al. | |
| 7,759,301 B2 | 7/2010 | Baldridge et al. | |
| 7,922,906 B2 | 4/2011 | Baldridge et al. | |
| 8,080,186 B1 * | 12/2011 | Pennartz ............. | A62D 1/0035 252/607 |
| 8,188,028 B2 | 5/2012 | Baldridge et al. | |

(Continued)

FOREIGN PATENT DOCUMENTS

| | | |
|---|---|---|
| CA | 1124459 A | 6/1982 |
| CN | 101557249 A | 10/2009 |

(Continued)

OTHER PUBLICATIONS

U.S. Appl. No. 14/404,917, filed May 24, 2013, US 2015/0191748, U.S. Pat. No. 9,617,178.
U.S. Appl. No. 15/243,957, filed Aug. 22, 2016, US 2016/0360758, U.S. Pat. No. 10,334,856.
U.S. Appl. No. 15/243,958, filed Aug. 22, 2016, US 2016/0362834, U.S. Pat. No. 10,557,234.
U.S. Appl. No. 15/243,961, filed Aug. 22, 2016, US 2016/0353746, U.S. Pat. No. 10,681,914.
U.S. Appl. No. 15/444,093, filed Feb. 27, 2017, US 2017/0166467, U.S. Pat. No. 10683,222.

(Continued)

*Primary Examiner* — Jane L Stanley

(74) *Attorney, Agent, or Firm* — UltimatEdge IP Law Group P.C.; Dean G. Stathakis

(57) ABSTRACT

The present specification discloses nontoxic fire extinguishing agent compositions, devices, methods and uses of same that are safe for both users and the environment. In particular examples, the nontoxic fire extinguishing agent comprises a microbial supernatant.

18 Claims, No Drawings

(56) References Cited

U.S. PATENT DOCUMENTS

| | | | |
|---|---|---|---|
| 8,389,459 B2 | 3/2013 | Baldridge et al. | |
| 8,735,338 B2 | 5/2014 | Baldridge et al. | |
| 8,821,646 B1 | 9/2014 | Miller et al. | |
| 8,835,152 B2 | 9/2014 | Podella | |
| 8,871,682 B2 | 10/2014 | Podella et al. | |
| 8,871,698 B2 | 10/2014 | Podella et al. | |
| 8,894,861 B2 | 11/2014 | Podella et al. | |
| 9,051,535 B2 | 6/2015 | Goldfeld et al. | |
| 9,617,178 B2 | 4/2017 | Dale | |
| 10,334,856 B2 | 7/2019 | Dale et al. | |
| 2002/0187220 A1 | 12/2002 | Luhadiya | |
| 2003/0121868 A1 | 7/2003 | Barak | |
| 2004/0180411 A1 | 9/2004 | Podella et al. | |
| 2005/0118106 A1* | 6/2005 | Schaefer | A62D 1/0071 514/23 |
| 2005/0164355 A1 | 7/2005 | Vlasenko et al. | |
| 2005/0171275 A1 | 8/2005 | De et al. | |
| 2005/0266036 A1 | 12/2005 | Awada et al. | |
| 2006/0151387 A1 | 7/2006 | Yost et al. | |
| 2006/0205042 A1 | 9/2006 | Aehle et al. | |
| 2007/0029264 A1 | 2/2007 | Bowe | |
| 2007/0224249 A1 | 9/2007 | Kelly et al. | |
| 2007/0257127 A1 | 11/2007 | Iverson | |
| 2008/0138327 A1 | 6/2008 | Kelly | |
| 2008/0293813 A1 | 11/2008 | Agvald et al. | |
| 2009/0152196 A1 | 6/2009 | Podella | |
| 2009/0186761 A1 | 7/2009 | Arbogast et al. | |
| 2010/0078307 A1 | 4/2010 | Dale et al. | |
| 2010/0273495 A1 | 10/2010 | Onggosanusi et al. | |
| 2011/0052514 A1 | 3/2011 | Juesten et al. | |
| 2012/0100236 A1 | 4/2012 | Asolkar et al. | |
| 2012/0172219 A1 | 7/2012 | Podella et al. | |
| 2013/0104264 A1 | 4/2013 | Schoonneveld-Bergmans et al. | |
| 2013/0281328 A1 | 10/2013 | Podella et al. | |
| 2013/0313465 A1* | 11/2013 | Podella | A62D 1/0078 252/3 |
| 2013/0344554 A1 | 12/2013 | Bleyer et al. | |
| 2014/0056853 A1 | 2/2014 | Marrone et al. | |
| 2014/0248373 A1 | 9/2014 | Michalow et al. | |
| 2015/0045220 A1 | 2/2015 | Michalow et al. | |
| 2015/0072917 A1 | 3/2015 | Baldridge et al. | |
| 2015/0141311 A1 | 5/2015 | Podella et al. | |
| 2015/0191748 A1 | 7/2015 | Dale et al. | |
| 2015/0267151 A1 | 9/2015 | Goldfeld et al. | |
| 2016/0038779 A1* | 2/2016 | Bowen | A62D 1/0085 252/3 |
| 2016/0100587 A1 | 4/2016 | Bywater-Ekegard et al. | |
| 2016/0298056 A1 | 10/2016 | Baldridge et al. | |
| 2016/0353746 A1 | 12/2016 | Dale | |
| 2016/0362834 A1 | 12/2016 | Dale | |
| 2017/0156343 A1 | 6/2017 | Michalow et al. | |

FOREIGN PATENT DOCUMENTS

| | | |
|---|---|---|
| CN | 101951686 A | 1/2011 |
| CN | 104452385 A | 3/2015 |
| EP | 375615 A2 | 6/1990 |
| EP | 1721966 A1 | 11/2006 |
| KR | 20100088758 A | 8/2010 |
| WO | 1992011381 A1 | 7/1992 |
| WO | 1994012718 A1 | 6/1994 |
| WO | 1996000811 A1 | 1/1996 |
| WO | 1997016381 A1 | 5/1997 |
| WO | 1997028092 A1 | 8/1997 |
| WO | 1998005212 A1 | 2/1998 |
| WO | 1998023813 A1 | 6/1998 |
| WO | 00/024879 A1 | 4/2000 |
| WO | 2001079450 A1 | 10/2001 |
| WO | 02/26041 A2 | 4/2002 |
| WO | 2003031536 A1 | 4/2003 |
| WO | 03/035972 A1 | 5/2003 |
| WO | 2003037066 A2 | 5/2003 |
| WO | 2005019527 A1 | 3/2005 |
| WO | 2005054475 A1 | 6/2005 |
| WO | 2005/067531 A2 | 7/2005 |
| WO | 2005069849 A2 | 8/2005 |
| WO | 2006119052 A2 | 11/2006 |
| WO | 2008111613 A1 | 9/2008 |
| WO | 2010115021 A1 | 10/2010 |
| WO | 2010148535 A1 | 12/2010 |
| WO | 2011016008 A1 | 2/2011 |
| WO | 2012051328 A2 | 4/2012 |
| WO | 2013180756 A1 | 12/2013 |
| WO | 2017035099 A1 | 3/2017 |
| WO | 2017035100 A1 | 3/2017 |
| WO | 2017035101 A1 | 3/2017 |

OTHER PUBLICATIONS

U.S. Appl. No. 16/446,583, filed Jun. 19, 2019, US 2019/0307130, U.S. Pat. No. 11,116,224.
U.S. Appl. No. 16/729,236, filed Dec. 27, 2019, US 2020/0131701.
U.S. Appl. No. 16/729,240, filed Dec. 27, 2019, US 2020/0138037.
U.S. Appl. No. 16/729,243, filed Dec. 27, 2019, US 2020/0140304.
U.S. Appl. No. 17/240,919, filed Apr. 26, 2021, US 2021/0329913.
U.S. Appl. No. 17/446,961, filed Sep. 4, 2021.
Chaichi et al., "Surfactant Application on Yield and Irrigation Water Use Efficiency in Corn under Limited Irrigation", Crop Sci. 55(1): 386 (2015).
CNIPA, Second Office Action for Chinese Patent Application Serial No. 201680061816.2, pp. 9 (Mar. 15, 2021).
Desai, et al., "Microbial Production of Surfactants and Their Commercial Potential", Microbiol. Mol. Biol. Rev., 1997, 61(1): 47-64.
EPO, Extended Search Report for European Patent Application Serial No. EP13796699.0, pp. 12 (Jul. 12, 2016).
EPO, Extended Search Report for European Patent Application Serial No. EP16839956.6, pp. 12 (Jan. 14, 2019).
EPO, Extended Search Report for European Patent Application Serial No. EP16839957.4, pp. 11 (Apr. 17, 2019).
EPO, Extended Search Report for European Patent Application Serial No. EP16839958.2, pp. 12 (Sep. 30, 2019).
EPO, Extended Search Report for European Patent Application Serial No. EP19160826.4, pp. 5 (Apr. 3, 2019).
Frolund, et al., "Enzymatic Activity in the Activated-Sludge Floc Matrix", Appl. Microbiol. Biotechnol., 1995, 43(3): 755-561.
Goel, "Enzyme Activities under Anaerobic and Aerobic Conditions in Activated Sludge Sequencing Batch Reactor", Water Research, 1998, 32(7): 2081-2088.
Ito, et al., "Sophorolipids from Torulopsis bombicola: Possible Relation to Alkane Update", Appl. Environ, Micobiol., 1982, 43(6): 1278-1283.
JPO, Office Action for Japanese Patent Application Serial No. 2018-528937, pp. 2 (Jul. 13, 2021).
JPO, Office Action for Japanese Patent Application Serial No. 2018-528938, pp. 4 (Aug. 17, 2021).
Kastner, "Formation of Bound Residues during Microbial Degradation of [14C]Anthracene in Soil", Appl. Environ. Microbiol., 1999, 65(5): 1834-1842.
Sensient Flavors LLC, "Tastone 154, Technical Information", 2010.
Sukumaran, et al., "Microbial Celluloses—Production, Applications, and Challenges", J. Sci. Indus. Res., 2005, 64: 832-844.
WIPO, PCT Form IB373, International Preliminary Report on Patentability for International Patent Application Serial No. PCT/US2013/000140, pp. 12 (Dec. 2, 2014).
WIPO, PCT Form IB373, International Preliminary Report on Patentability for International Patent Application Serial No. PCT/US2016/048092, pp. 6 (Mar. 8, 2018).
WIPO, PCT Form IB373, International Preliminary Report on Patentability for International Patent Application Serial No. PCT/US2016/048093, pp. 5 (Mar. 8, 2018).
WIPO, PCT Form IB373, International Preliminary Report on Patentability for International Patent Application Serial No. PCT/US2016/048094, pp. 5 (Mar. 8, 2018).
WIPO, PCT Form ISA210, International Search Report for International Patent Application Serial No. PCT/US2013/000140, pp. 2 (Jul. 22, 2013).

(56) References Cited

OTHER PUBLICATIONS

WIPO, PCT Form ISA210, International Search Report for International Patent Application Serial No. PCT/US2016/048092, pp. 10 (Nov. 15, 2016).
WIPO, PCT Form ISA210, International Search Report for International Patent Application Serial No. PCT/US2016/048093, pp. 8 (Oct. 24, 2016).
WIPO, PCT Form ISA210, International Search Report for International Patent Application Serial No. PCT/US2016/048094, pp. 7 (Nov. 4, 2016).
WIPO, PCT Form ISA237, Written Opinion for International Patent Application Serial No. PCT/US2013/000140, pp. 11 (Jul. 22, 2013).
WIPO, PCT Form ISA237, Written Opinion for International Patent Application Serial No. PCT/US2016/0048093, pp. 4 (Oct. 24, 2016).
WIPO, PCT Form ISA237, Written Opinion for International Patent Application Serial No. PCT/US2016/048092. pp. 5 (Nov. 15, 2016).
WIPO, PCT Form ISA237, Written Opinion for International Patent Application Serial No. PCT/US2016/048094, pp. 4 (Nov. 4, 2016).
Witek-Krowiak, et al., "Ultrafiltrative Separation of Rhamnolipid from Culture Medium", World J. Microbiol. Biotechnol., 2011, 27: 1961-1964.
Xu, et al., "Biosurfactants for Microbubble Preparation and Application", Int. J. Mol. Sci., 2011, 12: 462-475.
Xu, et al., "Research Review of Wastewater Treatment Technology with Hydrolytic Enzymes", J. Chongqing Univ. Sci. Technol. 12(6), 2010, 156-161.

* cited by examiner

NON-TOXIC FIRE EXTINGUISHING COMPOSITIONS, DEVICES AND METHODS OF USING SAME

This application claims the benefit of priority and is entitled to the filing date pursuant to 35 U.S.C. § 119(e) of U.S. Provisional Patent Application 63/015,640, filed Apr. 26, 2020, which is hereby incorporated by reference in its entirety.

FIELD OF THE INVENTION

The present disclosure generally relates to fire extinguishing compositions, methods and devices utilizing same, that include a fire extinguishing agent comprised of a treated, fermented microbial supernatant and, optionally, a surfactant.

BACKGROUND

Unintentional fires are a serious problem around the world, whether they be wildfires, dumpster fires, structural fires, vehicular fires, kitchen fires and the like. There is always a need for novel compositions, devices and methods of use for extinguishing such fires. As is known, when a fire breaks out, it is important to efficiently extinguish the fire in order to minimize environmental and structural damage and reduce the potential of injury and loss of human and animal life. Conventional fire extinguishing compositions are known and include various compositions, including plain water, gases (such as $CO_2$, for example), as well as various aqueous extinguishing agents having a variety of components. One such extinguishing agent includes aqueous potassium carbonate (APC), the agent mainly consisting of an aqueous potassium carbonate solution. Particular APC containing extinguishing agents also contain a synthetic surfactant in order to lower the surface tension thereof and improve the wetting property on combustible materials such as woods, fiber and resin. Furthermore, extinguishing agents having surfactants as one of their components display improved adhesive characteristics of the extinguishing agent to the substances on fire. Known APC containing extinguishing agents utilize this property and are typically foamed by synthetic surfactant. Due to the above properties, fire extinguishing effect, reheat-prevention effect and fire spread-prevention effect are improved, and it is known that APC containing extinguishing agents can extinguish a fire in a shorter time and in a smaller amount than water alone. However, although effective as a fire extinguishing agent, APC containing extinguishing agents are not particularly safe for users and or the environment as they are quite basic, having a pH of around 12 to 13.

Accordingly, there is a need for fire extinguishing compositions containing fire extinguishing agents, methods and devices of using same, that are effective in quenching a fire within a short period of time, and further, are non-toxic to the environment, people and animals in general. In addition, fire extinguishing compositions and agents that are the subject of the instant disclosure have been found to, when utilized and applied to plants, provide the added benefit of increasing the health and vigor of plants. Thus, the methods for extinguishing fires utilizing the fire extinguishing compositions of the present invention have the added benefit of not only being very effective at extinguishing a fire, such as and including, for example, a wildfire, but also, provide the added benefit of increasing the health and vigor of plants that survive a fire and/or are seeded/placed or grow over a burn area thereafter. Such fire extinguishing compositions, devices and methods of use are especially desirous for putting out wildfires via dispersion of the fire extinguishing composition via ground crews, sprinkler systems, land and air vehicles (e.g. helicopters, drones, planes and airships). The present invention fulfills these, and related needs associated with environmentally safe methods for extinguishing fires.

SUMMARY

Aspects of the present specification disclose compositions, including dry powdered compositions. A dry powered composition disclosed herein comprises a dried treated microbial supernatant and one or more dried non-ionic surfactants or one or more biosurfactants. The dried treated fermented microbial supernatant includes bio-nutrients, minerals and amino acids but lacks any active enzymes, activatable pro-enzymes, or any enzymatic activity. A dried treated fermented microbial supernatant disclosed herein can further lack live microorganisms such as yeast or bacteria. The disclosed dry powered compositions may further comprise one or more anionic surfactants. The disclosed dry powered compositions are biodegradable and non-toxic to humans, mammals, plants and the environment. In aspects, a liquid composition is a dry powdered composition disclosed herein that is dissolved using a solvent.

Aspects of the present specification disclose compositions, including liquid compositions. A liquid composition disclosed herein comprises a treated microbial supernatant and one or more non-ionic surfactants or one or more biosurfactants. The treated fermented microbial supernatant includes bio-nutrients, minerals and amino acids but lacks any active enzymes, activatable pro-enzymes, or any enzymatic activity. A treated fermented microbial supernatant disclosed herein can further lack live microorganisms such as yeast or bacteria. The disclosed liquid compositions may further comprise one or more anionic surfactants. The disclosed liquid compositions are biodegradable and non-toxic to humans, mammals, plants and the environment.

Aspects of the present specification disclose compositions, including paste compositions and colloidal compositions such as a foam, aerosol, emulsion, gel, or sol. Such compositions are typically produced using a dry powdered composition or liquid composition disclosed herein along with the appropriate solvent, diluent, thickener, aerosol and/or other components.

Aspects of the present specification disclose a fire extinguishing kit. The disclosed fire extinguishing kit comprises a composition disclosed herein and instructions for how to use the composition to retard, suppress, extinguish or prevent afire or spread of a fire. In aspects, the disclosed kit can comprise a dry powdered composition disclosed herein and instructions for how to use the dry powdered compositions, an optionally a solvent. Exemplary instructions provide that a dry powdered composition disclosed herein is dissolved in a solvent to form a liquid composition. An exemplary solvent includes water or a water-based solution. In aspects, the disclosed kit can comprise a liquid composition disclosed herein and instructions for how to use the liquid composition.

Aspects of the present specification disclose methods of controlling a fire. Additional aspects of the present specification disclose uses of a composition disclosed herein for controlling a fire. Aspects of the disclosed methods and uses comprises applying an effective amount of a composition disclosed herein to a fire. In aspects, the disclosed methods and uses comprise the steps of dissolving a dry powdered composition disclosed herein with a solvent to form a liquid composition and applying an effective amount of the liquid composition to a fire. In other aspects, the disclosed methods and uses comprise the steps applying an effective amount of a liquid composition to a fire. In other aspects, the disclosed methods and uses comprise the steps applying an effective amount of a paste or colloidal composition to a fire. Such application results in the control of the fire, including, but are not limited to, retarding, suppressing, and/or extinguishing a fire already ignited; retarding, suppressing, and/or preventing an ignition point from creating a fire; and/or deterring, suppressing, re-routing, and/or preventing a fire from spreading to one or more areas not on fire.

Other aspects of the disclosed methods and uses comprises applying an effective amount of a composition disclosed herein to one or more areas where control of a fire is desired. In aspects, the disclosed methods and uses comprise the steps of dissolving a dry powdered composition disclosed herein with a solvent to form a liquid composition and applying an effective amount of the liquid composition to one or more areas where control of a fire is desired. In other aspects, the disclosed methods and uses comprise the steps applying an effective amount of a liquid composition to one or more areas where control of a fire is desired. In other aspects, the disclosed methods and uses comprise the steps applying an effective amount of a paste or colloidal composition to one or more areas where control of a fire is desired. Such application results in the control of the fire, including, but are not limited to, retarding, suppressing, and/or extinguishing a fire already ignited; retarding, suppressing, and/or preventing an ignition point from creating a fire; and/or deterring, suppressing, re-routing, and/or preventing a fire from spreading to one or more areas not on fire.

Aspects of the present specification disclose fire extinguishing devices and systems. The disclosed fire extinguishing devices and systems are comprised of a composition disclosed herein. In an aspect, the disclosed devices and systems comprise a composition disclosed herein formulated as a dry powder, liquid, paste or colloidal composition disclosed herein.

DETAILED DESCRIPTION

Fire is the rapid oxidation of a material in the exothermic chemical process of combustion, releasing heat, light, and various reaction products. Fire is hot because the conversion of the weak double bond in molecular oxygen to the stronger bonds in the combustion products carbon dioxide and water releases energy. At a certain point in the combustion reaction, called the ignition point, flames are produced. The flame is the visible portion of the fire. Flames consist primarily of carbon dioxide, water vapor, oxygen and nitrogen. If hot enough, the gases may become ionized to produce plasma. Depending on the substances alight, and any impurities outside, the color of the flame and the fire's intensity will be different. Fire in its most common form can result in conflagration, which has the potential to cause physical damage through burning.

Fires start when a source of fuel such as a flammable or a combustible material, in combination with a sufficient quantity of a source of oxidizer such as oxygen gas or another oxygen-rich compound (though non-oxygen oxidizers exist), is exposed to a source of heat or ambient temperature above the flash point for the fuel/oxidizer mix, and is able to sustain a rate of rapid oxidation that produces a chain reaction. This is commonly called the fire tetrahedron. Fire cannot exist without all of these elements in place and in the right proportions. Once ignited, a chain reaction must take place whereby fires can sustain their own heat by the further release of heat energy in the process of combustion and may propagate, provided there is a continuous supply of an oxidizer and fuel.

Fire can be extinguished by removing anyone of the elements of the fire tetrahedron. For example, a fire can be extinguished by removing the source of heat, such as by employing a heat absorbing compound that absorbs more heat than the fire can generate, a process called cooling the fire. Similarly, a fire can be extinguished by removing the source of fuel, a process called starving the fire. Likewise, a fire can be extinguished by removing the source of oxidizer, a process called smothering the fire.

Without wishing to be limited by its theory, the presently disclosed compositions cools a heat source, starves a fuel source and/or smother an oxidizer source of a fire, resulting in the retardation, suppression, extinguishing or prevention of the fire or spread of the fire. This mechanism of action is tied to the ability of a composition disclosed herein to absorb more heat than the fire can generate, remove the combustible material serving as the source of fuel, and/or removing the oxidizer source. Regardless of the theory of operation, the disclosed compositions and methods and uses offer an alternative means that does not rely on toxic chemicals currently used in fire extinguishants. Rather, compositions and methods and uses disclosed herein act by exploiting an inherent process to remove one or more heat, fuel or oxidizer sources contributing to the fire. In addition, the components of the disclosed compositions been proven to be substantially non-toxic to man and domestic animals and which have minimal adverse effects on wildlife and the environment.

Aspects of the present specification disclose, in part, a composition. A composition disclosed herein comprises a treated fermented microbial supernatant and one or more non-ionic surfactants. The treated fermented microbial supernatant includes bio-nutrients, minerals and amino acids but lacks any active enzymes, activatable pro-enzymes, or any enzymatic activity. In aspects of this embodiment, a treated fermented microbial supernatant disclosed herein lacks live microorganisms such as yeast or bacteria. Additionally, a composition itself lacks any active enzymes, activatable pro-enzymes, or any enzymatic activity. In aspects of this embodiment, a composition disclosed herein lacks live microorganisms such as yeast or bacteria. A composition disclosed herein can be a solid formulation, a liquid formulation or a colloidal formulation. A solid formulation includes a dry powdered composition, a liquid formulation includes a liquid composition and a paste composition, and a colloidal formulation includes a colloidal composition such as, e.g., a foam, an aerosol, an emulsion, a gel, or a sol. A composition disclosed herein can be produced in a concentrated form requiring dilution before use or in a ready-to-used form. A composition disclosed herein can further include other component or components such as a diluent, a dispersing agent, a binding agent, a film forming agent, a preservative or the like.

Aspects of the present specification disclose, in part, a dry powered composition. A dry powered composition disclosed herein comprises a dried treated microbial supernatant and one or more dried non-ionic surfactants. The dried treated fermented microbial supernatant includes bio-nutrients, minerals and amino acids but lacks any active enzymes, activatable pro-enzymes, or any enzymatic activity. In aspects of this embodiment, a dried treated fermented microbial supernatant disclosed herein lacks live microorganisms such as yeast or bacteria.

In aspects of this embodiment, a dry powdered composition disclosed herein comprises, e.g., about 5% to about 15% by weight of dried treated fermented microbial supernatant and about 75% to about 95% by weight of one or more non-ionic surfactants. In other aspects of this embodiment, a composition disclosed herein comprises, e.g., about 7% to about 12% by weight of a dried treated fermented microbial supernatant and about 80% to about 90% by weight of one or more non-ionic surfactants. In yet other aspects of this embodiment, a dry powdered composition disclosed herein comprises, e.g., about 8% to about 10% by weight of dried treated fermented microbial supernatant and about 85% to about 90% by weight of one or more non-ionic surfactants. In still other aspects of this embodiment, a dry powdered composition disclosed herein comprises, e.g., about 9% to about 10% by weight of a dried treated fermented microbial supernatant and about 87% to about 90% by weight of one or more non-ionic surfactants. In other aspects of this embodiment, a dry powdered composition disclosed herein comprises, e.g., about 9% to about 10% by weight of a dried treated fermented microbial supernatant and about 89% to about 90% of one or more non-ionic surfactants. In yet other aspects of this embodiment, a dry powdered composition disclosed herein comprises, e.g., about 9% to about 9.2% by weight of dried treated fermented microbial supernatant and about 89% to about 89.9% by weight of one or more non-ionic surfactants.

In some embodiments, a dry powered composition disclosed herein comprises a dried treated microbial supernatant and one or more dried non-ionic biosurfactants. The dried treated fermented microbial supernatant includes bio-nutrients, minerals and amino acids but lacks any active enzymes, activatable pro-enzymes, or any enzymatic activity. In aspects of this embodiment, a dried treated fermented microbial supernatant disclosed herein lacks live microorganisms such as yeast or bacteria.

In aspects of this embodiment, a dry powdered composition disclosed herein comprises, e.g., about 5% to about 15% by weight of dried treated fermented microbial supernatant and about 75% to about 95% by weight of one or more non-ionic biosurfactants. In other aspects of this embodiment, a composition disclosed herein comprises, e.g., about 6% to about 14% by weight of a dried treated fermented microbial supernatant and about 80% to about 95% by weight of one or more non-ionic biosurfactants. In yet other aspects of this embodiment, a dry powdered composition disclosed herein comprises, e.g., about 6% to about 12% by weight of dried treated fermented microbial supernatant and about 85% to about 95% by weight of one or more non-ionic biosurfactants. In still other aspects of this embodiment, a dry powdered composition disclosed herein comprises, e.g., about 7% to about 11% by weight of a dried treated fermented microbial supernatant and about 87% to about 93% by weight of one or more non-ionic biosurfactants. In other aspects of this embodiment, a dry powdered composition disclosed herein comprises, e.g., about 8% to about 10% by weight of a dried treated fermented microbial supernatant and about 89% to about 91% of one or more non-ionic biosurfactants. In yet other aspects of this embodiment, a dry powdered composition disclosed herein comprises, e.g., about 9% to about 9.2% by weight of dried treated fermented microbial supernatant and about 89% to about 89.9% by weight of one or more non-ionic biosurfactants.

Aspects of the present specification disclose, in part, a liquid composition. A liquid composition disclosed herein comprises a treated microbial supernatant and one or more non-ionic surfactants. The treated fermented microbial supernatant includes bio-nutrients, minerals and amino acids but lacks any active enzymes, activatable pro-enzymes, or any enzymatic activity. In aspects of this embodiment, a treated fermented microbial supernatant disclosed herein lacks live microorganisms such as yeast or bacteria.

In aspects of this embodiment, a liquid composition disclosed herein comprises, e.g., about 15% to about 95% by weight of treated fermented microbial supernatant and about 1% to about 25% by weight of one or more non-ionic surfactants. In another aspect of this embodiment, a liquid composition disclosed herein comprises, e.g., about 80% to about 97% of treated fermented microbial supernatant and about 3%-20% of one or more non-ionic surfactants. In yet another aspect of this embodiment, a liquid composition disclosed herein comprises, e.g., about 85% to about 95% of treated fermented microbial supernatant and about 5%-15% of one or more non-ionic surfactants. In still another aspect of this embodiment, a liquid composition disclosed herein comprises, e.g., about 87% to about 93% of treated fermented microbial supernatant and about 7%-13% of one or more non-ionic surfactants. In another aspect of this embodiment, a liquid composition disclosed herein comprises, e.g., about 88% to about 92% of treated fermented microbial supernatant and about 8%-12% of one or more non-ionic surfactants. In another aspect of this embodiment, a liquid composition disclosed herein comprises, e.g., about 89% to about 91% of treated fermented microbial supernatant and about 9%-11% of one or more non-ionic surfactants.

In some embodiments, a liquid composition disclosed herein comprises a treated microbial supernatant and one or more non-ionic biosurfactants. The treated fermented microbial supernatant includes bio-nutrients, minerals and amino acids but lacks any active enzymes, activatable pro-enzymes, or any enzymatic activity. In aspects of this embodiment, a treated fermented microbial supernatant disclosed herein lacks live microorganisms such as yeast or bacteria.

In aspects of this embodiment, a liquid composition disclosed herein comprises, e.g., about 15% to about 95% by weight of treated fermented microbial supernatant and about 1% to about 25% by weight of one or more non-ionic biosurfactants. In another aspect of this embodiment, a liquid composition disclosed herein comprises, e.g., about 80% to about 97% of treated fermented microbial supernatant and about 3%-20% of one or more non-ionic biosurfactants. In yet another aspect of this embodiment, a liquid composition disclosed herein comprises, e.g., about 85% to about 95% of treated fermented microbial supernatant and about 5%-15% of one or more non-ionic biosurfactants. In still another aspect of this embodiment, a liquid composition disclosed herein comprises, e.g., about 87% to about 93% of treated fermented microbial supernatant and about 7%-13% of one or more non-ionic biosurfactants. In another aspect of this embodiment, a liquid composition disclosed herein comprises, e.g., about 88% to about 92% of treated fermented microbial supernatant and about 8%-12% of one or more non-ionic biosurfactants. In another aspect of this embodiment, a liquid composition disclosed herein comprises, e.g., about 89% to about 91% of treated fermented microbial supernatant and about 9%-11% of one or more non-ionic biosurfactants.

Aspects of the present specification disclose, in part, a colloidal composition. A colloidal composition disclosed herein comprises a treated microbial supernatant and one or more non-ionic surfactants. The treated fermented microbial supernatant includes bio-nutrients, minerals and amino acids but lacks any active enzymes, activatable pro-enzymes, or any enzymatic activity. In aspects of this embodiment, a treated fermented microbial supernatant disclosed herein lacks live microorganisms such as yeast or bacteria. A colloidal composition disclosed herein includes, without limitation, a foam composition, an aerosol composition, an emulsion composition, a gel composition, or a sol composition. Typically a colloidal composition disclosed herein is a liquid composition disclosed herein that is formulated to include one or more thickening agents, dispersing agents, binding agents, foaming agents, stabilizing agents, film forming agents, or the like.

A foam composition disclosed herein can be made using a liquid composition disclosed herein that reacts chemically with other compounds to generate gas and create a foam composition disclosed herein or mechanically by mixing a gas with a liquid composition disclosed herein to create a foam composition disclosed herein. In some embodiments, a foam composition disclosed herein does not comprise a foam stabilizing agent. In some embodiments, a foam composition disclosed herein can further optionally include a foam stabilizing agent. A foam composition disclosed herein produced mechanically can be classified as a low expansion foam, a medium expansion foam, and high expansion foam. A low expansion foam has an expansion ratio of about 2:1 to about 20:1 can be produced by self-aspirating foam branch pipes. A medium expansion foam has an expansion ratio of about 20:1 to about 200:1 can be produced by self-aspirating foam branch pipes with nets. A high expansion foam has an expansion ratio of above 200:1, and typically between about 500:1 to about 1,500:1 can be produced by foam generators with air fans.

Aspects of the present specification disclose, in part, a fermented microbial supernatant. A fermented microbial supernatant disclosed herein can be prepared by culturing a yeast strain, a bacterial strain, or a combination of both a yeast strain and a bacterial strain in a fermenting medium comprising a sugar source, a malt and a magnesium salt. In an aspect of this embodiment, only a single yeast strain is used in a fermenting medium. In another aspect of this embodiment, two or more different yeast strains are used in a fermenting medium. In yet another aspect of this embodiment, only a single bacterial strain is used in a fermenting medium. In still another aspect of this embodiment, two or more different bacterial strains are used in a fermenting medium. In another aspect of this embodiment, one or more different yeast strains are used in conjunction with one or more different bacteria in a fermenting medium. In yet another aspect of this embodiment, two, three, four, five or more different yeast strains are used in conjunction with two, three, four, five or more different bacteria in a fermenting medium.

A sugar source includes, without limitation, sucrose from molasses, raw cane sugar, soybeans or mixtures thereof. Molasses generally contains up to about 50% sucrose in addition to reducing sugars such as glucose and maltase as well as ash, organic non-sugars and some water. The presence of the sugars of the type found in the molasses is important in encouraging the activity of the enzymes and the yeast bacteria by which they are produced. Although the untreated cane blackstrap molasses is preferred, other molasses such as beet molasses, barrel molasses and the like may also be used as a natural source of the materials required for the enzymatic fermentation. The amount of molasses useful in preparing a fermenting medium disclosed herein is between 40% and about 80% by weight, and preferably between about 55% and about 75% by weight. It will be appreciated that specific amounts of the molasses utilized may be varied to yield optimum compositions desired.

Raw cane sugar is a sugar product which has not been refined and which contains residual molasses as well as other natural impurities. Although it is not clearly understood, it has been found that the presence of raw sugar in the fermentation reaction yields significantly improved properties as compared to the use of refined sugars which contain residual chemicals used in the decolorization and final purification and refinement which may have some deleterious effect on the yeast and malt enzymes. It has been found that optimum biological and enzymatic properties of the disclosed fermenting medium are improved where a portion of the fermentable materials present in the mixture comprises raw sugar. The amount of raw cane sugar useful in preparing a fermenting medium disclosed herein may be about 10% and about 40% by weight, and preferably between about 10% and about 30% by weight. It will be appreciated that specific amounts of the raw cane sugar utilized may be varied to yield optimum compositions desired.

The essential enzymes which advantageously contribute to the fermentation reaction are provided by the malt and the yeast and/or bacteria. The specific malt utilized is preferably a diastatic malt which contains enzymes including diastase, maltase and amylase. The malt also is believed to improve the activity of the yeast and/or bacteria in addition to contributing to the overall potency and activity of the enzymatic composition within the final product mixture. The amount of malt useful in preparing a fermenting medium disclosed herein may be between about 3% and about 15% by weight, and preferably between about 7% and about 12% by weight. It will be appreciated that specific amounts of the malt utilized may be varied to yield optimum compositions desired.

Fermentation is a metabolic process that results in the breakdown of carbohydrates and other complex organic substances into simpler substances like sugars, acids, gases or alcohol. Fermentation can occur in yeast, bacteria and mold. Fermentation includes ethanol fermentation and lactic acid fermentation. Lactic acid fermentation includes homolactic fermentation and heterolactic fermentation.

A yeast refers to any fermentation fungi that can be produce the needed enzymes for a fermentation reaction that results in, for example the conversion of carbohydrates into carbon dioxide and alcohols. A number of enzymes are produced by the active yeast during the fermentation reaction and include both hydrolytic and oxidative enzymes such as invertase, catalase, lactase, maltase, carboxylase and others. Yeast include yeast strains useful in food processing fermentation, such as, e.g., bean-based fermentation, dough-based fermentation, grain-based fermentation, vegetable-based fermentation, fruit-based fermentation, honey-based fermentation, dairy-based fermentation, fish-based fermentation, meat-based fermentation and tea-based fermentation. A non-exhaustive list of particular yeast genera useful in a fermentation reaction disclosed herein include, but is not limited, *Brettanomyces, Candida, Cyberlindnera, Cystofilobasidium, Debaryomyces, Dekkera, Fusarium, Geotrichum, Issatchenkia, Kazachstania, Kioeckera, Kluyveromyces, Lecanicillium, Mucor, Neurospora, Pediococcus, Penicillium, Pichia, Rhizopus, Rhodosporidium, Rhodotorula, Saccharomyces, Schizosaccharomyces, Thrichosporon, Torulaspora, Torulopsis, Verticillium, Yarrowia, Zygo-* saccharomyces and *Zygotorulaspora*. Species of yeast useful in a fermentation reaction disclosed herein belong to, without limitation A non-exhaustive list of particular yeast species useful in a fermentation reaction disclosed herein includes, but is not limited, *B. anomalus, B. bruxellensis, B. claussenii, B. custersianus, B. naardenensis, B. nanus, C. colliculosa, C. exiguous, C. humicola, C. kefyr, C. krusei, C. milleri, C. mycoderma, C. pelliculosa, C. rugose, C. stellate, C. tropicalis, C. utilis, C. valida, C. vini, C. zeylanoides, Cb. mrakii, Cs. infimominiatum, D. hansenii, D. kloeckeri, Dk. anomala, Dk. bruxellensis, F. domesticum, G. candidum, I. orientalis, K. exigua, K. unispora, Kl. akicana, Kl. apis, Kl. javanica, Ku. lactis, Ku. manxianus, Ku. marxianus, L. lecanii, M. hiemalis, M. plumbeus, M. racemosus, M. racemosus, N. intermedia, P. cerevisiae, Pn. album, Pn. camemberti, Pn. caseifulvum, Ph. chrysogenum, Pn. commune, Pn. nalgiovense, Pn. roqueforti, Pn. solitum, Pi. fermentans, R. microspores, Rs. infirmominiatum, Rt. glutinis, Rt. minuta, Rt. rubra, S. bayanus, S. boulardii, S. cadsbergensis, S. cerevisiae, S. eubayanus, S. paradoxus, S. pastoranus, S. rouzii, S. uvarum, Sc. pombe, Th. beigelii, T. delbrueckii, T. franciscae, T. pretoriensis, T. microellipsoides, T. globosa, T. indica, T. maleeae, T. quercuum, To. versatilis, V. lecanii, Y. lipolytica, Z bailii, Z bisporus, Z. cidri, Z fermentadi, Z lorentinus, Z. kombuchaensis, Z lentus, Z mellis, Z. microellipsoides, Z mrakii, Z pseudorouxii* and *Z. rouxii* and *Zt. lorentina*. A preferred yeast is *Saccharomyces cerevisiae* commonly available as baker's yeast.

Bacteria refer to any fermentation bacteria that can be produce the needed enzymes for a fermentation reaction that results in, for example the production of alcohols like ethanol or acids like acetic acid, lactic acid and/or succinic acid. A non-exhaustive list of particular bacterial genera useful in a fermentation reaction disclosed herein include, but is not limited, *Acetobacter, Arthrobacter, Aerococcus, Bacillus, Bifidobacterium, Brachybacterium, Brevibacterium, Bamobacterium, Camobacterium, Corynebacterium, Enterococcus, Escherichia, Gluconacetobacter, Gluconobacter, Hafnia, Halomonas, Kocuria, Lactobacillus, Lactococcus, Leuconostoc, Macrococcus, Microbacterium, Micrococcus, Neisseria, Oenococcus, Pediococcus, Propionibacterium, Proteus, Pseudomonas, Psychrobacter, Salmonella, Sporolactobacillus, Staphylococcus, Streptococcus, Streptomyces, Tetragenococcus, Vagococcus, Weissells* and *Zymomonas*. A non-exhaustive list of particular bacterial species useful in a fermentation reaction disclosed herein includes, but is not limited, *A. aceti, A. fabarum, A. lovaniensis, A. malorum, A orientalis, A. pasteurianus, A. pasteurianus, A. pomorum, A. syzygii, A. tropicalis, Ar. arilailensis, Ar. Bergerei, Ar. Globilbrmis, Ar. nicotianae, Ar. variabilis, B. cereus, B. coagulans, B. licheniformis, B. pumilus, B. sphaericus, B. stearothermophilus, B. subtilis, B. adolescentis, B. animalis, B. bifidum, B. breve, B. infantis, B. lactis, B. longum, B. pseudolongum, B. thermophilum, Br. alimentanum, Br. alimentanum, Br. tyrofermentans, Br. tyrofermentans, Bv. aurantiacum, Bv. casei, Bv. linens, C. divergens, C. maltaromaticum, C. piscicola, C. ammoniagenes, Co. casei, Co. flavescens, Co. mooneparkense, Co. variabile, E. faecalis, E. faecium, G. azotocaptans, G. diazotrophicus, G. entanff, G. europaeus, G. hansenff, G. johannae, G. oboediens, G. xylinus, Gl. oxydans, H. alvei, Hl. elongate, K. rhizophila, K. rhizophila, K. varians, K. varians, L. acetotolerans, L. acidifarinae, L. acidipiscis, L. alimentarius, L. brevis, L. bucheri, L. cacaonum, L. casei, L. cellobiosus, L. collinoides, L. composti, L. corynifbrmis, L. orispatus, L. curvatus, L. delbrueckii, L dextrinicus, L. diolivorans, L. fabifermentans, L. farcimfnis, L. fermentum, L. gasseri, L. ghanensis, L. hanmmesii, L. harbinensis, L. helveticus, L. hilgardii, L. homohiochii, L. jensenii, L. johnsonii, L. keflranofaciens, L. kefri, L. kimchi, L. kisonensis, L. kunkeei, L. mali, L. manihotivorans, L. mindensis, L. mucosae, L. nagelii, L. namuresis, L. nantesis, L. nodensis, L. oeni, L. otakiensis, L. panis, L. parabrevis, L. parabuchneri, L. paracasei, L. parakefri, L. paralimentarius, L. paraplantarum, L. pentosus, L. perolens, L. plantarum, L. pobuzihii, L. pontis, L. rapi, L. reuteri, L. rhamnosus, L. rossiae, L. sakei, L. salivarius, L. sanfranciscensis, L. satsumensis, L. secaliphilus, L. senmaizukei, L. siliginis, L. similis, L. spicheri, L. suebicus, L. sunkii, L. tucceli, L. vaccinostercus, L. versmoldesis, L. yamanashiensis, Lc. lactis, Lc. raffinolactis, Le. camosum, Le. citreum, Le. fallax, Le. holzapfelii, Le. inhae, Le. kimchi, Le. lactis, Le. mesenteroides, Le. palmae, Le. Pseudomesenteroides, M. caseolyticus, Mb. fbliorum, Mb gubbeenense, Mc. luteus, Mc. lylae, P. acidilactici, P. pentosaceus, P. acidipropionici, P. freudenreichii, P. jensenii, P. thoenii, Pr. vulgars, Ps. fluorescens, Py. celer, S. camosus, S. condiment, S. equorum, S. fleurettii, S. piscifermentans, S. saphrophyticus, S. scium, S. simulans, S. succinus, S. vitulinus, S. wameri, S. xylosus, St. cremorns, St. gallolyticus, St. salivarius, St. thermophiles, St. griseus, T. halophilus, T. koreensis, W. beninensis, W. cibaria, W. fabara, W. ghanesis, W. koreensis, W. paramesenteroides, W. thailandensis*, and *Z. mobilis*.

Mold refer to any fermentation mold that can be produce the needed enzymes for a fermentation reaction that results in, for example the production of alcohols like ethanol or acids like acetic acid, lactic acid and/or succinic acid. A non-exhaustive list of particular mold genera useful in a fermentation reaction disclosed herein include, but is not limited, *Aspergillus*. A non-exhaustive list of particular mold species useful in a fermentation reaction disclosed herein includes, but is not limited, *A. acidus, A. fumgatus, A niger, A. oryzae*, and *A. sojae*.

It will be appreciated that actual amounts of the various types of enzymes produced will be dependent on a number of factors including the types of molasses and sugar used in preparing the fermentation mixture. However, again it is believed that, in utilizing the molasses and raw sugar, optimum enzyme yields and activity are obtained. In an embodiment, the amount of yeast useful in preparing a fermenting medium disclosed herein may be between about 0.2% and about 5% by weight, and preferably between about 1% and about 3% by weight. It will be appreciated that specific amounts of the yeast utilized may be varied to yield optimum compositions desired.

The presence of a small amount of inorganic catalyst such as a magnesium salt enhances the activity of the enzymes not only during the fermentation reaction but thereafter in the product composition in attacking and decomposing the organic waste materials. A preferred magnesium salt is magnesium sulfate. The amount of magnesium salt useful in preparing a fermenting medium disclosed herein may be between about 0.1% and about 5% by weight, and preferably between about 1% and about 3% by weight. It will be appreciated that specific amounts of the magnesium salt utilized may be varied to yield optimum compositions desired.

To prepare a fermented microbial supernatant, the molasses, sucrose and magnesium salt are added to a suitable amount of warm water. Although the specific amount of water used is not particularly critical, typically suitable amounts of water are from about 2 to about 20 times the total weight of the other ingredients of the fermenting medium used in the fermentation reaction. This amount of water is sufficient to facilitate easy admixture as well as to activate the yeast, bacterial and/or mold and dissolve the other materials. In addition, the temperature of the water cannot be too hot such that the heat inactivates the malt and yeast enzymes needed for fermentation. Thus, for example, water temperatures greater than about 65° C. must be avoided and preferred temperatures are between about 25° C. to about 45° C. The use of cold water may result in unduly slow fermentation reaction rates and, thus, should also be avoided where increased reaction rates are desired. After the molasses, sugar and magnesium salt are effectively mixed and dissolved, the malt and the yeast are added, the mixture stirred and allowed to set until fermentation is essentially complete. The reaction time may be between about 2 and about 5 days at temperatures between about 20° C. and about 45° C. Completion may be readily ascertained by noting that the effervescence of the reacting mixture has substantially subsided. At the end of the fermentation reaction, the fermented microbial culture is centrifuged to remove the "sludge" formed during the fermentation. The resulting fermentation supernatant (typically about 90% to about 98% by weight) is collected for subsequent treatment.

A fermented microbial supernatant contains bio-nutrients, minerals and amino acids. Bio-nutrients are typically present in an amount of from about 0.01% to about 1% of the total weight of fermented microbial supernatant. Each individual bio-nutrient is typically present in an amount of from about 0.00001% to about 0.01% of the total weight of fermented microbial supernatant. Examples of bio-nutrients include, without limitation, biotin, folic acid, glucans like α-glucan and β-glucan, niacin, insotil, pantothenic acid, pyridoxine, riboflavin and thiamine. In aspects of this embodiment, a fermented microbial supernatant disclosed herein comprises, e.g., about 0.00001% to about 0.0011% of biotin, about 0.0006% to about 0.016% of folic acid, about 0.005% to about 15% of niacin, about 0.01% to about 1% of insotil, about 0.00017% to about 0.017% of pantothenic acid, about 0.0006% to about 0.016% of pyrodoxine, about 0.002% to about 0.023% of riboflavin and about 0.001% to about 0.02% of thiamine. In other aspects of this embodiment, a fermented microbial supernatant disclosed herein comprises, e.g., about 0.00006% to about 0.0006% of biotin, about 0.001% to about 0.011% of folic acid, about 0.01% to about 0.1% of niacin, about 0.08% to about 0.18% of insotil, about 0.002% to about 0.012% of pantothenic acid, about 0.001% to about 0.011% of pyrodoxine, about 0.007% to about 0.017% of riboflavin, about 0.003% to about 0.013% of thiamine. In yet other aspects of this embodiment, a fermented microbial supernatant disclosed herein comprises, e.g., about 0.00012% to about 0.0006% of biotin, about 0.001% to about 0.011% of folic acid, about 0.01% to about 0.1% of niacin, about 0.08% to about 0.18% of insotil, about 0.003% to about 0.013% of pantothenic acid, about 0.001% to about 0.011% of pyrodoxine, about 0.008% to about 0.017% of riboflavin, about 0.003% to about 0.013% of thiamine. Instill other aspects of this embodiment, a fermented microbial supernatant disclosed herein comprises, e.g., about 0.00009% to about 0.0003% of biotin, about 0.004% to about 0.008% of folic acid, about 0.03% to about 0.07% of niacin, about 0.11% to about 0.15% of insotil, about 0.006% to about 0.01% of pantothenic acid, about 0.004% to about 0.008% of pyrodoxine, about 0.01% to about 0.014% of riboflavin, about 0.006% to about 0.010% of thiamine.

Minerals are typically present in an amount of from about 0.1% to about 20% of the total weight of fermented microbial supernatant. Each individual mineral is typically present in an amount of from about 0.0001% to about 5% of the total weight of fermented microbial supernatant. Examples of minerals include, without limitation, calcium, chromium, copper, iron, magnesium, phosphate, potassium, sodium and zinc. In aspects of this embodiment, a fermented microbial supernatant disclosed herein comprises, e.g., about 0.02% to about 0.3% of calcium, about 0.000002% to about 0.0016% of chromium, about 0.000009% to about 0.0014% of copper, about 0.00005% to about 0.02% of iron, about 0.001% to about 1.3% of magnesium, about 0.2% to about 14% of phosphate, about 0.4% to about 16% of potassium, about 0.2% to about 15% of sodium and about 0.08% to about 13% of zinc. In other aspects of this embodiment, a fermented microbial supernatant disclosed herein comprises, e.g., about 0.07% to about 0.21% of calcium, about 0.000007% to about 0.0011% of chromium, about 0.00004% to about 0.0009% of copper, about 0.0001% to about 0.015% of iron, about 0.005% to about 0.9% of magnesium, about 0.7% to about 9% of phosphate, about 0.9% to about 11% of potassium, about 0.7% to about 10% of sodium and about 0.3% to about 8% of zinc. In yet other aspects of this embodiment, a fermented microbial supernatant disclosed herein comprises, e.g., about 0.05% to about 1% of calcium, about 0.0001% to about 0.0009% of chromium, about 0.00006% to about 0.0007% of copper, about 0.0001% to about 0.013% of iron, about 0.005% to about 1% of magnesium, about 0.1% to about 7% of phosphate, about 0.5% to about 9% of potassium, about 0.5% to about 8% of sodium and about 0.5% to about 6% of zinc. In still other aspects of this embodiment, a fermented microbial supernatant disclosed herein comprises, e.g., about 0.12% to about 0.16% of calcium, about 0.0002% to about 0.0006% of chromium, about 0.00009% to about 0.0004% of copper, about 0.0006% to about 0.01% of iron, about 0.01% to about 0.4% of magnesium, about 1% to about 4% of phosphate, about 2% to about 6% of potassium, about 1% to about 5% of sodium and about 0.8% to about 3% of zinc.

Amino acids are typically present in an amount of from about 20% to about 60% of the total weight of fermented microbial supernatant. Each individual amino acid is typically present in an amount of from about 0.1% to about 15% of the total weight of fermented microbial supernatant. Examples of minerals include, without limitation, alanine, arginine, aspartic acid, cysteine, glutamic acid, glycine, lysine, methionine, phenylalanine, proline, serine, and threonine. In aspects of this embodiment, a fermented microbial supernatant disclosed herein comprises, e.g., about 0.2% to about 16% of alanine, about 0.09% to about 15% of arginine, about 0.4% to about 18% of aspartic acid, about 0.003% to about 5% of cysteine, about 0.5% to about 20% of glutamic acid, about 0.09% to about 15% of glycine, about 0.09% to about 15% of lysine, about 0.002% to about 5% of methionine, about 0.09% to about 15% of phenylalanine, about 0.09% to about 15% of proline, about 0.09% to about 15% of serine and about 0.09% to about 15% of threonine. In other aspects of this embodiment, a fermented microbial supernatant disclosed herein comprises, e.g., about 0.7% to about 11% of alanine, about 0.5% to about 10% of arginine, about 0.9% to about 13% of aspartic acid, about 0.008% to about 1.2% of cysteine, about 1% to about 15% of glutamic acid, about 0.5% to about 10% of glycine, about 0.8% to about 12% of lysine, about 0.2% to about 1.6% of methionine, about 0.5% to about 10% of phenylalanine, about 0.5% to about 10% of proline, about 0.5% to about 10% of serine and about 0.5% to about 10% of threonine. In yet other aspects of this embodiment, a fermented microbial supernatant disclosed herein comprises, e.g., about 0.5% to about 9% of alanine, about 0.5% to about 8% of arginine, about 1% to about 11% of aspartic acid, about 0.01% to about 2% of cysteine, about 3% to about 13% of glutamic acid, about 0.5% to about 8% of glycine, about 1% to about 10% of lysine, about 0.3% to about 3% of methionine, about 0.5% to about 7% of phenylalanine, about 0.5% to about 7% of proline, about 0.5% to about 7% of serine and about 0.5% to about 7% of threonine. In sill other aspects of this embodiment, a fermented microbial supernatant disclosed herein comprises, e.g., about 2% to about 6% of alanine, about 1% to about 5% of arginine, about 4% to about 8% of aspartic acid, about 0.03% to about 0.7% of cysteine, about 6% to about 10% of glutamic acid, about 1% to about 5% of glycine, about 3% to about 7% of lysine, about 0.7% to about 1.1% of methionine, about 1% to about 5% of phenylalanine, about 1% to about 5% of proline, about 1% to about 5% of serine and about 1% to about 5% of threonine.

Aspects of the present specification disclose, in part, a fermented microbial supernatant that is treated. A treated fermented microbial supernatant is one that is processed in a manner that denatures, kills or otherwise destroys any remaining live microbes, active enzymes contributed by the microbes and malt as well as any other microorganism or enzymes contributed by another source present in a fermented microbial supernatant disclosed herein. Non-limiting examples, of useful treatment procedures include a boiling process using high temperatures, an autoclaving process using high temperatures and high pressure or an irradiation process by exposing the supernatant to ionizing radiation, or any other sterilization process that denatures, kills or otherwise destroys any remaining live yeast, active enzymes contributed by the yeast and malt as well as any other microorganism or enzymes contributed by another source present in a fermented microbial supernatant disclosed herein. Furthermore, the above treatment processes could be used alone, in combination with one another, or in combination with a pasteurization process, a chemical sterilization process and a sterile filtration process to denature, kill or otherwise destroys proteins such as enzymes and microorganisms such as yeast, bacteria and/or mold present the fermentation supernatant disclosed herein. All the methods discussed above are processes known to a person of ordinary skilled in the art as these are routinely used in the food preparation and/or sterilization arts.

The treated fermented microbial supernatant can then be stored in liquid form for subsequent use. Alternatively, the treated fermented microbial supernatant can be processed to create a dried treated fermented microbial supernatant, e.g., by methods known in the art to produce a dry powder. The dry powder form can also be stored for subsequent use. Commercially available dried treated fermented microbial supernatant are produced, including, without limitation, TASTONE® 154, TASTONE® 210 or TASTONE® 900.

Any amount of treated fermented microbial supernatant disclosed herein may be used in a disclosed composition, with the proviso that the amount is useful to practice the methods and uses disclosed herein. Factor used in determining an appropriate amount include, e.g., whether the treated fermented microbial supernatant is in liquid or powder form, the particular commercial source of the treated fermented microbial supernatant, the particular method used to produce the treated fermented microbial supernatant, whether a composition is produced as a concentrate or as a ready as is product, and the dilution factor desired when preparing composition from a concentrate. Typically, a larger amount of a liquid form of the treated fermented microbial supernatant will be required relative to a dry powder form.

In aspects of this embodiment, a liquid composition comprises a treated, fermented yeast supernatant in an amount of, e.g., about 0.5% by weight, about 1.0% by weight, about 1.5% by weight, about 2.0% by weight, about 2.5% by weight, about 3.0% by weight, about 3.5% by weight, about 4.0% by weight, about 4.5% by weight, about 5.0% by weight, about 6.0% by weight, about 7.0% by weight, about 7.5% by weight, about 8.0% by weight, about 9.0% by weight or about 10.0% by weight. In other aspects of this embodiment, a liquid composition comprises a treated, fermented yeast supernatant in an amount of, e.g., at least 0.5% by weight, at least 1.0% by weight, at least 1.5% by weight, at least 2.0% by weight, at least 2.5% by weight, at least 3.0% by weight, at least 3.5% by weight, at least 4.0% by weight, at least 4.5% by weight, at least 5.0% by weight, at least 6.0% by weight, at least 7.0% by weight, at least 7.5% by weight, at least 8.0% by weight, at least 9.0% by weight or at least 10.0% by weight. In yet other aspects of this embodiment, a liquid composition comprises a treated, fermented yeast supernatant in an amount of, e.g., at most 0.5% by weight, at most 1.0% by weight, at most 1.5% by weight, at most 2.0% by weight, at most 2.5% by weight, at most 3.0% by weight, at most 3.5% by weight, at most 4.0% by weight, at most 4.5% by weight, at most 5.0% by weight, at most 6.0% by weight, at most 7.0% by weight, at most 7.5% by weight, at most 8.0% by weight, at most 9.0% by weight or at most 10.0% by weight. In still other aspects of this embodiment, a liquid composition comprises a treated, fermented yeast supernatant in an amount of, e.g., about 0.1% to about 2.5% by weight, about 0.1% to about 3.0% by weight, about 0.1% to about 3.5% by weight, about 0.1% to about 4.0% by weight, about 0.1% to about 5.0% by weight, about 0.5% to about 2.5% by weight, about 0.5% to about 3.0% by weight, about 0.5% to about 3.5% by weight, about 0.5% to about 4.0% by weight, about 0.5% to about 5.0% by weight, about 1% to about 2.5% by weight, about 1% to about 3.0% by weight, about 1% to about 3.5% by weight, about 1% to about 4.0% by weight, about 1% to about 5.0% by weight, about 1% to about 6.0% by weight, about 1% to about 7.0% by weight, about 1% to about 8.0% by weight, about 1% to about 9.0% by weight or about 1% to about 10.0% by weight.

In other aspects of this embodiment, a liquid composition comprises a treated, fermented yeast supernatant in an amount of, e.g., about 15.0% by weight, about 20.0% by weight, about 25.0% by weight, about 30.0% by weight, about 35.0% by weight, about 40.0% by weight, about 45.0% by weight, about 50.0% by weight, about 55.0% by weight, about 60.0% by weight, about 65.0% by weight, about 70.0% by weight, about 75.0% by weight, about 80.0% by weight, about 85.0% by weight or about 90.0% by weight.

In yet other aspects of this embodiment, a liquid composition comprises a treated, fermented yeast supernatant in an amount of, e.g., at least 15.0% by weight, at least 20.0% by weight, at least 25.0% by weight, at least 30.0% by weight, at least 35.0% by weight, at least 40.0% by weight, at least 45.0% by weight, at least 50.0% by weight, at least 55.0% by weight, at least 60.0% by weight, at least 65.0% by weight, at least 70.0% by weight, at least 75.0% by weight, at least 80.0% by weight, at least 85.0% by weight or at least 90.0% by weight. In still other aspects of this embodiment, a liquid composition comprises a treated, fermented yeast supernatant in an amount of, e.g., at most 15.0% by weight, at most 20.0% by weight, at most 25.0% by weight, at most 30.0% by weight, at most 35.0% by weight, at most 40.0% by weight, at most 45.0% by weight, at most 50.0% by weight, at most 55.0% by weight, at most 60.0% by weight, at most 65.0% by weight, at most 70.0% by weight, at most 75.0% by weight, at most 80.0% by weight, at most 85.0% by weight or at most 90.0% by weight.

In other aspects of this embodiment, a liquid composition comprises a treated, fermented yeast supernatant in an amount of, e.g., about 5% to about 7.5% by weight, about 5% to about 10% by weight, about 5% to about 15% by weight, about 5% to about 20% by weight, about 5% to about 25% by weight, about 5% to about 30% by weight, about 5% to about 35% by weight, about 5% to about 40% by weight, about 5% to about 45% by weight, about 5% to about 50% by weight, about 5% to about 55% by weight, about 5% to about 60% by weight, about 5% to about 65% by weight, about 5% to about 70% by weight, about 5% to about 75% by weight, about 5% to about 80% by weight, about 5% to about 85% by weight, about 5% to about 90% by weight, about 5% to about 95% by weight, about 10% to about 15% by weight, about 10% to about 20% by weight, about 10% to about 25% by weight, about 10% to about 30% by weight, about 10% to about 35% by weight, about 10% to about 40% by weight, about 10% to about 45% by weight, about 10% to about 50% by weight, about 10% to about 55% by weight, about 10% to about 60% by weight, about 10% to about 65% by weight, about 10% to about 70% by weight, about 10% to about 75% by weight, about 10% to about 80% by weight, about 10% to about 85% by weight, about 10% to about 90% by weight, about 10% to about 95% by weight, about 15% to about 20% by weight, about 15% to about 25% by weight, about 15% to about 30% by weight, about 15% to about 35% by weight, about 15% to about 40% by weight, about 15% to about 45% by weight, about 15% to about 50% by weight, about 15% to about 55% by weight, about 15% to about 60% by weight, about 15% to about 65% by weight, about 15% to about 70% by weight, about 15% to about 75% by weight, about 15% to about 80% by weight, about 15% to about 85% by weight, about 15% to about 90% by weight, about 15% to about 95% by weight, about 25% to about 25% by weight, about 25% to about 30% by weight, about 25% to about 35% by weight, about 25% to about 40% by weight, about 25% to about 45% by weight, about 25% to about 50% by weight, about 25% to about 55% by weight, about 25% to about 60% by weight, about 25% to about 65% by weight, about 25% to about 70% by weight, about 25% to about 75% by weight, about 25% to about 80% by weight, about 25% to about 85% by weight, about 25% to about 90% by weight, about 25% to about 95% by weight, about 25% to about 30% by weight, about 25% to about 35% by weight, about 25% to about 40% by weight, about 25% to about 45% by weight, about 25% to about 50% by weight, about 25% to about 55% by weight, about 25% to about 60% by weight, about 25% to about 65% by weight, about 25% to about 70% by weight, about 25% to about 75% by weight, about 25% to about 80% by weight, about 25% to about 85% by weight, about 25% to about 90% by weight, about 25% to about 95% by weight, about 30% to about 35% by weight, about 30% to about 40% by weight, about 30% to about 45% by weight, about 30% to about 50% by weight, about 30% to about 55% by weight, about 30% to about 60% by weight, about 30% to about 65% by weight, about 30% to about 70% by weight, about 30% to about 75% by weight, about 30% to about 80% by weight, about 30% to about 85% by weight, about 30% to about 90% by weight, about 30% to about 95% by weight, about 35% to about 40% by weight, about 35% to about 45% by weight, about 35% to about 50% by weight, about 35% to about 55% by weight, about 35% to about 60% by weight, about 35% to about 65% by weight, about 35% to about 70% by weight, about 35% to about 75% by weight, about 35% to about 80% by weight, about 35% to about 85% by weight, about 35% to about 90% by weight, about 35% to about 95% by weight, about 40% to about 45% by weight, about 40% to about 50% by weight, about 40% to about 55% by weight, about 40% to about 60% by weight, about 40% to about 65% by weight, about 40% to about 70% by weight, about 40% to about 75% by weight, about 40% to about 80% by weight, about 40% to about 85% by weight, about 40% to about 90% by weight, about 40% to about 95% by weight, about 45% to about 50% by weight, about 45% to about 55% by weight, about 45% to about 60% by weight, about 45% to about 65% by weight, about 45% to about 70% by weight, about 45% to about 75% by weight, about 45% to about 80% by weight, about 45% to about 85% by weight, about 45% to about 90% by weight, about 45% to about 95% by weight, about 50% to about 55% by weight, about 50% to about 60% by weight, about 50% to about 65% by weight, about 50% to about 70% by weight, about 50% to about 75% by weight, about 50% to about 80% by weight, about 50% to about 85% by weight, about 50% to about 90% by weight, about 50% to about 95% by weight, about 55% to about 60% by weight, about 55% to about 65% by weight, about 55% to about 70% by weight, about 55% to about 75% by weight, about 55% to about 80% by weight, about 55% to about 85% by weight, about 55% to about 90% by weight, about 55% to about 95% by weight, about 60% to about 65% by weight, about 60% to about 70% by weight, about 60% to about 75% by weight, about 60% to about 80% by weight, about 60% to about 85% by weight, about 60% to about 90% by weight, about 60% to about 95% by weight, about 65% to about 70% by weight, about 65% to about 75% by weight, about 65% to about 80% by weight, about 65% to about 85% by weight, about 65% to about 90% by weight, about 65% to about 95% by weight, about 70% to about 75% by weight, about 70% to about 80% by weight, about 70% to about 85% by weight, about 70% to about 90% by weight, about 70% to about 95% by weight, about 75% to about 80% by weight, about 75% to about 85% by weight, about 75% to about 90% by weight, about 75% to about 95% by weight, about 80% to about 85% by weight, about 80% to about 90% by weight, about 80% to about 95% by weight, about 85% to about 90% by weight, about 85% to about 95% by weight or about 90% to about 95% by weight.

Any amount of dried treated fermented microbial supernatant disclosed herein may be used in a dry powdered composition disclosed herein, with the proviso that the amount is useful to practice the methods and uses disclosed herein. In some embodiments, a dry powdered composition disclosed herein comprises about 5% to about 15% by weight of dried treated fermented microbial supernatant. In aspects of these embodiments, a dry powdered composition comprises a dried treated, fermented yeast supernatant in an amount of, e.g., about 5.0% by weight, about 6.0% by weight, about 7.0% by weight, about 7.5% by weight, about 8.0% by weight, about 9.0% by weight, about 10.0% by weight, about 11.0% by weight, about 12.0% by weight, about 13.0% by weight, about 14.0% by weight or about 15.0% by weight. In other aspects of these embodiments, a dry powdered composition comprises a dried treated, fermented yeast supernatant in an amount of, e.g., at least 5.0% by weight, at least 6.0% by weight, at least 7.0% by weight, at least 7.5% by weight, at least 8.0% by weight, at least 9.0% by weight, at least 10.0% by weight, at least 11.0% by weight, at least 12.0% by weight, at least 13.0% by weight, at least 14% by weight or at least 15.0% by weight. In yet other aspects of these embodiments, a dry powdered composition comprises a dried treated, fermented yeast supernatant in an amount of, e.g., at most 5.0% by weight, at most 6.0% by weight, at most 7.0% by weight, at most 8% by weight, at most 9.0% by weight, at most 10.0% by weight or at most 11.0% by weight, at most 12.0% by weight, at most 13.0% by weight, at most 14% by weight or at most 15% by weight. In still other aspects of these embodiments, a dry powdered composition comprises a dried treated, fermented yeast supernatant in an amount of, e.g., about 5.0% to about 15.0% by weight, about 6.0% to about 14.0% by weight, about 7.0% to about 13.0% by weight, about 8.0% to about 12.0% by weight, about 8.5% to about 11.0% by weight, about 9.0% to about 10.0% by weight, about 9.1% to about 9.7% by weight or about 9.2% to about 9.5% by weight or about 9.2% by weight.

In still other aspects of these embodiments, a dry powdered composition comprises a dried treated, fermented yeast supernatant in an amount of, e.g., about 5.0% to about 6.0% by weight, about 5.0% to about 7.0% by weight, about 5.0% to about 8.0% by weight, about 5.0% to about 9.0% by weight, about 5.0% to about 10.0% by weight, about 5.0% to about 11.0% by weight, about 5.0% to about 12.0% by weight, about 5.0% to about 13.0% by weight, about 5.0% to about 14.0% by weight, about 5.0% to about 15.0% by weight, about 6.0% to about 7.0% by weight, about 6.0% to about 8.0% by weight, about 6.0% to about 9.0% by weight, about 6.0% to about 10.0% by weight, about 6.0% to about 11.0% by weight, about 6.0% to about 12.0% by weight, about 6.0% to about 13.0% by weight, about 6.0% to about 14.0% by weight, about 6.0% to about 15.0% by weight, about 7.0% to about 8.0% by weight, about 7.0% to about 9.0% by weight, about 7.0% to about 10.0% by weight, about 7.0% to about 11.0% by weight, 7.0% to about 12.0% by weight, about 7.0% to about 13.0% by weight, about 7.0% to about 14.0% by weight, about 7.0% to about 15.0% by weight, about 8.0% to about 9.0% by weight, about 8.0% to about 10.0% by weight, about 8.0% to about 11.0% by weight, 8.0% to about 12.0% by weight, about 8.0% to about 13.0% by weight, about 8.0% to about 14.0% by weight, about 8.0% to about 15.0% by weight, about 9.0% to about 10.0% by weight, about 9.0% to about 11.0% by weight, 9.0% to about 12.0% by weight, about 9.0% to about 13.0% by weight, about 9.0% to about 14.0% by weight, about 9.0% to about 15.0% by weight, about 10.0% to about 11.0% by weight, about 11.0% to about 12.0% by weight, about 11.0% to about 13.0% by weight, about 11.0% to about 14.0% by weight, about 11.0% to about 15.0% by weight, about 12.0% to about 13.0% by weight, about 12.0% to about 14.0% by weight, about 12.0% to about 15.0% by weight, about 13.0% to about 14.0% by weight, about 13.0% to about 15.0% by weight, or about 14.0% to about 15.0% by weight.

Aspects of the present specification disclose, in part, a surfactant. Surfactants are compounds that lower the surface tension of a liquid, allowing easier spreading, and lowering of the interfacial tension between two liquids, or between a liquid and a solid. Either a single surfactant may be mixed with the composition disclosed herein, or a plurality of surfactants may be mixed with a composition disclosed herein. Useful surfactants include, without limitation, ionic surfactants, zwitterionic (amphoteric) surfactants, non-ionic surfactants, or any combination therein.

Ionic surfactants include anionic surfactants. Anionic surfactants include ones based on permanent functional groups attached to the head, such as, e.g., sulfate, sulfonate, phosphate carboxylates) or pH dependent anionic surfactants. Anionic surfactants include, without limitation, alkane sulfonates like sodium caprylyl sulfonate (BIO-TERGE® PAS-85), alkyl sulfates like ammonium lauryl sulfate and sodium lauryl sulfate (SDS); alkyl ether sulfates like sodium laureth sulfate and sodium myreth sulfate; docusates like dioctyl sodium sulfosuccinate; sulfonate fluorosurfactants like perfluorooctanesulfonate (PFOS) and perfluorobutanesulfonate; alkyldiphenyloxide Disulfonates like DOW-FAX™ 2A1 (Disodium Lauryl Phenyl Ether Disulfonate), DOWFAX™ 3B2 (Disodium Decyl Phenyl Ether Disulfonate), DOWFAX™ C10L (Disodium Decyl Phenyl Ether Disulfonate), DOWFAX™ 2EP, and DOWFAX™ 8390 (Disodium Cetyl Phenyl Ether Disulfonate); potassium phosphate polyether esters like TRITON™ H-55 and TRITON™ H-66; alkyl benzene sulfonates; alkyl aryl ether phosphates; alkyl ether phosphates; alkyl carboxylates like fatty acid salts and sodium stearate; sodium lauroyl sarcosinate; carboxylate fluorosurfactants like perfluorononanoate and perfluorooctanoate; and Sodium Hexyldiphenyl Ether Sulfonate (DOWFAX™ C6L).

Ionic surfactants also include cationic surfactants. Cationic surfactants include ones based on permanent or pH dependent cationic surfactants, such as, e.g., primary, secondary or tertiary amines. Cationic surfactants include, without limitation, alkyltrimethylammonium salts like cetyl trimethylammonium bromide (CTAB) and cetyl trimethylammonium chloride (CTAC); cetylpyridinium chloride (CPC); polyethoxylated tallow amine (POEA); benzalkonium chloride (BAC); benzethonium chloride (BZT); 5-Bromo-5-nitro-1,3-dioxane; dimethyldioctadecylammonium chloride; and dioctadecyldimethylammonium bromide (DODAB), as well as pH-dependent primary, secondary or tertiary amines like surfactants where the primary amines become positively charged at pH greater than 10, or the secondary amines become charged at pH less than 4, like octenidine dihydrochloride. Other useful anionic surfactants include bio-based anionic surfactants, including, without limitation, STEPONOL® AM 30-KE, an ammonium lauryl sulfate, and STEPONOL® EHS, a sodium 2-ethyl hexyl sulfate. Such bio-based surfactants are not synthetic molecules, but instead are anionic biosurfactants derived from organic matter such as plants.

Zwitterionic surfactants are based on primary, secondary or tertiary amines or quaternary ammonium cation with a sulfonate, a carboxylate, or a phosphate. Zwitterionic surfactants include, without limitation, 3-[(3-Cholamidopropyl)dimethylammonio]-1-propanesulfonate (CHAPS); sultaines like cocamidopropyl hydroxysultaine; betaines like cocamidopropyl betaine; or lecithins.

Non-ionic surfactants are less denaturing and as such are useful to solubilize membrane proteins and lipids while retaining protein-protein interactions. Nonionic surfactants include polyether nonionic surfactants, polyhydroxyl nonionic surfactants and biosurfactants. Nonionic surfactants include alcohol ethoxylates, alkylphenol ethoxylates, phenol ethoxylates, amide ethoxylates, glyceride ethoxylates, fatty acid ethoxylates, fatty amine ethoxylates, and alkene amides. A nonionic surfactant disclosed herein may have the general formula of $H(OCH_2CH_2)_xOC_6H_4R^1$, $H(OCH_2CH_2)_xOR^2$, or $H(OCH_2CH_2)_xOC(O)R^2$, wherein x represents the number of moles of ethylene oxide added to an alkyl phenol and/or a fatty alcohol or a fatty acid, $R^1$ represents a long chain alkyl group and, $R^2$ represents a long chain aliphatic group. In aspects of this embodiment, $R^1$ is a $C_7$-$C_{10}$ alkyl group and/or $R^2$ is a $C_{12}$-$C_{20}$ aliphatic group.

Non-limiting examples of non-ionic surfactants include polyoxyethylene glycol sorbitan alkyl esters (or ethoxylated sorbital esters) like polysorbate 20 sorbitan monooleate (TWEEN® 20), polysorbate 40 sorbitan monooleate (TWEEN® 40), polysorbate 60 sorbitan monooleate (TWEEN® 60), polysorbate 61 sorbitan monooleate (TWEEN® 61), polysorbate 65 sorbitan monooleate (TWEEN® 65), polysorbate 80 sorbitan monooleate (TWEEN® 80), polysorbate 81 sorbitan monooleate (TWEEN® 81) and polysorbate 85 sorbitan monooleate (TWEEN® 85); sorbital esters like sorbitan monooleate, sorbitan monolaurate, sorbitan monopalmitate, sorbitan monostearate and sorbitan tristearate; polyglycerol esters like glycerol monooleate, glycerol monolaurate, glycerol monopalmitate, glycerol monostearate, glycerol trioleate, glycerol ricinoleate, glycerol tristearate, mono diglycerides and glycerol triacetate; ethoxylated polyglycerol esters; alkyl glucosides like arachidyl glucoside, $C_{12-20}$ alkyl glucoside, caprylyl/capryl glucoside, cetearyl glucoside, cocoglucoside, ethyl glucoside and lauryl glucoside. decyl glucoside; ethoxylated alkyl glucosides; sucrose esters like sucrose monooleate, sucrose monolaurate, sucrose monopalmitate, sucrose monostearate, sucrose trioleate, sucrose ricinoleate, sucrose tristearate, sucrose diglycerides and sucrose triacetate; ethoxylated sucrose ester; amine oxides; ethoxylated alcohols; ethoxylated aliphatic alcohols; alkylamines; ethoxylated alkylamines; ethoxylated alkyl phenols like ethoxylated nonyl phenol and ethoxylated octyl phenol; alkyl polysaccharides; ethoxylated alkyl polysaccharides; ethoxylated fatty acids like ethoxylated castor oil; ethoxylated fatty alcohols like ethoxylated ceto-oleyl alcohol, ethoxylated ceto-stearyl alcohol, ethoxylated decyl alcohol, ethoxylated dodecyl alcohol and ethoxylated tridecyl alcohol; ethoxylated fatty amines; poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), and Poloxamer 407 (PLURONIC® F127); linear secondary alcohol ethoxylates like TERGITOL™ 15-S-5, TERGITOL™ 15-S-7, TERGITOL™ 15-S-9, TERGITOL™ 15-S-12, TERGITOL™ 15-S-15, TERGITOL™ 15-S-20, TERGITOL™ 15-S-30 and TERGITOL™ 15-S-40; $C_{2-20}$ alkene di-substituted amides like STEPOSOL® MET-10U; alkyl phenol polyglycol ethers; polyethylene glycol alkyl aryl ethers; polyoxyethylene glycol alkyl ethers, like octaethylene glycol monododecyl ether, pentaethylene glycol monododecyl ether, BRIJ® 30, and BRIJ® 35; 2-dodecoxyethanol (LUBROL®-PX); polyoxyethylene glycol octylphenol ethers like polyoxyethylene (4-5) p-t-octyl phenol (TRITON® X-45) and polyoxyethylene octyl phenyl ether (TRITON® X-100); polyoxyethylene glycol alkylphenol ethers like Nonoxynol-9; phenoxypolyethoxylethanols like nonylphenoxypolyethoxylethanol and octylphenoxypolyethoxyethanol (IGEPAL® CA-630 or NONIDET™ P-40); glucoside alkyl ethers like octyl glucopyranoside; maltoside alkyl ethers like dodecyl maltopyranoside; thioglycoside alkyl ethers like heptyl thioglucopyranoside; digitonins; glycerol alkyl esters like glyceryl laurate; alkyl aryl polyether sulfates; alcohol sulfonates; sorbitan alkyl esters; cocamide ethanolamines like cocamide monoethanolamine and cocamide diethanolamine; sucrose monolaurate; dodecyl dimethylamine oxide, and sodium cholate.

Other useful non-ionic surfactants include non-ionic biosurfactants. Such bio-based surfactants are not synthetic molecules, but instead are non-ionic biosurfactants derived from organic matter such as plants. Exemplary nonionic biosurfactants include saponins. Found throughout the plant kingdom, saponins are a diverse group of amphipathic glycosides having one or more hydrophilic glycoside moieties combined with a lipophilic triterpene (triterpenoid saponins) or steroid aglycone (steroidal saponins or steroid glycosides) backbone called a sapogenin. A triterpenoid saponin includes, without limitation, a tetracyclic triterpenoid saponin and a pentacyclic triterpenoid saponin. Non-limiting examples of a tetracyclic triterpenoid saponin include a cucurbitane, a cycloartane, a cycloartenol, a dammarane, a euphane, a lanostane and a tirucallane. Non-limiting examples of a pentacyclic triterpenoid saponin include an enoxolone, a hederagenin, a hopane, a lupane, a maslinic acid, an oleanane, an ursane, and a taraxasterane. Non-limiting examples of a steroidal saponin include a diosgenin, an eleutheroside, a ginsenoside, a sarsasapogenin, and a yamogenin. Soap bark tree (*Quillaja saponaria*), fenugreek (*Trigonella foenum-graceum*), alfalfa (*Medicago sativa*), horse chestnut (*Aesculus hippocastanum*), licorice (*Glycyrrhiza* species such as *Glycyrrhiza glabra*), soapwort (*Saponaria officinaux*), Mojave Yucca (*Yucca schidigera*), *Gypsophila* genus (such as *Gypsophila paniculata*), sarsaparilla (*Smilax regelii* and other closely related species of *Smilax* genus) and ginseng (*Panax* genus) are the main plant sources of saponins used in health and industrial applications. Additional examples of saponins are described in Güçlü-Üstündağ and Mazza, Saponins: Properties, Applications and Processing. 2007 Crit. Rev. Food Sci. Nutr. 47(3): 231-58 (2007); Kregiel, et al., Saponin-Based, Biological-Active Surfactants from Plants, In Application and characterization of surfactants, pp. 183-205 (InTech, 2017), each of which is hereby incorporated by reference in its entirety.

Saponins useful for the disclosed dry powdered compositions are commercially manufactured and available, including, without limitation, Yucca SD Powder, a *Yucca schidigera* saponin extract (Desert King International, San Diego, California, USA), Yucca Ag-Aide Powder, a *Yucca schidigera* saponin extract (Desert King International, San Diego, California, USA), Quillaja Extract Powder, a *Quillaja saponaria* saponin extract (Garuda International Inc., Exeter, California, USA), Quillaja Powder QP 100%, a *Quillaja saponaria* saponin extract (Desert King International, San Diego, California, USA), Quillaja Dry 100 NP, a *Quillaja saponaria* saponin extract (Desert King International, San Diego, California, USA), and QL Agri 100%, a *Quillaja saponaria* saponin extract (Desert King International, San Diego, California, USA).

Non-ionic surfactants act synergistically to enhance the action of the treated fermented microbial supernatant. In addition, it has been established that the non-ionic surfactants used in a composition disclosed herein are compatible with enhance chemical reactions.

In some embodiments, a liquid composition disclosed herein comprises one or more nonionic surfactants. In aspects of these embodiments, a liquid composition disclosed herein comprises, e.g., two or more non-ionic surfactants, three or more non-ionic surfactants, four or more non-ionic surfactants, or five or more non-ionic surfactants. In other aspects of these embodiments, a liquid composition disclosed herein comprises, e.g., two non-ionic surfactants, three non-ionic surfactants, four non-ionic surfactants, or five non-ionic surfactants.

In some embodiments, a liquid composition disclosed herein comprises one or more nonionic biosurfactants. In aspects of these embodiments, a liquid composition disclosed herein comprises, e.g., two or more non-ionic biosurfactants, three or more non-ionic biosurfactants, four or more non-ionic biosurfactants, or five or more non-ionic biosurfactants. In other aspects of these embodiments, a liquid composition disclosed herein comprises, e.g., two non-ionic biosurfactants, three non-ionic biosurfactants, four non-ionic biosurfactants, or five non-ionic biosurfactants.

In some embodiments, a liquid composition disclosed herein comprises one or more nonionic saponins. In aspects of these embodiments, a liquid composition disclosed herein comprises, e.g., two or more non-ionic saponins, three or more non-ionic saponins, four or more non-ionic saponins, or five or more non-ionic saponins. In other aspects of these embodiments, a liquid composition disclosed herein comprises, e.g., two non-ionic saponins, three non-ionic saponins, four non-ionic saponins, or dried non-ionic saponins.

In some embodiments, a dry powdered composition disclosed herein comprises one or more dried nonionic surfactants. In aspects of these embodiments, a dry powdered composition disclosed herein comprises, e.g., two or more dried non-ionic surfactants, three or more dried non-ionic surfactants, four or more dried non-ionic surfactants, or five or more dried non-ionic surfactants. In other aspects of these embodiments, a dry powdered composition disclosed herein comprises, e.g., two dried non-ionic surfactants, three dried non-ionic surfactants, four dried non-ionic surfactants, or five dried non-ionic surfactants.

In some embodiments, a dry powdered composition disclosed herein comprises one or more nonionic biosurfactants. In aspects of these embodiments, a dry powdered composition disclosed herein comprises, e.g., two or more dried non-ionic biosurfactants, three or more dried non-ionic biosurfactants, four or more dried non-ionic biosurfactants, or five or more dried non-ionic biosurfactants. In other aspects of these embodiments, a dry powdered composition disclosed herein comprises, e.g., two dried non-ionic biosurfactants, three dried non-ionic biosurfactants, four dried non-ionic biosurfactants, or five dried non-ionic biosurfactants.

In some embodiments, a dry powdered composition disclosed herein comprises one or more dried nonionic saponins. In aspects of these embodiments, a dry powdered composition disclosed herein comprises, e.g., two or more dried non-ionic saponins, three or more dried non-ionic saponins, four or more dried non-ionic saponins, or five or more dried non-ionic saponins. In other aspects of these embodiments, a dry powdered composition disclosed herein comprises, e.g., two dried non-ionic saponins, three dried non-ionic saponins, four dried non-ionic saponins, or five dried non-ionic saponins.

In embodiment, a composition disclosed herein contains one or more nonionic surfactants but no ionic surfactants or zwitterionic (amphoteic) surfactants. In another embodiment, a composition disclosed herein contains one or more nonionic surfactants and one or more anionic surfactants. In another embodiment, a composition disclosed herein does not contain any cationic surfactants. In another embodiment, a composition disclosed herein does not contain any cationic surfactants or zwitterionic surfactants. In another embodiment, a composition disclosed herein does not contain any ionic surfactants. In another embodiment, a composition disclosed herein does not contain any ionic surfactants or zwitterionic surfactants.

Any amount of non-ionic surfactant disclosed herein may be used in a liquid composition disclosed herein, with the proviso that the amount is useful to practice the methods and uses disclosed herein. In some embodiments, a liquid composition disclosed herein comprises, e.g., about 1% to about 25% by weight of one or more non-ionic surfactants.

In aspects of this embodiment, a liquid composition comprises one or more non-ionic surfactants in an amount of, e.g., about 0.01% by weight, about 0.05% by weight, about 0.075% by weight, about 0.1% by weight, about 0.2% by weight, about 0.3% by weight, about 0.4% by weight, about 0.5% by weight, about 0.6% by weight, about 0.7% by weight, about 0.8% by weight, about 0.9% by weight, about 1.0% by weight, about 1.5% by weight, about 2.0% by weight, about 2.5% by weight, about 3.0% by weight, about 4.0% by weight, about 5.0% by weight, about 6.0% by weight, about 7.0% by weight, about 7.5% by weight, about 8.0% by weight, about 9.0% by weight, about 10.0% by weight, about 11.0% by weight, about 12.0% by weight, about 13.0% by weight, about 14.0% by weight, about 15.0% by weight, about 16.0% by weight, about 17.0% by weight, about 18.0% by weight, about 19.0% by weight, or about 20.0% by weight. In other aspects of this embodiment, a liquid composition comprises one or more non-ionic surfactants in an amount of, e.g., at least 0.01% by weight, at least 0.05% by weight, at least 0.075% by weight, at least 0.1% by weight, at least 0.25% by weight, at least 0.5% by weight, at least 0.75% by weight, at least 1.0% by weight, at least 1.5% by weight, at least 2.0% by weight, at least 2.5% by weight, at least 3.0% by weight, at least 4.0% by weight, at least 5.0% by weight, at least 6.0% by weight, at least 7.0% by weight, at least 7.5% by weight, at least 8.0% by weight, at least 9.0% by weight, at least 10.0% by weight, at least 11.0% by weight, at least 12.0% by weight, at least 13.0% by weight, at least 14.0% by weight, at least 15.0% by weight, at least 16.0% by weight, at least 17.0% by weight, at least 18.0% by weight, at least 19.0% by weight, or at least 20.0% by weight. In yet other aspects of this embodiment, a liquid composition comprises one or more non-ionic surfactants in an amount of, e.g., at most 0.01% by weight, at most 0.05% by weight, at most 0.075% by weight, at most 0.1% by weight, at most 0.25% by weight, at most 0.5% by weight, at most 0.75% by weight, at most 1.0% by weight, at most 1.5% by weight, at most 2.0% by weight, at most 2.5% by weight, at most 3.0% by weight, at most 4.0% by weight, at most 5.0% by weight, at most 6.0% by weight, at most 7.5% by weight, at most 8.0% by weight, at most 9.0% by weight, at most 10.0% by weight, at most 11.0% by weight, at most 12.0% by weight, at most 13.0% by weight, at most 14.0% by weight, at most 15.0% by weight, at most 16.0% by weight, at most 17.0% by weight, at most 18.0% by weight, at most 19.0% by weight, or at most 20.0% by weight In still other aspects of this embodiment, a liquid composition comprises one or more non-ionic surfactants in an amount of, e.g., about 0.1% by weight to about 0.5% by weight, about 0.1% by weight to about 0.75% by weight, about 0.1% by weight to about 1.0% by weight, about 0.1% by weight to about 1.5% by weight, about 0.1% by weight to about 2.0% by weight, about 0.1% by weight to about 2.5% by weight, about 0.2% by weight to about 0.5% by weight, about 0.2% by weight to about 0.75% by weight, about 0.2% by weight to about 1.0% by weight, about 0.2% by weight to about 1.5% by weight, about 0.2% by weight to about 2.0% by weight, about 0.2% by weight to about 2.5% by weight, about 0.5% by weight to about 1.0% by weight, about 0.5% by weight to about 1.5% by weight, about 0.5% by weight to about 2.0% by weight, about 0.5% by weight to about 2.5% by weight, about 0.5% by weight to about 3.0% by weight, about 0.5% by weight to about 4.0% by weight, about 0.5% by weight to about 5.0% by weight, about 1.0% by weight to about 2.5% by weight, about 1.0% by weight to about 3.0% by weight, about 1.0% by weight to about 4.0% by weight, about 1.0% by weight to about 5.0% by weight, about 1.0% by weight to about 6.0% by weight, about 1.0% by weight to about 7.0% by weight, about 1.0% by weight to about 7.5% by weight, about 1.0% by weight to about 8.0% by weight, about 1.0% by weight to about 9.0% by weight, about 1.0% by weight to about 10.0% by weight, about 2.0% by weight to about 2.5% by weight, about 2.0% by weight to about 3.0% by weight, about 2.0% by weight to about 4.0% by weight, about 2.0% by weight to about 5.0% by weight, about 2.0% by weight to about 6.0% by weight, about 2.0% by weight to about 7.0% by weight, about 2.0% by weight to about 7.5% by weight, about 2.0% by weight to about 8.0% by weight, about 2.0% by weight to about 9.0% by weight, about 2.0% by weight to about 10.0% by weight, about 5.0% by weight to about 6.0% by weight, about 5.0% by weight to about 7.0% by weight, about 5.0% by weight to about 7.5% by weight, about 5.0% by weight to about 8.0% by weight, about 5.0% by weight to about 9.0% by weight, about 5.0% by weight to about 10.0% by weight, about 5.0% by weight to about 11.0% by weight, about 5.0% by weight to about 12.0% by weight, about 5.0% by weight to about 13.0% by weight, about 5.0% by weight to about 14.0% by weight, about 5.0% by weight to about 15.0% by weight, about 5.0% by weight to about 20.0% by weight, or about 5.0% by weight to about 25.0% by weight, about 10.0% by weight to about 15.0% by weight, about 10.0% by weight to about 20.0% by weight, or about 10.0% by weight to about 25.0% by weight, about 15.0% by weight to about 20.0% by weight, or about 15.0% by weight to about 25.0% by weight, or about 20.0% by weight to about 25.0% by weight.

In aspects of this embodiment, a liquid composition comprises one or more non-ionic biosurfactants in an amount of, e.g., about 0.01% by weight, about 0.05% by weight, about 0.075% by weight, about 0.1% by weight, about 0.2% by weight, about 0.3% by weight, about 0.4% by weight, about 0.5% by weight, about 0.6% by weight, about 0.7% by weight, about 0.8% by weight, about 0.9% by weight, about 1.0% by weight, about 1.5% by weight, about 2.0% by weight, about 2.5% by weight, about 3.0% by weight, about 4.0% by weight, about 5.0% by weight, about 6.0% by weight, about 7.0% by weight, about 7.5% by weight, about 8.0% by weight, about 9.0% by weight, about 10.0% by weight, about 11.0% by weight, about 12.0% by weight, about 13.0% by weight, about 14.0% by weight, about 15.0% by weight, about 16.0% by weight, about 17.0% by weight, about 18.0% by weight, about 19.0% by weight, or about 20.0% by weight. In other aspects of this embodiment, a liquid composition comprises one or more non-ionic biosurfactants in an amount of, e.g., at least 0.01% by weight, at least 0.05% by weight, at least 0.075% by weight, at least 0.1% by weight, at least 0.25% by weight, at least 0.5% by weight, at least 0.75% by weight, at least 1.0% by weight, at least 1.5% by weight, at least 2.0% by weight, at least 2.5% by weight, at least 3.0% by weight, at least 4.0% by weight, at least 5.0% by weight, at least 6.0% by weight, at least 7.0% by weight, at least 7.5% by weight, at least 8.0% by weight, at least 9.0% by weight, at least 10.0% by weight, at least 11.0% by weight, at least 12.0% by weight, at least 13.0% by weight, at least 14.0% by weight, at least 15.0% by weight, at least 16.0% by weight, at least 17.0% by weight, at least 18.0% by weight, at least 19.0% by weight, or at least 20.0% by weight. In yet other aspects of this embodiment, a liquid composition comprises one or more non-ionic biosurfactants in an amount of, e.g., at most 0.01% by weight, at most 0.05% by weight, at most 0.075% by weight, at most 0.1% by weight, at most 0.25% by weight, at most 0.5% by weight, at most 0.75% by weight, at most 1.0% by weight, at most 1.5% by weight, at most 2.0% by weight, at most 2.5% by weight, at most 3.0% by weight, at most 4.0% by weight, at most 5.0% by weight, at most 6.0% by weight, at most 7.5% by weight, at most 8.0% by weight, at most 9.0% by weight, at most 10.0% by weight, at most 11.0% by weight, at most 12.0% by weight, at most 13.0% by weight, at most 14.0% by weight, at most 15.0% by weight, at most 16.0% by weight, at most 17.0% by weight, at most 18.0% by weight, at most 19.0% by weight, or at most 20.0% by weight In still other aspects of this embodiment, a liquid composition comprises one or more non-ionic biosurfactants in an amount of, e.g., about 0.1% by weight to about 0.5% by weight, about 0.1% by weight to about 0.75% by weight, about 0.1% by weight to about 1.0% by weight, about 0.1% by weight to about 1.5% by weight, about 0.1% by weight to about 2.0% by weight, about 0.1% by weight to about 2.5% by weight, about 0.2% by weight to about 0.5% by weight, about 0.2% by weight to about 0.75% by weight, about 0.2% by weight to about 1.0% by weight, about 0.2% by weight to about 1.5% by weight, about 0.2% by weight to about 2.0% by weight, about 0.2% by weight to about 2.5% by weight, about 0.5% by weight to about 1.0% by weight, about 0.5% by weight to about 1.5% by weight, about 0.5% by weight to about 2.0% by weight, about 0.5% by weight to about 2.5% by weight, about 0.5% by weight to about 3.0% by weight, about 0.5% by weight to about 4.0% by weight, about 0.5% by weight to about 5.0% by weight, about 1.0% by weight to about 2.5% by weight, about 1.0% by weight to about 3.0% by weight, about 1.0% by weight to about 4.0% by weight, about 1.0% by weight to about 5.0% by weight, about 1.0% by weight to about 6.0% by weight, about 1.0% by weight to about 7.0% by weight, about 1.0% by weight to about 7.5% by weight, about 1.0% by weight to about 8.0% by weight, about 1.0% by weight to about 9.0% by weight, about 1.0% by weight to about 10.0% by weight, about 2.0% by weight to about 2.5% by weight, about 2.0% by weight to about 3.0% by weight, about 2.0% by weight to about 4.0% by weight, about 2.0% by weight to about 5.0% by weight, about 2.0% by weight to about 6.0% by weight, about 2.0% by weight to about 7.0% by weight, about 2.0% by weight to about 7.5% by weight, about 2.0% by weight to about 8.0% by weight, about 2.0% by weight to about 9.0% by weight, about 2.0% by weight to about 10.0% by weight, about 5.0% by weight to about 6.0% by weight, about 5.0% by weight to about 7.0% by weight, about 5.0% by weight to about 7.5% by weight, about 5.0% by weight to about 8.0% by weight, about 5.0% by weight to about 9.0% by weight, about 5.0% by weight to about 10.0% by weight, about 5.0% by weight to about 11.0% by weight, about 5.0% by weight to about 12.0% by weight, about 5.0% by weight to about 13.0% by weight, about 5.0% by weight to about 14.0% by weight, about 5.0% by weight to about 15.0% by weight, about 5.0% by weight to about 20.0% by weight, or about 5.0% by weight to about 25.0% by weight, about 10.0% by weight to about 15.0% by weight, about 10.0% by weight to about 20.0% by weight, or about 10.0% by weight to about 25.0% by weight, about 15.0% by weight to about 20.0% by weight, or about 15.0% by weight to about 25.0% by weight, or about 20.0% by weight to about 25.0% by weight.

In aspects of this embodiment, a liquid composition comprises one or more non-ionic saponins in an amount of, e.g., about 0.01% by weight, about 0.05% by weight, about 0.075% by weight, about 0.1% by weight, about 0.2% by weight, about 0.3% by weight, about 0.4% by weight, about 0.5% by weight, about 0.6% by weight, about 0.7% by weight, about 0.8% by weight, about 0.9% by weight, about 1.0% by weight, about 1.5% by weight, about 2.0% by weight, about 2.5% by weight, about 3.0% by weight, about 4.0% by weight, about 5.0% by weight, about 6.0% by weight, about 7.0% by weight, about 7.5% by weight, about 8.0% by weight, about 9.0% by weight, about 10.0% by weight, about 11.0% by weight, about 12.0% by weight, about 13.0% by weight, about 14.0% by weight, about 15.0% by weight, about 16.0% by weight, about 17.0% by weight, about 18.0% by weight, about 19.0% by weight, or about 20.0% by weight. In other aspects of this embodiment, a liquid composition comprises one or more non-ionic saponins in an amount of, e.g., at least 0.01% by weight, at least 0.05% by weight, at least 0.075% by weight, at least 0.1% by weight, at least 0.25% by weight, at least 0.5% by weight, at least 0.75% by weight, at least 1.0% by weight, at least 1.5% by weight, at least 2.0% by weight, at least 2.5% by weight, at least 3.0% by weight, at least 4.0% by weight, at least 5.0% by weight, at least 6.0% by weight, at least 7.0% by weight, at least 7.5% by weight, at least 8.0% by weight, at least 9.0% by weight, at least 10.0% by weight, at least 11.0% by weight, at least 12.0% by weight, at least 13.0% by weight, at least 14.0% by weight, at least 15.0% by weight, at least 16.0% by weight, at least 17.0% by weight, at least 18.0% by weight, at least 19.0% by weight, or at least 20.0% by weight. In yet other aspects of this embodiment, a liquid composition comprises one or more non-ionic saponins in an amount of, e.g., at most 0.01% by weight, at most 0.05% by weight, at most 0.075% by weight, at most 0.1% by weight, at most 0.25% by weight, at most 0.5% by weight, at most 0.75% by weight, at most 1.0% by weight, at most 1.5% by weight, at most 2.0% by weight, at most 2.5% by weight, at most 3.0% by weight, at most 4.0% by weight, at most 5.0% by weight, at most 6.0% by weight, at most 7.5% by weight, at most 8.0% by weight, at most 9.0% by weight, at most 10.0% by weight, at most 11.0% by weight, at most 12.0% by weight, at most 13.0% by weight, at most 14.0% by weight, at most 15.0% by weight, at most 16.0% by weight, at most 17.0% by weight, at most 18.0% by weight, at most 19.0% by weight, or at most 20.0% by weight In still other aspects of this embodiment, a liquid composition comprises one or more non-ionic saponins in an amount of, e.g., about 0.1% by weight to about 0.5% by weight, about 0.1% by weight to about 0.75% by weight, about 0.1% by weight to about 1.0% by weight, about 0.1% by weight to about 1.5% by weight, about 0.1% by weight to about 2.0% by weight, about 0.1% by weight to about 2.5% by weight, about 0.2% by weight to about 0.5% by weight, about 0.2% by weight to about 0.75% by weight, about 0.2% by weight to about 1.0% by weight, about 0.2% by weight to about 1.5% by weight, about 0.2% by weight to about 2.0% by weight, about 0.2% by weight to about 2.5% by weight, about 0.5% by weight to about 1.0% by weight, about 0.5% by weight to about 1.5% by weight, about 0.5% by weight to about 2.0% by weight, about 0.5% by weight to about 2.5% by weight, about 0.5% by weight to about 3.0% by weight, about 0.5% by weight to about 4.0% by weight, about 0.5% by weight to about 5.0% by weight, about 1.0% by weight to about 2.5% by weight, about 1.0% by weight to about 3.0% by weight, about 1.0% by weight to about 4.0% by weight, about 1.0% by weight to about 5.0% by weight, about 1.0% by weight to about 6.0% by weight, about 1.0% by weight to about 7.0% by weight, about 1.0% by weight to about 7.5% by weight, about 1.0% by weight to about 8.0% by weight, about 1.0% by weight to about 9.0% by weight, about 1.0% by weight to about 10.0% by weight, about 2.0% by weight to about 2.5% by weight, about 2.0% by weight to about 3.0% by weight, about 2.0% by weight to about 4.0% by weight, about 2.0% by weight to about 5.0% by weight, about 2.0% by weight to about 6.0% by weight, about 2.0% by weight to about 7.0% by weight, about 2.0% by weight to about 7.5% by weight, about 2.0% by weight to about 8.0% by weight, about 2.0% by weight to about 9.0% by weight, about 2.0% by weight to about 10.0% by weight, about 5.0% by weight to about 6.0% by weight, about 5.0% by weight to about 7.0% by weight, about 5.0% by weight to about 7.5% by weight, about 5.0% by weight to about 8.0% by weight, about 5.0% by weight to about 9.0% by weight, about 5.0% by weight to about 10.0% by weight, about 5.0% by weight to about 11.0% by weight, about 5.0% by weight to about 12.0% by weight, about 5.0% by weight to about 13.0% by weight, about 5.0% by weight to about 14.0% by weight, about 5.0% by weight to about 15.0% by weight, about 5.0% by weight to about 20.0% by weight, or about 5.0% by weight to about 25.0% by weight, about 10.0% by weight to about 15.0% by weight, about 10.0% by weight to about 20.0% by weight, or about 10.0% by weight to about 25.0% by weight, about 15.0% by weight to about 20.0% by weight, or about 15.0% by weight to about 25.0% by weight, or about 20.0% by weight to about 25.0% by weight.

In some embodiments, a liquid composition disclosed herein comprises a first non-ionic surfactant and a second non-ionic surfactant. In some embodiments, a liquid composition disclosed herein comprises a first non-ionic biosurfactant and a second non-ionic biosurfactant. In some embodiments, a liquid composition disclosed herein comprises a first non-ionic surfactant and a second non-ionic surfactant that is a biosurfactant or a saponin. In some embodiments, a liquid composition disclosed herein comprises a first non-ionic biosurfactant and a second non-ionic biosurfactant. In some embodiments, a liquid composition disclosed herein comprises a first non-ionic saponin and a second non-ionic saponin.

In aspects of these embodiments, a liquid composition disclosed herein comprises a first nonionic surfactant, including a biosurfactant or saponin, in an amount of, e.g., about 1.0% by weight, about 1.5% by weight, about 2.0% by weight, about 2.5% by weight, about 3.0% by weight, about 4.0% by weight, about 5.0% by weight, about 6.0% by weight, about 7.0% by weight, about 7.5% by weight, about 8.0% by weight, about 9.0% by weight, about 10.0% by weight, about 11.0% by weight, about 12.0% by weight, about 13.0% by weight, about 14.0% by weight, about 15.0% by weight, about 16.0% by weight, about 17.0% by weight, about 18.0% by weight, about 19.0% by weight, or about 20.0% by weight. In other aspects of this embodiment, a liquid composition comprises a first nonionic surfactant, including a biosurfactant or saponin, in an amount of, e.g., at least 0.01% by weight, at least 0.05% by weight, at least 0.075% by weight, at least 0.1% by weight, at least 0.25% by weight, at least 0.5% by weight, at least 0.75% by weight, at least 1.0% by weight, at least 1.5% by weight, at least 2.0% by weight, at least 2.5% by weight, at least 3.0% by weight, at least 4.0% by weight, at least 5.0% by weight, at least 6.0% by weight, at least 7.0% by weight, at least 7.5% by weight, at least 8.0% by weight, at least 9.0% by weight, at least 10.0% by weight, at least 11.0% by weight, at least 12.0% by weight, at least 13.0% by weight, at least 14.0% by weight, at least 15.0% by weight, at least 16.0% by weight, at least 17.0% by weight, at least 18.0% by weight, at least 19.0% by weight, or at least 20.0% by weight. In yet other aspects of this embodiment, a liquid composition comprises a first nonionic surfactant, including a biosurfactant or saponin, in an amount of, e.g., at most 0.01% by weight, at most 0.05% by weight, at most 0.075% by weight, at most 0.1% by weight, at most 0.25% by weight, at most 0.5% by weight, at most 0.75% by weight, at most 1.0% by weight, at most 1.5% by weight, at most 2.0% by weight, at most 2.5% by weight, at most 3.0% by weight, at most 4.0% by weight, at most 5.0% by weight, at most 6.0% by weight, at most 7.5% by weight, at most 8.0% by weight, at most 9.0% by weight, at most 10.0% by weight, at most 11.0% by weight, at most 12.0% by weight, at most 13.0% by weight, at most 14.0% by weight, at most 15.0% by weight, at most 16.0% by weight, at most 17.0% by weight, at most 18.0% by weight, at most 19.0% by weight, or at most 20.0% by weight In still other aspects of this embodiment, a liquid composition comprises a first nonionic surfactant, including a biosurfactant or saponin, in an amount of, e.g., about 0.1% by weight to about 0.5% by weight, about 0.1% by weight to about 0.75% by weight, about 0.1% by weight to about 1.0% by weight, about 0.1% by weight to about 1.5% by weight, about 0.1% by weight to about 2.0% by weight, about 0.1% by weight to about 2.5% by weight, about 0.2% by weight to about 0.5% by weight, about 0.2% by weight to about 0.75% by weight, about 0.2% by weight to about 1.0% by weight, about 0.2% by weight to about 1.5% by weight, about 0.2% by weight to about 2.0% by weight, about 0.2% by weight to about 2.5% by weight, about 0.5% by weight to about 1.0% by weight, about 0.5% by weight to about 1.5% by weight, about 0.5% by weight to about 2.0% by weight, about 0.5% by weight to about 2.5% by weight, about 0.5% by weight to about 3.0% by weight, about 0.5% by weight to about 4.0% by weight, about 0.5% by weight to about 5.0% by weight, about 1.0% by weight to about 2.5% by weight, about 1.0% by weight to about 3.0% by weight, about 1.0% by weight to about 4.0% by weight, about 1.0% by weight to about 5.0% by weight, about 1.0% by weight to about 6.0% by weight, about 1.0% by weight to about 7.0% by weight, about 1.0% by weight to about 7.5% by weight, about 1.0% by weight to about 8.0% by weight, about 1.0% by weight to about 9.0% by weight, about 1.0% by weight to about 10.0% by weight, about 2.0% by weight to about 2.5% by weight, about 2.0% by weight to about 3.0% by weight, about 2.0% by weight to about 4.0% by weight, about 2.0% by weight to about 5.0% by weight, about 2.0% by weight to about 6.0% by weight, about 2.0% by weight to about 7.0% by weight, about 2.0% by weight to about 7.5% by weight, about 2.0% by weight to about 8.0% by weight, about 2.0% by weight to about 9.0% by weight, about 2.0% by weight to about 10.0% by weight, about 5.0% by weight to about 6.0% by weight, about 5.0% by weight to about 7.0% by weight, about 5.0% by weight to about 7.5% by weight, about 5.0% by weight to about 8.0% by weight, about 5.0% by weight to about 9.0% by weight, about 5.0% by weight to about 10.0% by weight, about 5.0% by weight to about 11.0% by weight, about 5.0% by weight to about 12.0% by weight, about 5.0% by weight to about 13.0% by weight, about 5.0% by weight to about 14.0% by weight, about 5.0% by weight to about 15.0% by weight, about 5.0% by weight to about 20.0% by weight, or about 5.0% by weight to about 25.0% by weight, about 10.0% by weight to about 15.0% by weight, about 10.0% by weight to about 20.0% by weight, or about 10.0% by weight to about 25.0% by weight, about 15.0% by weight to about 20.0% by weight, or about 15.0% by weight to about 25.0% by weight, or about 20.0% by weight to about 25.0% by weight.

In some embodiments, a liquid composition disclosed herein comprises a second non-ionic biosurfactant and a second non-ionic biosurfactant. In aspects of these embodiments, a liquid composition disclosed herein comprises a second nonionic surfactant, including a biosurfactant or saponin, in an amount of, e.g., about 1.0% by weight, about 1.5% by weight, about 2.0% by weight, about 2.5% by weight, about 3.0% by weight, about 4.0% by weight, about 5.0% by weight, about 6.0% by weight, about 7.0% by weight, about 7.5% by weight, about 8.0% by weight, about 9.0% by weight, about 10.0% by weight, about 11.0% by weight, about 12.0% by weight, about 13.0% by weight, about 14.0% by weight, about 15.0% by weight, about 16.0% by weight, about 17.0% by weight, about 18.0% by weight, about 19.0% by weight, or about 20.0% by weight. In other aspects of this embodiment, a liquid composition comprises a second nonionic surfactant, including a biosurfactant or saponin, in an amount of, e.g., at least 0.01% by weight, at least 0.05% by weight, at least 0.075% by weight, at least 0.1% by weight, at least 0.25% by weight, at least 0.5% by weight, at least 0.75% by weight, at least 1.0% by weight, at least 1.5% by weight, at least 2.0% by weight, at least 2.5% by weight, at least 3.0% by weight, at least 4.0% by weight, at least 5.0% by weight, at least 6.0% by weight, at least 7.0% by weight, at least 7.5% by weight, at least 8.0% by weight, at least 9.0% by weight, at least 10.0% by weight, at least 11.0% by weight, at least 12.0% by weight, at least 13.0% by weight, at least 14.0% by weight, at least 15.0% by weight, at least 16.0% by weight, at least 17.0% by weight, at least 18.0% by weight, at least 19.0% by weight, or at least 20.0% by weight. In yet other aspects of this embodiment, a liquid composition comprises a second nonionic surfactant, including a biosurfactant or saponin, in an amount of, e.g., at most 0.01% by weight, at most 0.05% by weight, at most 0.075% by weight, at most 0.1% by weight, at most 0.25% by weight, at most 0.5% by weight, at most 0.75% by weight, at most 1.0% by weight, at most 1.5% by weight, at most 2.0% by weight, at most 2.5% by weight, at most 3.0% by weight, at most 4.0% by weight, at most 5.0% by weight, at most 6.0% by weight, at most 7.5% by weight, at most 8.0% by weight, at most 9.0% by weight, at most 10.0% by weight, at most 11.0% by weight, at most 12.0% by weight, at most 13.0% by weight, at most 14.0% by weight, at most 15.0% by weight, at most 16.0% by weight, at most 17.0% by weight, at most 18.0% by weight, at most 19.0% by weight, or at most 20.0% by weight In still other aspects of this embodiment, a liquid composition comprises a second nonionic surfactant, including a biosurfactant or saponin, in an amount of, e.g., about 0.1% by weight to about 0.5% by weight, about 0.1% by weight to about 0.75% by weight, about 0.1% by weight to about 1.0% by weight, about 0.1% by weight to about 1.5% by weight, about 0.1% by weight to about 2.0% by weight, about 0.1% by weight to about 2.5% by weight, about 0.2% by weight to about 0.5% by weight, about 0.2% by weight to about 0.75% by weight, about 0.2% by weight to about 1.0% by weight, about 0.2% by weight to about 1.5% by weight, about 0.2% by weight to about 2.0% by weight, about 0.2% by weight to about 2.5% by weight, about 0.5% by weight to about 1.0% by weight, about 0.5% by weight to about 1.5% by weight, about 0.5% by weight to about 2.0% by weight, about 0.5% by weight to about 2.5% by weight, about 0.5% by weight to about 3.0% by weight, about 0.5% by weight to about 4.0% by weight, about 0.5% by weight to about 5.0% by weight, about 1.0% by weight to about 2.5% by weight, about 1.0% by weight to about 3.0% by weight, about 1.0% by weight to about 4.0% by weight, about 1.0% by weight to about 5.0% by weight, about 1.0% by weight to about 6.0% by weight, about 1.0% by weight to about 7.0% by weight, about 1.0% by weight to about 7.5% by weight, about 1.0% by weight to about 8.0% by weight, about 1.0% by weight to about 9.0% by weight, about 1.0% by weight to about 10.0% by weight, about 2.0% by weight to about 2.5% by weight, about 2.0% by weight to about 3.0% by weight, about 2.0% by weight to about 4.0% by weight, about 2.0% by weight to about 5.0% by weight, about 2.0% by weight to about 6.0% by weight, about 2.0% by weight to about 7.0% by weight, about 2.0% by weight to about 7.5% by weight, about 2.0% by weight to about 8.0% by weight, about 2.0% by weight to about 9.0% by weight, about 2.0% by weight to about 10.0% by weight, about 5.0% by weight to about 6.0% by weight, about 5.0% by weight to about 7.0% by weight, about 5.0% by weight to about 7.5% by weight, about 5.0% by weight to about 8.0% by weight, about 5.0% by weight to about 9.0% by weight, about 5.0% by weight to about 10.0% by weight, about 5.0% by weight to about 11.0% by weight, about 5.0% by weight to about 12.0% by weight, about 5.0% by weight to about 13.0% by weight, about 5.0% by weight to about 14.0% by weight, about 5.0% by weight to about 15.0% by weight, about 5.0% by weight to about 20.0% by weight, or about 5.0% by weight to about 25.0% by weight, about 10.0% by weight to about 15.0% by weight, about 10.0% by weight to about 20.0% by weight, or about 10.0% by weight to about 25.0% by weight, about 15.0% by weight to about 20.0% by weight, or about 15.0% by weight to about 25.0% by weight, or about 20.0% by weight to about 25.0% by weight.

In aspects of these embodiments, a liquid composition disclosed herein comprises about 1% to about 20% of a first nonionic surfactant and about 1% to about 20% of a second nonionic surfactant. In other aspects of these embodiments, a liquid composition disclosed herein comprises about 2% to about 17% of a first nonionic surfactant and about 2% to about 17% of a second nonionic surfactant. In yet other aspects of these embodiments, a liquid composition disclosed herein comprises about 3% to about 15% of a first nonionic surfactant and about 3% to about 15% of a second nonionic surfactant. In still other aspects of these embodiments, a liquid composition disclosed herein comprises about 4% to about 12% of a first nonionic surfactant and about 4% to about 12% of a second nonionic surfactant.

In aspects of these embodiments, a liquid composition disclosed herein comprises about 1% to about 7% of a first nonionic surfactant and about 1% to about 7% of a second nonionic surfactant. In other aspects of these embodiments, a liquid composition disclosed herein comprises about 2% to about 6% of a first nonionic surfactant and about 2% to about 6% of a second nonionic surfactant. In yet other aspects of these embodiments, a liquid composition disclosed herein comprises about 2% to about 5% of a first nonionic surfactant and about 2% to about 5% of a second nonionic surfactant. In still other aspects of these embodiments, a liquid composition disclosed herein comprises about 2% to about 4% of a first nonionic surfactant and about 2% to about 4% of a second nonionic surfactant.

In other aspects of these embodiments, a liquid composition disclosed herein comprises a first nonionic surfactant and a second nonionic surfactant in a ratio of about 1:1 to about 1:10 relative to each other. In yet other aspects of these embodiments, about 1 part of a first nonionic surfactant to about 10 parts of a second nonionic surfactant, about 1 part of a first nonionic surfactant to about 9 parts of a second nonionic surfactant, about 1 part of a first nonionic surfactant to about 8 parts of a second nonionic surfactant, about 1 part of a first nonionic surfactant to about 7 parts of a second nonionic surfactant, about 1 part of a first nonionic surfactant to about 6 parts of a second nonionic surfactant, about 1 part of a first nonionic surfactant to about 5 parts of a second nonionic surfactant, about 1 part of a first nonionic surfactant to about 4 parts of a second nonionic surfactant, about 1 part of a first nonionic surfactant to about 3 parts of a second nonionic surfactant, about 1 part of a first nonionic surfactant to about 2 parts of a second nonionic surfactant, or about 1 part of a first nonionic surfactant to about 1 parts of a second nonionic surfactant.

In aspects of these embodiments, a liquid composition disclosed herein comprises about 1% to about 20% of a first nonionic biosurfactant and about 1% to about 20% of a second nonionic biosurfactant. In other aspects of these embodiments, a liquid composition disclosed herein comprises about 2% to about 17% of a first nonionic biosurfactant and about 2% to about 17% of a second nonionic biosurfactant. In yet other aspects of these embodiments, a liquid composition disclosed herein comprises about 3% to about 15% of a first nonionic biosurfactant and about 3% to about 15% of a second nonionic biosurfactant. In still other aspects of these embodiments, a liquid composition disclosed herein comprises about 4% to about 12% of a first nonionic biosurfactant and about 4% to about 12% of a second nonionic biosurfactant.

In aspects of these embodiments, a liquid composition disclosed herein comprises about 1% to about 7% of a first nonionic biosurfactant and about 1% to about 7% of a second nonionic biosurfactant. In other aspects of these embodiments, a liquid composition disclosed herein comprises about 2% to about 6% of a first nonionic biosurfactant and about 2% to about 6% of a second nonionic biosurfactant. In yet other aspects of these embodiments, a liquid composition disclosed herein comprises about 2% to about 5% of a first nonionic biosurfactant and about 2% to about 5% of a second nonionic biosurfactant. In still other aspects of these embodiments, a liquid composition disclosed herein comprises about 2% to about 4% of a first nonionic biosurfactant and about 2% to about 4% of a second nonionic biosurfactant.

In other aspects of these embodiments, a liquid composition disclosed herein comprises a first nonionic biosurfactant and a second nonionic biosurfactant in a ratio of about 1:1 to about 1:10 relative to each other. In yet other aspects of these embodiments, about 1 part of a first nonionic biosurfactant to about 10 parts of a second nonionic biosurfactant, about 1 part of a first nonionic biosurfactant to about 9 parts of a second nonionic biosurfactant, about 1 part of a first nonionic biosurfactant to about 8 parts of a second nonionic biosurfactant, about 1 part of a first nonionic biosurfactant to about 7 parts of a second nonionic biosurfactant, about 1 part of a first nonionic biosurfactant to about 6 parts of a second nonionic biosurfactant, about 1 part of a first nonionic biosurfactant to about 5 parts of a second nonionic biosurfactant, about 1 part of a first nonionic biosurfactant to about 4 parts of a second nonionic biosurfactant, about 1 part of a first nonionic biosurfactant to about 3 parts of a second nonionic biosurfactant, about 1 part of a first nonionic biosurfactant to about 2 parts of a second nonionic biosurfactant, or about 1 part of a first nonionic biosurfactant to about 1 parts of a second nonionic biosurfactant.

In aspects of these embodiments, a liquid composition disclosed herein comprises about 1% to about 20% of a first nonionic saponin and about 1% to about 20% of a second nonionic saponin. In other aspects of these embodiments, a liquid composition disclosed herein comprises about 2% to about 17% of a first nonionic saponin and about 2% to about 17% of a second nonionic saponin. In yet other aspects of these embodiments, a liquid composition disclosed herein comprises about 3% to about 15% of a first nonionic saponin and about 3% to about 15% of a second nonionic saponin. In still other aspects of these embodiments, a liquid composition disclosed herein comprises about 4% to about 12% of a first nonionic saponin and about 4% to about 12% of a second nonionic saponin.

In aspects of these embodiments, a liquid composition disclosed herein comprises about 1% to about 7% of a first nonionic saponin and about 1% to about 7% of a second nonionic saponin. In other aspects of these embodiments, a liquid composition disclosed herein comprises about 2% to about 6% of a first nonionic saponin and about 2% to about 6% of a second nonionic saponin. In yet other aspects of these embodiments, a liquid composition disclosed herein comprises about 2% to about 5% of a first nonionic saponin and about 2% to about 5% of a second nonionic saponin. In still other aspects of these embodiments, a liquid composition disclosed herein comprises about 2% to about 4% of a first nonionic saponin and about 2% to about 4% of a second nonionic saponin.

In other aspects of these embodiments, a liquid composition disclosed herein comprises a first nonionic saponin and a second nonionic saponin in a ratio of about 1:1 to about 1:10 relative to each other. In yet other aspects of these embodiments, about 1 part of a first nonionic saponin to about 10 parts of a second nonionic saponin, about 1 part of a first nonionic saponin to about 9 parts of a second nonionic saponin, about 1 part of a first nonionic saponin to about 8 parts of a second nonionic saponin, about 1 part of a first nonionic saponin to about 7 parts of a second nonionic saponin, about 1 part of a first nonionic saponin to about 6 parts of a second nonionic saponin, about 1 part of a first nonionic saponin to about 5 parts of a second nonionic saponin, about 1 part of a first nonionic saponin to about 4 parts of a second nonionic saponin, about 1 part of a first nonionic saponin to about 3 parts of a second nonionic saponin, about 1 part of a first nonionic saponin to about 2 parts of a second nonionic saponin, or about 1 part of a first nonionic saponin to about 1 parts of a second nonionic saponin.

Any amount of dried non-ionic surfactant disclosed herein may be used in a dry powdered composition disclosed herein, with the proviso that the amount is useful to practice the methods and uses disclosed herein. In some embodiments, a dry powdered composition disclosed herein comprises, e.g., about 75% to about 95% by weight of one or more dried non-ionic surfactants. In aspects of these embodiments, a dry powdered composition comprises one or more dried non-ionic surfactants in an amount of, e.g., about 75% by weight, about 80% by weight, about 85% by weight, about 90% by weight, about 95% by weight. In other aspects of these embodiments, a dry powdered composition comprises one or more dried non-ionic surfactants in an amount of, e.g., at most 75% by weight, at most 80% by weight, at most 85% by weight, at most 90% by weight, at most 95% by weight. In yet other aspects of these embodiments, a dry powdered composition comprises one or more dried non-ionic surfactants in an amount of, e.g., at least 75% by weight, at least 80% by weight, at least 85% by weight, at least 90% by weight, at least 95% by weight. In still other aspects of these embodiments, a dry powdered composition comprises one or more dried non-ionic surfactants in an amount of, e.g., about 80% to about 90% by weight, about 85% to about 90% by weight, about 87% to about 90% by weight, about 89% to about 90% by weight, or about 89% to about 89.9% by weight. In other aspects of these embodiments, a dry powdered composition comprises one or more dried non-ionic surfactants in an amount of, e.g., about 75% to about 80% by weight, about 75% to about 85% by weight, about 75% to about 90% by weight, about 75% to about 95% by weight, about 80% to about 85% by weight, about 80% to about 90% by weight, about 80% to about 95% by weight, about 85% to about 90% by weight, about 85% to about 95% by weight, or about 90% to about 95% by weight.

In some embodiments, a dry powdered composition disclosed herein comprises, e.g., about 75% to about 95% by weight of one or more dried non-ionic biosurfactants. In aspects of these embodiments, a dry powdered composition comprises one or more dried non-ionic biosurfactants in an amount of, e.g., about 75% by weight, about 80% by weight, about 85% by weight, about 90% by weight, about 95% by weight. In other aspects of these embodiments, a dry powdered composition comprises one or more dried non-ionic biosurfactants in an amount of, e.g., at most 75% by weight, at most 80% by weight, at most 85% by weight, at most 90% by weight, at most 95% by weight. In yet other aspects of these embodiments, a dry powdered composition comprises one or more dried non-ionic biosurfactants in an amount of, e.g., at least 75% by weight, at least 80% by weight, at least 85% by weight, at least 90% by weight, at least 95% by weight. In still other aspects of these embodiments, a dry powdered composition comprises one or more dried non-ionic biosurfactants in an amount of, e.g., about 80% to about 90% by weight, about 85% to about 90% by weight, about 87% to about 90% by weight, about 89% to about 90% by weight, or about 89% to about 89.9% by weight. In other aspects of these embodiments, a dry powdered composition comprises one or more dried non-ionic biosurfactants in an amount of, e.g., about 75% to about 80% by weight, about 75% to about 85% by weight, about 75% to about 90% by weight, about 75% to about 95% by weight, about 80% to about 85% by weight, about 80% to about 90% by weight, about 80% to about 95% by weight, about 85% to about 90% by weight, about 85% to about 95% by weight, or about 90% to about 95% by weight.

In some embodiments, a dry powdered composition disclosed herein comprises, e.g., about 75% to about 95% by weight of one or more dried non-ionic saponins. In aspects of these embodiments, a dry powdered composition comprises one or more dried non-ionic saponins in an amount of, e.g., about 75% by weight, about 80% by weight, about 85% by weight, about 90% by weight, about 95% by weight. In other aspects of these embodiments, a dry powdered composition comprises one or more dried non-ionic saponins in an amount of, e.g., at most 75% by weight, at most 80% by weight, at most 85% by weight, at most 90% by weight, at most 95% by weight. In yet other aspects of these embodiments, a dry powdered composition comprises one or more dried non-ionic saponins in an amount of, e.g., at least 75% by weight, at least 80% by weight, at least 85% by weight, at least 90% by weight, at least 95% by weight. In still other aspects of these embodiments, a dry powdered composition comprises one or more dried non-ionic saponins in an amount of, e.g., about 80% to about 90% by weight, about 85% to about 90% by weight, about 87% to about 90% by weight, about 89% to about 90% by weight, or about 89% to about 89.9% by weight. In other aspects of these embodiments, a dry powdered composition comprises one or more dried non-ionic saponins in an amount of, e.g., about 75% to about 80% by weight, about 75% to about 85% by weight, about 75% to about 90% by weight, about 75% to about 95% by weight, about 80% to about 85% by weight, about 80% to about 90% by weight, about 80% to about 95% by weight, about 85% to about 90% by weight, about 85% to about 95% by weight, or about 90% to about 95% by weight. In other aspects of these embodiments, the one or more saponins include one or more triterpenoid saponins, one or more steroidal saponins, or a combination thereof.

In some embodiments, a dry powdered composition disclosed herein comprises a first dried non-ionic biosurfactant and a second dried non-ionic biosurfactant. In aspects of these embodiments, a dry powdered composition disclosed herein comprises a first dried nonionic biosurfactant in an amount of, e.g., about 5.0% by weight to about 6.0% by weight, about 5.0% by weight to about 7.0% by weight, about 5.0% by weight to about 8.0% by weight, about 5.0% by weight to about 9.0% by weight, about 5.0% by weight to about 10.0% by weight, about 5.0% by weight to about 11.0% by weight, about 5.0% by weight to about 12.0% by weight, about 5.0% by weight to about 13.0% by weight, about 5.0% by weight to about 14.0% by weight or about 5.0% by weight to about 15.0% by weight. In other aspects of these embodiments, a dry powdered composition disclosed herein comprises a second dried nonionic biosurfactant in an amount of, e.g., about 70% by weight to about 75% by weight, about 70% by weight to about 80% by weight, about 70% by weight to about 85% by weight, about 70% by weight to about 90% by weight, about 75% by weight to about 80% by weight, about 75% by weight to about 85% by weight, about 75% by weight to about 90% by weight, about 80% by weight to about 85% by weight, or about 80% by weight to about 90% by weight.

In aspects of these embodiments, a dry powdered composition disclosed herein comprises about 5% to about 15% of a first dried nonionic biosurfactant and about 70% to about 90% of a second dried nonionic biosurfactant. In other aspects of these embodiments, a dry powdered composition disclosed herein comprises about 5% to about 15% of a first dried nonionic biosurfactant and about 75% to about 85% of a second dried nonionic biosurfactant. In yet other aspects of these embodiments, a dry powdered composition disclosed herein comprises about 6% to about 12% of a first dried nonionic biosurfactant and about 73% to about 89% of a second dried nonionic biosurfactant. In still other aspects of these embodiments, a dry powdered composition disclosed herein comprises about 6% to about 12% of a first dried nonionic biosurfactant and about 78% to about 84% of a second dried nonionic biosurfactant.

In aspects of these embodiments, a dry powdered composition disclosed herein comprises about 7% to about 11% of a first dried nonionic biosurfactant and about 74% to about 88% of a second dried nonionic biosurfactant. In other aspects of these embodiments, a dry powdered composition disclosed herein comprises about 7% to about 11% of a first dried nonionic biosurfactant and about 79% to about 83% of a second dried nonionic biosurfactant. In yet other aspects of these embodiments, a dry powdered composition disclosed herein comprises about 8% to about 10% of a first dried nonionic biosurfactant and about 75% to about 87% of a second dried nonionic biosurfactant. In still other aspects of these embodiments, a dry powdered composition disclosed herein comprises about 8% to about 10% of a first dried nonionic biosurfactant and about 80% to about 82% of a second dried nonionic biosurfactant. In yet other aspects of these embodiments, a dry powdered composition disclosed herein comprises about 9% of a first dried nonionic biosurfactant and about 81% of a second dried nonionic biosurfactant.

In other aspects of these embodiments, a dry powdered composition disclosed herein comprises a first dried nonionic biosurfactant and a second dried nonionic biosurfactant in a ratio of about 1:3 to about 1:20 relative to each other. In yet other aspects of these embodiments, a dry powdered composition disclosed herein comprises a ratio of about 1 part of a first dried nonionic biosurfactant to about 18 parts of a second dried nonionic biosurfactant, about 1 part of a first dried nonionic biosurfactant to about 17 parts of a second dried nonionic biosurfactant, about 1 part of a first dried nonionic biosurfactant to about 16 parts of a second dried nonionic biosurfactant, about 1 part of a first dried nonionic biosurfactant to about 15 parts of a second dried nonionic biosurfactant, about 1 part of a first dried nonionic biosurfactant to about 14 parts of a second dried nonionic biosurfactant, about 1 part of a first dried nonionic biosurfactant to about 13 parts of a second dried nonionic biosurfactant, about 1 part of a first dried nonionic biosurfactant to about 12 parts of a second dried nonionic biosurfactant, about 1 part of a first dried nonionic biosurfactant to about 11 parts of a second dried nonionic biosurfactant, about 1 part of a first dried nonionic biosurfactant to about 10 parts of a second dried nonionic biosurfactant, about 1 part of a first dried nonionic biosurfactant to about 9 parts of a second dried nonionic biosurfactant, about 1 part of a first dried nonionic biosurfactant to about 8 parts of a second dried nonionic biosurfactant, about 1 part of a first dried nonionic biosurfactant to about 7 parts of a second dried nonionic biosurfactant, about 1 part of a first dried nonionic biosurfactant to about 6 parts of a second dried nonionic biosurfactant, about 1 part of a first dried nonionic biosurfactant to about 5 parts of a second dried nonionic biosurfactant, or about 1 part of a first dried nonionic biosurfactant to about 4 parts of a second dried nonionic biosurfactant.

In some embodiments, a dry powdered composition disclosed herein comprises a first dried non-ionic saponin and a second dried non-ionic saponin. In aspects of these embodiments, a dry powdered composition disclosed herein comprises a first dried nonionic saponin in an amount of, e.g., about 5.0% by weight to about 6.0% by weight, about 5.0% by weight to about 7.0% by weight, about 5.0% by weight to about 8.0% by weight, about 5.0% by weight to about 9.0% by weight, about 5.0% by weight to about 10.0% by weight, about 5.0% by weight to about 11.0% by weight, about 5.0% by weight to about 12.0% by weight, about 5.0% by weight to about 13.0% by weight, about 5.0% by weight to about 14.0% by weight or about 5.0% by weight to about 15.0% by weight. In other aspects of these embodiments, a dry powdered composition disclosed herein comprises a second dried nonionic saponin in an amount of, e.g., about 70% by weight to about 75% by weight, about 70% by weight to about 80% by weight, about 70% by weight to about 85% by weight, about 70% by weight to about 90% by weight, about 75% by weight to about 80% by weight, about 75% by weight to about 85% by weight, about 75% by weight to about 90% by weight, about 80% by weight to about 85% by weight, or about 80% by weight to about 90% by weight. In other aspects of these embodiments, a first and second dried saponins include one or more triterpenoid saponins, one or more steroidal saponins, or a combination thereof.

In aspects of these embodiments, a dry powdered composition disclosed herein comprises about 5% to about 15% of a first dried nonionic saponin and about 70% to about 90% of a second dried nonionic saponin. In other aspects of these embodiments, a dry powdered composition disclosed herein comprises about 5% to about 15% of a first dried nonionic saponin and about 75% to about 85% of a second dried nonionic saponin. In yet other aspects of these embodiments, a dry powdered composition disclosed herein comprises about 6% to about 12% of a first dried nonionic saponin and about 73% to about 89% of a second dried nonionic saponin. In still other aspects of these embodiments, a dry powdered composition disclosed herein comprises about 6% to about 12% of a first dried nonionic saponin and about 78% to about 84% of a second dried nonionic saponin.

In aspects of these embodiments, a dry powdered composition disclosed herein comprises about 7% to about 11% of a first dried nonionic saponin and about 74% to about 88% of a second dried nonionic saponin. In other aspects of these embodiments, a dry powdered composition disclosed herein comprises about 7% to about 11% of a first dried nonionic saponin and about 79% to about 83% of a second dried nonionic saponin. In yet other aspects of these embodiments, a dry powdered composition disclosed herein comprises about 8% to about 10% of a first dried nonionic saponin and about 75% to about 87% of a second dried nonionic saponin. In still other aspects of these embodiments, a dry powdered composition disclosed herein comprises about 8% to about 10% of a first dried nonionic saponin and about 80% to about 82% of a second dried nonionic saponin. In yet other aspects of these embodiments, a dry powdered composition disclosed herein comprises about 9% of a first dried nonionic saponin and about 81% of a second dried nonionic saponin. In other aspects of these embodiments, a first dried and second dried saponins include one or more triterpenoid saponins, one or more steroidal saponins, or a combination thereof.

In other aspects of these embodiments, a dry powdered composition disclosed herein comprises a first dried nonionic saponin and a second dried nonionic saponin in a ratio of about 1:1 to about 1:20 relative to each other. In other aspects of these embodiments, a dry powdered composition disclosed herein comprises a ratio of about 1 part of a first dried nonionic saponin to about 18 parts of a second dried nonionic saponin, about 1 part of a first dried nonionic saponin to about 17 parts of a second dried nonionic saponin, about 1 part of a first dried nonionic saponin to about 16 parts of a second dried nonionic saponin, about 1 part of a first dried nonionic saponin to about 15 parts of a second dried nonionic saponin, about 1 part of a first dried nonionic saponin to about 14 parts of a second dried nonionic saponin, about 1 part of a first dried nonionic saponin to about 13 parts of a second dried nonionic saponin, about 1 part of a first dried nonionic saponin to about 12 parts of a second dried nonionic saponin, about 1 part of a first dried nonionic saponin to about 11 parts of a second dried nonionic saponin, about 1 part of a first dried nonionic saponin to about 10 parts of a second dried nonionic saponin, about 1 part of a first dried nonionic saponin to about 9 parts of a second dried nonionic saponin, about 1 part of a first dried nonionic saponin to about 8 parts of a second dried nonionic saponin, about 1 part of a first dried nonionic saponin to about 7 parts of a second dried nonionic saponin, about 1 part of a first dried nonionic saponin to about 6 parts of a second dried nonionic saponin, about 1 part of a first dried nonionic saponin to about 5 parts of a second dried nonionic saponin, or about 1 part of a first dried nonionic saponin to about 4 parts of a second dried nonionic saponin. In other aspects of these embodiments, a first dried and second dried saponins include one or more triterpenoid saponins, one or more steroidal saponins, or a combination thereof.

Aspects of the present specification disclose, in part, dissolving a dry powdered composition disclosed herein with a solvent to provide a liquid composition. A solvent is a liquid substance capable of dissolving another substance, e.g., a solvent is used to dissolve a dry powered composition disclosed herein to form a liquid composition disclosed herein. A solvent disclosed herein can be water or a monophasic water-based solution, or a bi- or multiphasic water-based colloidal mixture including an aerosol, emulsion, gel, foam or sol. In some embodiments, a solvent can include other characteristics such as diluting, dispersing, and/or film forming properties. In some embodiments, a solvent can be combined with other components, such as, e.g., another solvent, a diluent, a thickening agent, a dispersing agent, a binding agent, a foaming agent, a stabilizing agent, a film forming agent, or a preservative or the like.

The amount of solvent added to a dry powdered composition disclosed herein is an amount sufficient to produce a liquid composition disclosed herein. In an embodiment, a ratio of dry powdered composition to solvent added to form a liquid composition disclosed herein is from 1:1 to 1:500. In aspects of this embodiment, a ratio of dry powdered composition to solvent added to form a liquid composition disclosed herein is, e.g., about 1:10, about 1:20, about 1:25, about 1:30, about 1:40, about 1:50, about 1:60, about 1:70, about 1:75, about 1:80, about 1:190, or about 1:100. In other aspects of this embodiment, a ratio of dry powdered composition to solvent added to form a liquid composition disclosed herein is, e.g., at least 1:10, at least 1:20, at least 1:25, at least 1:30, at least 1:40, at least 1:50, at least 1:60, at least 1:70, at least 1:75, at least 1:80, at least 1:190, or at least 1:100. In yet other aspects of this embodiment, a ratio of dry powdered composition to solvent added to form a liquid composition disclosed herein is, e.g., at most 1:10, at most 1:20, at most 1:25, at most 1:30, at most 1:40, at most 1:50, at most 1:60, at most 1:70, at most 1:75, at most 1:80, at most 1:190, or at most 1:100. In still other aspects of this embodiment, a ratio of dry powdered composition to solvent added to form a liquid composition disclosed herein is, e.g., about 1:10 to about 1:20, about 1:10 to about 1:30, about 1:10 to about 1:40, about 1:10 to about 1:50, about 1:10 to about 1:60, about 1:10 to about 1:70, about 1:10 to about 1:80, about 1:10 to about 1:90, about 1:10 to about 1:100, about 1:20 to about 1:30, about 1:20 to about 1:40, about 1:20 to about 1:50, about 1:20 to about 1:60, about 1:20 to about 1:70, about 1:20 to about 1:80, about 1:20 to about 1:90, about 1:20 to about 1:100, about 1:25 to about 1:35, about 1:25 to about 1:40, about 1:25 to about 1:50, about 1:30 to about 1:40, about 1:30 to about 1:50, about 1:30 to about 1:60, about 1:30 to about 1:70, about 1:30 to about 1:80, about 1:30 to about 1:90, about 1:30 to about 1:100, about 1:40 to about 1:50, about 1:40 to about 1:60, about 1:40 to about 1:70, about 1:40 to about 1:80, about 1:40 to about 1:90, about 1:40 to about 1:100, about 1:50 to about 1:60, about 1:50 to about 1:70, about 1:50 to about 1:80, about 1:50 to about 1:90, about 1:50 to about 1:100, about 1:60 to about 1:70, about 1:60 to about 1:80, about 1:60 to about 1:90, about 1:60 to about 1:100, about 1:70 to about 1:80, about 1:70 to about 1:90, about 1:70 to about 1:100, about 1:80 to about 1:90, about 1:80 to about 1:100, or about 1:90 to about 1:100.

In an embodiment, the percentage by weight of dry powdered composition added to a solvent to form a liquid composition disclosed herein is from 0.1% to 50%. In aspects of this embodiment, the percentage by weight of dry powdered composition added to a solvent to form a liquid composition disclosed herein is, e.g., about 0.1%, about 0.25%, about 0.5%, about 0.75%, about 1%, about 2%, about 3%, about 4%, about 5%, about 6%, about 7%, about 8%, about 9% to about 10%. In other aspects of this embodiment, the percentage by weight of dry powdered composition added to a solvent to form a liquid composition disclosed herein is, e.g., at least 0.1%, at least 0.25%, at least 0.5%, at least 0.75%, at least 1%, at least 2%, at least 3%, at least 4%, at least 5%, at least 6%, at least 7%, at least 8%, at least 9% to at least 10%. In yet other aspects of this embodiment, the percentage by weight of dry powdered composition added to a solvent to form a liquid composition disclosed herein is, e.g., at most 0.1%, at most 0.25%, at most 0.5%, at most 0.75%, at most 1%, at most 2%, at most 3%, at most 4%, at most 5%, at most 6%, at most 7%, at most 8%, at most 9% to at most 10%. In still other aspects of this embodiment, the percentage by weight of dry powdered composition added to a solvent to form a liquid composition disclosed herein is, e.g., about 0.1% to about 0.5%, about 0.1% to about 1%, about 0.1% to about 2%, about 0.1% to about 3%, about 0.1% to about 4%, about 0.1% to about 5%, about 0.1% to about 6%, about 0.1% to about 7%, about 0.1% to about 8%, about 0.1% to about 9%, about 0.1% to about 10%, about 0.5% to about 1%, about 0.5% to about 2%, about 0.5% to about 3%, about 0.5% to about 4%, about 0.5% to about 5%, about 0.5% to about 6%, about 0.5% to about 7%, about 0.5% to about 8%, about 0.5% to about 9%, about 0.5% to about 10%, about 1% to about 2%, about 1% to about 3%, about 1% to about 4%, about 1% to about 5%, about 1% to about 6%, about 1% to about 7%, about 1% to about 8%, about 1% to about 9%, about 1% to about 10%, about 2% to about 3%, about 2% to about 4%, about 2% to about 5%, about 2% to about 6%, about 2% to about 7%, about 2% to about 8%, about 2% to about 9%, about 2% to about 10%, about 3% to about 4%, about 3% to about 5%, about 3% to about 6%, about 3% to about 7%, about 3% to about 8%, about 3% to about 9%, about 3% to about 10%, about 4% to about 5%, about 4% to about 6%, about 4% to about 7%, about 4% to about 8%, about 4% to about 9%, about 4% to about 10%, about 5% to about 6%, about 5% to about 7%, about 5% to about 8%, about 5% to about 9%, about 5% to about 10%, about 6% to about 7%, about 6% to about 8%, about 6% to about 9%, about 6% to about 10%, about 7% to about 8%, about 7% to about 9%, about 7% to about 10%, about 8% to about 9%, about 8% to about 10%, or about 8% to about 10%.

Aspects of the present specification disclose, in part, a pH of a liquid composition disclosed herein. Whether formulated directly as a liquid composition or formed by dissolving a dry powdered composition disclosed herein, the final pH of a liquid composition disclosed herein is typically acidic, in part because this contributes to the stability of the liquid composition. In aspects of this embodiment, the pH of a liquid composition disclosed herein is, e.g., about 2, about 2.5, about 3, about 3.5, about 4, about 4.5, about 5, about 5.5 or about 6. In other aspects of this embodiment, the pH of a liquid composition disclosed herein is, e.g., at least 2, at least 2.5, at least 3, at least 3.5, at least 4, at least 4.5, at least 5, at least 5.5 or at least 6. In yet other aspects of this embodiment, the pH of a fire extinguishing composition and/or fire extinguishing agent composition disclosed herein is, e.g., at most 2, at most 2.5, at most 3, at most 3.5, at most 4, at most 4.5, at most 5, at most 5.5 or at most 6. In still other aspects of this embodiment, the pH of a liquid composition disclosed herein is between, e.g., about 2 to about 3, about 2 to about 3.5, about 2 to about 4, about 2 to about 4.5, about 2 to about 5, about 2 to about 5.5, about 2 to about 6, about 2.5 to about 3, about 2.5 to about 3.5, about 2.5 to about 4, about 2.5 to about 4.5, about 2.5 to about 5, about 2.5 to about 5.5, about 2.5 to about 6, about 3 to about 3.5, about 3 to about 4, about 3 to about 4.2, about 3 to about 4.5, about 3 to about 4.7, about 3 to about 5, about 3 to about 5.2, about 3 to about 5.5, about 3 to about 6, about 3.5 to about 4, about 3.5 to about 4.2, about 3.5 to about 4.5, about 3.5 to about 4.7, about 3.5 to about 5, about 3.5 to about 5.2, about 3.5 to about 5.5, about 3.5 to about 6, about 3.7 to about 4.0, about 3.7 to about 4.2, about 3.7 to about 4.5, about 3.7 to about 5.2, about 3.7 to about 5.5 or about 3.7 to about 6.0.

A dry powdered composition or liquid composition, whether formulated directly as a liquid composition or formed by dissolving a dry powdered composition disclosed herein, can include one or more other components that confer properties or functionalities useful in one or more formulaic forms of a liquid composition disclosed herein including paste and colloidal formulations. None limiting examples of such components include a solvent, a diluent, a thickening agent, a dispersing agent, a binding agent, a foaming agent, a stabilizing agent, a film forming agent, or a preservative.

A diluent (also referred to as a diluting agent, dilutent, thinner or filler) is a substance that decreases the viscosity or density of a dry powdered composition or liquid composition disclosed herein. A liquid composition disclosed herein may be too viscous or dense to be effectively pumped, sprayed or otherwise applied to a structure or environmental area or to flow from one particular point to another according to a method or use disclosed herein. A diluent is added to a liquid composition disclosed herein in order to reduce its viscosity or density. In some embodiments, a diluent is added to a liquid composition disclosed herein formulated as a concentrate that requires dilution before use. In some embodiments, a diluent can include characteristics of a solvent. In some embodiments, a diluent can be combined with other components, such as, e.g., a solvent, another diluent, a thickening agent, a dispersing agent, a binding agent, a foaming agent, a stabilizing agent, a film forming agent, or a preservative or the like. Non-limiting examples of a diluent includes water, a monophasic water-based solution, or a bi- or multiphasic water-based colloidal mixture, or the like or any combination thereof. In some embodiments one or more diluents, including two or more, three or more, four or more, or five or more diluents can be added individually or collectively to a composition disclosed herein in a total amount of 1% to about 75%, about 5% to about 60% by weight, about 10% to about 50%, or about 15% to about 40% by weight of each of the one or more diluents.

A thickening agent (also referred to as a thickener) is a substance that increases the viscosity or density of a liquid composition disclosed herein. A liquid composition disclosed herein may be too watery or unsticky to be effectively applied to a structure or environmental area according to a method or use disclosed herein. A thickening agent is added to a liquid composition disclosed herein in order to increase its viscosity or density. In some embodiments, a diluent is added to a dry powdered composition disclosed herein to bulk up a dry powdered composition disclosed herein In some embodiments, a diluent is added to a liquid composition disclosed herein to formulate a paste composition disclosed herein. In some embodiments, a thickening agent is a swellable thickening agent that aids in causing a foam to form a gel when a composition disclosed herein comes into contact with a polar hydrophilic liquid (e.g. alcohols, ketones etc.). In some embodiments, the thickening agent acts as a barrier towards the fuel vapors and liquids and prevents the foam blanket from breaking. In some embodiments, a thickening agent can be combined with other components, such as, e.g., a solvent, a diluent, another thickening agent, a dispersing agent, a binding agent, a foaming agent, a stabilizing agent, a film forming agent, or a preservative or the like. Thickening agents include gums and starches. Non-limiting examples of a thickening agent includes guar gum, diutan gum, rhamsam gum, welan gum, galactomannan gum, mannan gum, locust bean gum, carbomer, xanthan gum, gum Arabic, pectin (pectic acid), Acacia gum, insulin guar, karaya, agar, algin (alginic acid), carrageenan, furcellaran, curdlan, dextran, cellulon, pullulan, cornstarch, potato starch, tapioca, rice starch, cellulose, hydroxyethyl cellulose, carboxymethylcellulose (CMC), methylcellulose, cyclodextrins, polydextrose, glycogen, hyaluronic acid, chitin, or the like or any combination thereof. In some embodiments one or more thickening agents, including two or more, three or more, four or more, or five or more thickening agents can be added individually or collectively to a composition disclosed herein in a total amount of 0.01% to about 30%, about 0.1% to about 20% by weight, about 1% to about 10%, about 2% to about 5% or about 1% to about 3% by weight of each of the one or more thickening agents.

A dispersing agent (also known as a dispersant or a plasticizer) is a compound or mixture of compounds that is either a non-surface-active polymer or a surface-active substance added to a dry powdered composition or a liquid composition to improve the separation of particles and to prevent settling or clumping. In some embodiments, a dispersing agent is added to a dry powdered composition disclosed herein to improve the separation of particles and to prevent settling or clumping. In some embodiments, a dispersing agent is added to a liquid composition disclosed herein formulated as a colloidal composition disclosed herein to improve the separation of particles and to prevent settling or clumping. In some embodiments, a dispersing agent can be combined with other components, such as, e.g., a solvent, a diluent, a thickening agent, another dispersing agent, a foaming agent, a stabilizing agent, a film forming agent, or a preservative or the like. Non-limiting examples of a dispersing agent includes a surfactant, an emulsifier, a clay, acrylic acid-based compounds, sodium bis(tridecyl) sulfosuccinate, di(2-ethyl hexyl) sodium sulfosuccinate, sodium dihexylsulfosuccinate, sodium dicyclohexyl sulfosuccinate, diamyl sodium sulfosuccinate, sodium diisobutyl sulfosuccinate, disodium iso-decyl sulfosuccinate, disodium ethoxylated alcohol half ester of sulfosuccinic acid, disodium alkyl amido polyethoxy sulfosuccinate, tetra-sodium N-(1,2-dicarboxyethyl)-N-octadecyl sulfosuccinamate, disodium N-octasulfosuccinamate, and sulfated ethoxylated nonylphenol, 2-amino-2-methyl-1-propanol, mono $C_{8-24}$ fatty acids, $C\&_{24}$ saturated fatty acids, and phthalate esters such as di-2-ethyl hexyl phthalate (DEHP), diisodecyl phthalate (DIDP), diisononyl phthalate (DINP), and benzylbutylphthalate (BBP) or the like or any combination thereof. In some embodiments one or more dispersing agents, including two or more, three or more, four or more, or five or more dispersing agents can be added individually or collectively to a composition disclosed herein in a total amount of 0.01% to about 30%, about 0.1% to about 20% by weight, about 1% to about 10%, about 2% to about 5% or about 1% to about 3% by weight of each of the one or more dispersing agents.

A binding agent (also known as a binder) is a compound or mixture of compounds that improves the adherence and/or cohesion of one or more other components comprising a dry powdered or liquid composition disclosed herein together to form a cohesive whole mechanically, chemically, by adhesion or cohesion. In some embodiments one or more binding agents, including two or more, three or more, four or more, or five or more binding agents can be added individually or collectively to a composition disclosed herein in a total amount of 0.01% to about 30%, about 0.1% to about 20% by weight, about 1% to about 10%, about 2% to about 5% or about 1% to about 3% by weight of each of the one or more binding agents.

A foaming agent (also known as a blowing agent) is a compound or mixture of compounds that produces gas when hydrated under suitable conditions and gives a composition disclosed herein foaming properties and/or boost the foaming properties. For example, a foaming agent can facilitate formation of a foam by reducing the surface tension of a liquid composition disclosed herein or increasing the colloidal stability by inhibiting coalescence of bubbles of a liquid composition disclosed herein formulated as a colloidal composition disclosed herein. In some embodiments, a foaming agent can be combined with other components, such as, e.g., a solvent, a diluent, a thickening agent, a dispersing agent, a binding agent, another foaming agent, a stabilizing agent, a film forming agent, or a preservative or the like. Synthetic and protein-based forming agents. Synthetic forming agents include aqueous film forming foaming agents and alcohol-resistant aqueous film-forming foaming agents. Protein-based forming agents include animal protein-based forming agents, plant protein-based forming agents, fluoroprotein forming agents, film-forming fluoroprotein forming agents, alcohol-resistant fluoroprotein forming agents, alcohol-resistant film-forming fluoroprotein forming agents. Non-limiting examples of a foaming agent includes alfalfa extract, *Medicago sativa*, hydroxypropyl methylcellulose (HPMC), methylcellulose, non-ionic water-soluble polymers, ionic water-soluble polymers, hydrocarbon-based surfactants such as sodium alkyl sulfate, or the like or any combination thereof. In some embodiments one or more foaming agents, including two or more, three or more, four or more, or five or more foaming agents can be added individually or collectively to a composition disclosed herein in a total amount of 0.2% to about 15% by weight, about 0.5% to about 10% by weight, or about 1% to about 6% by weight, or about 1% to about 5% by weight of each of the one or more foaming agents.

A stabilizing agent (also known as a stabilizer, emulsifier, or emulgent) is a compound or mixture of compounds that increases the stability of a dry powdered composition or a liquid composition disclosed herein including a paste or colloidal composition disclosed herein. In some embodiments, a stabilizing agent is added to a dry powdered composition disclosed herein to increase its stability. In some embodiments, a stabilizing agent is added to a liquid composition disclosed herein including a paste or colloidal composition disclosed herein to increase its stability. In some embodiments, a stabilizing agent can include characteristics of a solvent. In some embodiments, a stabilizing agent can be combined with other components, such as, e.g., a solvent, a diluent, a thickening agent, a dispersing agent, a binding agent, a foaming agent, another stabilizing agent, a film forming agent, or a preservative or the like. A stabilizing agent includes a foam stabilizing agent that extends the lifetime of a foam composition disclosed herein. Non-limiting examples of a stabilizing agent includes partially hydrolyzed protein, starches, polyvinyl resins such as polyvinyl alcohol, polyacrylamides, carboxyvinyl polymers, polypyrrolidine and poly(oxyethylene) glycol, ethylene glycol, propylene glycol, glycol ethers, including glycol monoethers like methyl, propyl, butyl or hexyl mono-ether, e.g., 2-butoxyethanol, or glycol diethers like diethylene glycol ethers (carbitols), butyl carbitol, hexylene glycol, lauryl alcohol, formaldehyde and alkyl hydroxy benzoates; preferably the preserving or stabilizing agents is a mixture of methyl and propyl hydroxy benzoates, or the like or any combination thereof. In some embodiments one or more stabilizing agents, including two or more, three or more, four or more, or five or more stabilizing agents can be added individually or collectively to a composition disclosed herein in a total amount of 0.1% to about 50%, about 0.5% to about 40% by weight, about 1% to about 30%, about 2% to about 30% or about 5% to about 25% by weight of each of the one or more stabilizing agents. In some embodiments one or more stabilizing agents, including two or more, three or more, four or more, or five or more stabilizing agents can be added individually or collectively to a composition disclosed herein in a total amount of 0.1% to about 10% by weight, about 0.5% to about 8% by weight, about 1% to about 10% by weight, about 1% to about 8% by weight, about 1% to about 6% by weight, about 1% to about 5% by weight, about 2% to about 6% by weight, about 3% to about 9% by weight, or about 3% to about 6% by weight of each of the one or more stabilizing agents.

A film forming agent is a compound or mixture of compounds that facilitates a pliable, cohesive and continuous hydrophobic covering of a liquid composition disclosed herein over a surface. In some embodiments, a film forming agent can include characteristics of a solvent. In some embodiments, a diluent can be combined with other components, such as, e.g., a solvent, a diluent, a thickening agent, a dispersing agent, a binding agent, a foaming agent, a stabilizing agent, another film forming agent, or a preservative or the like. A film forming agent can be an alcohol-based film forming agent, an alcohol ether-based film forming agent, or an ester-based film forming agent. Non-limiting examples of a film forming agent include a water-soluble polymer, a propanediol ether, acetate, or the like or any combination thereof. In some embodiments one or more film forming agents, including two or more, three or more, four or more, or five or more film forming agents can be added individually or collectively to a composition disclosed herein in a total amount of 0.01% to about 4% by weigh, about 0.1% to about 2% by weight, about 0.25% to about 1.5% by weigh, about 0.25% to about 1.0% by weigh, or about 0.5% to about 1.0% by weight of each of the one or more film forming agents.

A preservative is a compound or mixture of compounds that prevents decomposition of a dry powdered composition or a liquid composition disclosed herein including a paste or colloidal composition disclosed herein. In some embodiments, a preservative is added to a dry powdered composition disclosed herein to prevent its decomposition. In some embodiments, a preservative is added to a liquid composition disclosed herein including a paste or colloidal composition disclosed herein to prevent its decomposition. In some embodiments, a preservative can include characteristics of a solvent. In some embodiments, a preservative can be combined with other components, such as, e.g., a solvent, a diluent, a thickening agent, a dispersing agent, a binding agent, a foaming agent, a stabilizing agent, a film forming agent, or another preservative or the like. Non-limiting examples of a preservative includes sodium benzoate, imidazolidinyl urea, diazolidinyl urea, calcium chloride, citric acid, ascorbic acid, tartaric acid, sodium hydroxymethylglycinate (Nuosept 44), or any combination thereof. In some embodiments one or more preservatives, including two or more, three or more, four or more, or five or more preservatives can be added individually or collectively to a composition disclosed herein in a total amount of 0.01% to about 4% by weigh, about 0.1% to about 2% by weight, about 0.25% to about 1.5% by weigh, about 0.25% to about 1.0% by weigh, or about 0.5% to about 1.0% by weight of each of the one or more preservatives.

A composition disclosed herein has minimal adverse effects on humans, mammals including domestic animals, plant life and the environment. In an aspect of this embodiment, a composition disclosed herein, including a dry powdered, liquid, paste or colloidal composition disclosed herein, is substantially non-toxic to humans, mammals, plants and the environment. In other aspects of this embodiment, a composition disclosed herein, including a dry powdered, liquid, paste or colloidal composition disclosed herein, is essentially non-toxic to humans, mammals, plants and the environment. In yet other aspects of this embodiment, a composition disclosed herein, including a dry powdered, liquid, paste or colloidal composition disclosed herein, is non-toxic to humans, mammals, plants and the environment.

Aspects of the present specification disclose, in part, a composition that is biodegradable. A biodegradable composition disclosed herein, including a dry powdered, liquid, paste or colloidal composition disclosed herein, is one that is prone to degrading, eroding, resorbing, decomposing, or breaking down to a substantial or significant degree once applied according to the methods and uses disclosed herein. In aspects of this embodiment, at least 75%, at least 80%, at least 85%, at least 90%, at least 95%, at least 99% of a composition disclosed herein biodegrades in, e.g., about 1 day, about 2 days, about 3 days, about 4 days, about 5 days, about 6 days or about 7 days. In other aspects of this embodiment, at least 75%, at least 80%, at least 85%, at least 90%, at least 95%, at least 99% of a composition disclosed herein biodegrades in, e.g., about 1 to about 2 days, about 1 to about 3 days, about 1 to about 4 days, about 1 to about 5 days, about 1 to about 6 days, about 1 to about 7 days, about 2 to about 3 days, about 2 to about 4 days, about 2 to about 5 days, about 2 to about 6 days, about 2 to about 7 days, about 3 to about 4 days, about 3 to about 5 days, about 3 to about 6 days, about 3 to about 7 days, about 4 to about 5 days, about 4 to about 6 days, about 4 to about 7 days, about 5 to about 6 days, about 5 to about 7 days or about 6 to about 7 days.

In aspects of this embodiment, at least 75%, at least 80%, at least 85%, at least 90%, at least 95%, at least 99% of a composition disclosed herein biodegrades in, e.g., about 7 day, about 8 days, about 9 days, about 10 days, about 11 days, about 12 days, about 13 days or about 14 days. In other aspects of this embodiment, at least 75%, at least 80%, at least 85%, at least 90%, at least 95%, at least 99% of a composition disclosed herein biodegrades in, e.g., about 7 to about 8 days, about 7 to about 9 days, about 7 to about 10 days, about 7 to about 11 days, about 7 to about 12 days, about 7 to about 13 days, about 7 to about 14 days, about 8 to about 9 days, about 8 to about 10 days, about 8 to about 11 days, about 8 to about 12 days, about 8 to about 13 days, about 8 to about 14 days, about 9 to about 10 days, about 9 to about 11 days, about 9 to about 12 days, about 9 to about 13 days, about 9 to about 14 days, about 9 to about 11 days, about 9 to about 12 days, about 9 to about 13 days, about 9 to about 14 days, about 10 to about 11 days, about 10 to about 12 days, about 10 to about 13 days, about 10 to about 14 days, about 11 to about 12 days, about 11 to about 13 days, about 11 to about 14 days, about 12 to about 13 days, about 12 to about 14 days or about 13 to about 14 days.

In aspects of this embodiment, at least 75%, at least 80%, at least 85%, at least 90%, at least 95%, at least 99% of a liquid composition disclosed herein biodegrades in, e.g., about 15 day, about 16 days, about 17 days, about 18 days, about 19 days, about 20 days or about 21 days. In other aspects of this embodiment, at least 75%, at least 80%, at least 85%, at least 90%, at least 95%, at least 99% of a liquid composition disclosed herein biodegrades in, e.g., about 15 to about 16 days, about 15 to about 17 days, about 15 to about 18 days, about 15 to about 19 days, about 15 to about 20 days, about 15 to about 21 days, about 16 to about 17 days, about 16 to about 18 days, about 16 to about 19 days, about 16 to about 20 days, about 16 to about 21 days, about 17 to about 18 days, about 17 to about 19 days, about 17 to about 20 days, about 17 to about 21 days, about 18 to about 19 days, about 18 to about 20 days, about 18 to about 21 days, about 19 to about 20 days, about 19 to about 21 days or about 20 to about 21 days.

Aspects of the present specification disclose, in part, kits comprising one or more components useful to practice a method or use disclosed herein. Kits provide a convenient enclosure of components useful to practice a method or use disclosed herein to facilitate or enhance a commercial sale. In some embodiments, a kit comprises a dry powdered composition disclosed herein and one or more other reagents useful to practice a method or use disclosed herein, such as, e.g., one or more solvents, one or more carriers, and/or one or more diluents, thickening agents, dispersing agents, binding agents, foaming agents, stabilizing agents, film forming agents, and/or preservatives. In some embodiments, a kit comprises a dry powdered composition disclosed herein and one or more other reagents useful to practice a method or use disclosed herein, such as, e.g., one or more solvents, one or more carriers, and/or one or more diluents, thickening agents, dispersing agents, binding agents, foaming agents, stabilizing agents, film forming agents, and/or preservatives.

Kits typically provide a suitable container, e.g., a box or other enclosed carrier that contain the one or more components useful to practice a method or use disclosed herein. In addition, kits disclosed herein will typically include separate containers, e.g., a bottle, a vial, a flask or other enclosed carrier that contains the one or more components. For example, a container for a dry powder composition or a liquid composition disclosed herein, and a separate container for the one or more other reagents included in the kit. Kits can be portable, for example, able to be transported and used in a residential, commercial or industrial building, in an agricultural field or farm, or in a remote area.

A kit disclosed herein can comprise a fire extinguishing delivery or application system. The fire extinguishing delivery or application system of the kit are useful for applying a dry powdered or liquid composition disclosed herein to a site of interest, such as, e.g., a structure or an environmental area. A fire extinguishing delivery or application system disclosed herein, includes, without limitation, a mixing container, a granular dispenser, a liquid dispenser, or pellet dispenser, a storage container, or a combination thereof. A kit comprises a one or more fire extinguishing delivery or application systems such as two or more, three or more, four or more, or five or more delivery or application system. Within the kit, the fire extinguishing delivery or application system may be packaged individually, or in sets of 2 or more. The fire extinguishing delivery or application system can be packaged such that it remains sterile until use. In certain embodiments, a fire extinguishing delivery or application system disclosed herein can be packaged in plastic sheaths. Further, to prevent contamination, fire extinguishing delivery or application system disclosed herein is preferably single-use, disposable delivery or application system.

The kit can also comprise a set of instructions. Instructions include information useful to the end user for employing any of the disclosed dry powdered or liquid compositions, and practicing any of the disclosed methods or uses. For example, instructions can include information on how to mix a dry powdered composition disclosed herein with a solvent disclosed herein to form a liquid composition disclosed herein as well as any dilution instructions. In addition, instructions can provide information on how to use a fire extinguishing delivery or application system to apply a dry powdered or liquid composition disclosed herein. Such instructions can also include information indicating dosage amounts, dose frequency, duration of application, and timing criteria, such as that mixing should be done at a certain time before application, such as, e.g., just prior to use. Instructions can include information on how to apply a dry powdered or liquid composition disclosed herein directly to a site of interest, such as, e.g., an environmental area disclosed herein, and in what order the individual components should be applied to such sites of interest. Instructions can include information on how to store a dry powdered, a liquid composition, and/or a kit disclosed herein. Instructions may contain warnings on potential hazards or situations where it would not be appropriate to use the components of the kit. Instructions can include information on the individual components and identifying manufacturer information, lot numbers, manufacturer location and date. Instructions can include information on a storage conditions of a kit disclosed herein. Instructions include "printed matter" or a computer readable medium, such as a disk (e.g., hard disk, flash memory), optical disk such as CD- or DVD-ROM/RAM, DVD, MP3, magnetic tape, or an electrical storage media such as RAM and ROM or hybrids of these such as magnetic/optical storage media, FLASH media or memory type cards.

Aspects of the present specification disclose methods of controlling a fire. Additional aspects of the present specification disclose uses of a composition disclosed herein for controlling a fire. Controlling a fire includes retarding, suppressing, or extinguishing a fire already ignited, retarding, suppressing, or preventing an ignition point that creates a fire, deterring, suppressing, re-routing, or preventing a spreading of a fire into one or more areas not on fire, or any combination thereof.

The disclosed methods and uses comprises applying an effective amount of a composition disclosed herein to one or more areas where control of a fire is desired. In some embodiments, the disclosed methods and uses comprise the steps applying an effective amount of a liquid composition to one or more areas where control of a fire is desired. In some embodiments, the disclosed methods and uses comprise the steps of dissolving a dry powdered composition disclosed herein with a solvent to form a liquid composition and applying an effective amount of the liquid composition to one or more areas where control of a fire is desired. In some embodiments, the disclosed methods and uses comprise the steps applying an effective amount of a dry powdered composition to one or more areas where control of a fire is desired. In some embodiments, the disclosed methods and uses comprise the steps applying an effective amount of a paste or colloidal composition to one or more areas where control of a fire is desired. Applying an effective amount of a composition disclosed herein to one or more areas is done in a manner where a fire will be or could be exposed to a composition disclosed herein in a manner that will control a fire.

A fire is the rapid oxidation of a material in the exothermic chemical process of combustion, releasing heat, light, and various reaction products. A fire can be classified based on the combustible material or fuel source that has or could be ignited. Fires that use combustible solid substances as a fuel source, such as paper, wood, fabric, most types of trash, rubber, many plastics and other ordinary solid combustibles, are designated as Class A fires under the U.S. system. Fires that use combustible liquid, liquefiable substances or gases as a fuel source, such as gasoline, petroleum oils, tar, solvents, thinners, lacquer, oil-based products oil-based paints, are designated as Class B fires under the U.S. system. Fires that involve electrical components and/or energized equipment, such as electrical panels, fuse boxes, transformers, electrical machinery, electrical appliances, electrical motors, are designated as Class C fires under the U.S. system. Although not technically used as the fuel source of the fire, electrical components and/or energized equipment are a separate hazard that warrant a distinct fire class. Fires that use combustible metals and metal alloys as a fuel source, such as magnesium, sodium, potassium, titanium and aluminum, are designated as Class D fires under the U.S. system. Although technically a type of fire using combustible liquid as its fuel source, Class K fires are distinct enough to warrant their own classification. Fires that use combustible cooking liquids as a fuel source, such as greases, cooking oils, vegetable fat, and animal fat, are designated as Class K fires under the U.S. system.

The disclosed methods and uses are capable of controlling a fire regardless of the source of fuel. In some embodiments, a disclosed method or use of controlling a fire comprises applying an effective amount of a composition disclosed herein to control a fire caused by a combustible substance. In some embodiments, a disclosed method or use of controlling a fire comprises applying an effective amount of a composition disclosed herein to control a fire caused by a combustible solid substance. In some embodiments, a disclosed method or use of controlling a fire comprises applying an effective amount of a composition disclosed herein to control a Class A fire. In some embodiments, a disclosed method or use of controlling a fire comprises applying an effective amount of a composition disclosed herein to control a fire caused by a combustible liquid substance. In some embodiments, a disclosed method or use of controlling a fire comprises applying an effective amount of a composition disclosed herein to control a fire caused by a combustible gas substance. In some embodiments, a disclosed method or use of controlling a fire comprises applying an effective amount of a composition disclosed herein to control a Class B fire. In some embodiments, a disclosed method or use of controlling a fire comprises applying an effective amount of a composition disclosed herein to control a fire caused by a combustible substance involving an electrical component and/or an energized equipment. In some embodiments, a disclosed method or use of controlling a fire comprises applying an effective amount of a composition disclosed herein to control a Class C fire. In some embodiments, a disclosed method or use of controlling a fire comprises applying an effective amount of a composition disclosed herein to control a fire caused by a combustible metal and metal alloy. In some embodiments, a disclosed method or use of controlling a fire comprises applying an effective amount of a composition disclosed herein to control a Class D fire. In some embodiments, a disclosed method or use of controlling a fire comprises applying an effective amount of a composition disclosed herein to control a fire caused by a combustible cooking liquid. In some embodiments, a disclosed method or use of controlling a fire comprises applying an effective amount of a composition disclosed herein to control a fire caused by a combustible grease, cooking oil, vegetable fat, animal fat, or any combination thereof. In some embodiments, a disclosed method or use of controlling a fire comprises applying an effective amount of a composition disclosed herein to control a Class K fire. In some embodiments, a disclosed method or use of controlling a fire comprises applying an effective amount of a composition disclosed herein to control a wildfire (also called wildland fire, uncontrolled fire in a forest, grassland, brushland, or land sown to crops/for agriculture).

Aspects of the present specification disclose, in part, directly adding a dry powdered composition disclosed herein to one or more areas to form a liquid composition disclosed herein. In some embodiments, the disclosed methods and uses rely on liquid already present in the one or more areas to dissolve a dry powdered composition disclosed herein. For example, a dry powdered composition can be added to one or more areas like soil and a solvent like water present in the soil can dissolve the dry powdered composition to form a liquid composition disclosed herein. In another example, a dry powdered composition can be added to one or more areas and then a solvent like water can be applied to the one or more areas, thereby dissolving the dry powdered composition to form a liquid composition disclosed herein.

Upon application of a composition disclosed herein using a method or use disclosed herein, the composition disclosed herein results in an accelerated in situ chemical reactions of the molecular structures, particularly chemical bonds present in polysaccharide and lipid-based components of the one or more components present in a heat source of a fire, a fuel source of a fire, and/or an oxidizer source of a fire. These in situ chemical reactions cool a heat source of a fire, starve a fuel source of a fire and/or smother an oxidizer source of a fire, resulting in the control of the fire.

Without wishing to be limited by any theory, upon formation of a liquid, paste or colloidal composition disclosed herein, highly reactive, uniquely structured, ultra-fine microbubbles are spontaneously formed. These "functionalized" microbubbles comprise an outer "highly reactive" shell composed of one or more nonionic surfactants and components from the treated fermented microbial supernatant and an inner core containing air. The "highly reactive" shell enables a dramatic increase in the mass transfer of oxygen in an aqueous environment and an accelerated bio-catalysis of the molecular structures of compounds, which in combination provide a synergistic functionality. With respect to mass transfer of oxygen, this functionality increases transfer rates of oxygen and raises the level of dissolved oxygen in an aqueous environment which far exceeding the solubility limits anticipated by Henry's Law, and, are at levels that simply cannot be achieved through mechanical aeration systems. It appears that components from the treated fermented microbial supernatant interfere with the ability of the nonionic surfactants to create a well-organized micellar shell. The result is a loose molecular packing of these fermentation components and surfactants that "functionalized" the shell to be more gas permeable, thereby creating more favorable conditions for mass gas transfer. With respect to accelerated bio-catalysis, this functionality lowers the transition of energy required for a catalytic reaction to occur by providing a reaction platform that increases localized concentrations of reactants, enables donation of electrons and facilitate chemical reactions at electron poor sites. As such, this bio-catalysis function mediates cleavage of chemical bonds, including glycosidic and ester bonds, present in a compound. As such, the "functionalized" shell of the microbubbles have catalytic activities that are like conventional enzyme systems, but without the need of any enzymes. Thus, application of a liquid composition disclosed herein creates "functionalized" microbubbles that increase oxygen dispersion resulting in higher dissolved oxygen levels and accelerate molecular interactions resulting in catalytic breakdown of compounds.

When in contact with one or more elements of the fire tetrahedron, the "functionalized" microbubbles chemically interacts with one or more elements of the fire tetrahedron in a manner that enables donation of electrons or reactions at electron poor sites that mediates cleavage of chemical bonds, including glycosidic and ester bonds, present in the one or more elements. These interactions appear to be a form of hydrolysis using beta-oxidation where, in addition to relying on the "highly reactive" shell, oxygen present in the core of the microbubble is also utilized. Thus, the properties present in the "functionalized" microbubbles works synergistically with the oxygen transfer capabilities of the core to enhance the in situ breaking of chemical bonds, including glycosidic and ester bonds present in 1) a heat source of a fire; 2) a fuel source of a fire; and/or 3) an oxidizer source of a fire. These in situ chemical reactions cool a heat source of a fire, starve a fuel source of a fire and/or smother an oxidizer source of a fire, resulting in the control of the fire. This mechanism of action pertaining to these reactions appeared to be tied to the ability of a composition disclosed herein to absorb more heat than the fire can generate, remove a combustible material serving as a source of fuel, and/or removing an oxidizer source.

In one embodiment, a composition disclosed herein, including a dry powdered, liquid, paste or colloidal composition disclosed herein, is used in an undiluted or concentrated formulation of a dry powdered, liquid, paste or colloidal composition disclosed herein. In methods and uses applying an undiluted or concentrated formulation of a composition disclosed herein, the composition is considered a ready-to-use formulation.

In one embodiment, a composition disclosed herein, including a dry powdered, liquid, paste or colloidal composition disclosed herein, is used as a dilution of a dry powdered, liquid, paste or colloidal composition disclosed herein, such as, e.g., a dilution of an undiluted or concentrated formulation of a composition disclosed herein. In aspects of this embodiment, a composition disclosed herein is used at a composition to dilutent ratio of, e.g., about 1:1, about 1:2, about 1:3, about 1:4, about 1:5, about 1:6, about 1:7, about 1:8, about 1:9, about 1:10, about 1:15, about 1:20, about 1:25, about 1:30, about 1:40, about 1:50, about 1:60, about 1:70, about 1:80, about 1:90, or about 1:100. In other aspects of this embodiments, a composition disclosed herein is used at a composition to dilutent ratio of, e.g., at least 1:1, at least 1:2, at least 1:3, at least 1:4, at least 1:5, at least 1:6, at least 1:7, at least 1:8, at least 1:9, at least 1:10, at least 1:15, at least 1:20, at least 1:25, at least 1:30, at least 1:40, at least 1:50, at least 1:60, at least 1:70, at least 1:80, at least 1:90, or at least 1:100. In yet other aspects of this embodiments, a composition disclosed herein is used at a composition to dilutent ratio of, e.g., at most 1:1, at most 1:2, at most 1:3, at most 1:4, at most 1:5, at most 1:6, at most 1:7, at most 1:8, at most 1:9, at most 1:10, at most 1:15, at most 1:20, at most 1:25, at most 1:30, at most 1:40, at most 1:50, at most 1:60, at most 1:70, at most 1:80, at most 1:90, or at most 1:100.

In still other aspects of this embodiments, a composition disclosed herein is used at a composition to dilutent ratio of, e.g., about 1:1 to about 1:2, about 1:1 to about 1:3, about 1:1 to about 1:4, about 1:1 to about 1:5, about 1:1 to about 1:6, about 1:1 to about 1:7, about 1:1 to about 1:8, about 1:1 to about 1:9, about 1:1 to about 1:10, about 1:1 to about 1:15, about 1:1 to about 1:20, about 1:1 to about 1:25, about 1:1 to about 1:30, about 1:1 to about 1:40, about 1:1 to about 1:50, about 1:1 to about 1:60, about 1:1 to about 1:70, about 1:1 to about 1:80, about 1:1 to about 1:90, about 1:1 to about 1:100, about 1:2 to about 1:3, about 1:2 to about 1:4, about 1:2 to about 1:5, about 1:2 to about 1:6, about 1:2 to about 1:7, about 1:2 to about 1:8, about 1:2 to about 1:9, about 1:2 to about 1:10, about 1:2 to about 1:15, about 1:2 to about 1:20, about 1:2 to about 1:25, about 1:2 to about 1:30, about 1:2 to about 1:40, about 1:2 to about 1:50, about 1:2 to about 1:60, about 1:2 to about 1:70, about 1:2 to about 1:80, about 1:2 to about 1:90, about 1:2 to about 1:100, about 1:3 to about 1:4, about 1:3 to about 1:5, about 1:3 to about 1:6, about 1:3 to about 1:7, about 1:3 to about 1:8, about 1:3 to about 1:9, about 1:3 to about 1:10, about 1:3 to about 1:15, about 1:3 to about 1:20, about 1:3 to about 1:25, about 1:3 to about 1:30, about 1:3 to about 1:40, about 1:3 to about 1:50, about 1:3 to about 1:60, about 1:3 to about 1:70, about 1:3 to about 1:80, about 1:3 to about 1:90, about 1:3 to about 1:100, about 1:4 to about 1:5, about 1:4 to about 1:6, about 1:4 to about 1:7, about 1:4 to about 1:8, about 1:4 to about 1:9, about 1:4 to about 1:10, about 1:4 to about 1:15, about 1:4 to about 1:20, about 1:4 to about 1:25, about 1:4 to about 1:30, about 1:4 to about 1:40, about 1:4 to about 1:50, about 1:4 to about 1:60, about 1:4 to about 1:70, about 1:4 to about 1:80, about 1:4 to about 1:90, about 1:4 to about 1:100, about 1:5 to about 1:6, about 1:5 to about 1:7, about 1:5 to about 1:8, about 1:5 to about 1:9, about 1:5 to about 1:10, about 1:5 to about 1:15, about 1:5 to about 1:20, about 1:5 to about 1:25, about 1:5 to about 1:30, about 1:5 to about 1:40, about 1:5 to about 1:50, about 1:5 to about 1:60, about 1:5 to about 1:70, about 1:5 to about 1:80, about 1:5 to about 1:90, about 1:5 to about 1:100, about 1:6 to about 1:7, about 1:6 to about 1:8, about 1:6 to about 1:9, about 1:6 to about 1:10, about 1:6 to about 1:15, about 1:6 to about 1:20, about 1:6 to about 1:25, about 1:6 to about 1:30, about 1:6 to about 1:40, about 1:6 to about 1:50, about 1:6 to about 1:60, about 1:6 to about 1:70, about 1:6 to about 1:80, about 1:6 to about 1:90, about 1:6 to about 1:100, about 1:7 to about 1:8, about 1:7 to about 1:9, about 1:7 to about 1:10, about 1:7 to about 1:15, about 1:7 to about 1:20, about 1:7 to about 1:25, about 1:7 to about 1:30, about 1:7 to about 1:40, about 1:7 to about 1:50, about 1:7 to about 1:60, about 1:7 to about 1:70, about 1:7 to about 1:80, about 1:7 to about 1:90, about 1:7 to about 1:100, about 1:8 to about 1:9, about 1:8 to about 1:10, about 1:8 to about 1:15, about 1:8 to about 1:20, about 1:8 to about 1:25, about 1:8 to about 1:30, about 1:8 to about 1:40, about 1:8 to about 1:50, about 1:8 to about 1:60, about 1:8 to about 1:70, about 1:8 to about 1:80, about 1:8 to about 1:90, about 1:8 to about 1:100, about 1:9 to about 1:10, about 1:9 to about 1:15, about 1:9 to about 1:20, about 1:9 to about 1:25, about 1:9 to about 1:30, about 1:9 to about 1:40, about 1:9 to about 1:50, about 1:9 to about 1:60, about 1:9 to about 1:70, about 1:9 to about 1:80, about 1:9 to about 1:90, about 1:9 to about 1:100, about 1:10 to about 1:15, about 1:10 to about 1:20, about 1:10 to about 1:25, about 1:10 to about 1:30, about 1:10 to about 1:40, about 1:10 to about 1:50, about 1:10 to about 1:60, about 1:10 to about 1:70, about 1:10 to about 1:80, about 1:10 to about 1:90, or about 1:10 to about 1:100.

In other aspects of this embodiments, a composition disclosed herein is used at a composition to dilutent ratio of, e.g., about 1:15 to about 1:20, about 1:15 to about 1:25, about 1:15 to about 1:30, about 1:15 to about 1:40, about 1:15 to about 1:50, about 1:15 to about 1:60, about 1:15 to about 1:70, about 1:15 to about 1:80, about 1:15 to about 1:90, about 1:15 to about 1:100, about 1:20 to about 1:25, about 1:20 to about 1:30, about 1:20 to about 1:40, about 1:20 to about 1:50, about 1:20 to about 1:60, about 1:20 to about 1:70, about 1:20 to about 1:80, about 1:20 to about 1:90, about 1:20 to about 1:100, about 1:30 to about 1:40, about 1:30 to about 1:50, about 1:30 to about 1:60, about 1:30 to about 1:70, about 1:30 to about 1:80, about 1:30 to about 1:90, about 1:30 to about 1:100, about 1:40 to about 1:50, about 1:40 to about 1:60, about 1:40 to about 1:70, about 1:40 to about 1:80, about 1:40 to about 1:90, about 1:40 to about 1:100, about 1:50 to about 1:60, about 1:50 to about 1:70, about 1:50 to about 1:80, about 1:50 to about 1:90, about 1:50 to about 1:100, about 1:60 to about 1:70, about 1:60 to about 1:80, about 1:60 to about 1:90, about 1:60 to about 1:100, about 1:70 to about 1:80, about 1:70 to about 1:90, about 1:70 to about 1:100, about 1:80 to about 1:90, about 1:80 to about 1:100, or about 1:80 to about 1:100.

In one embodiment, a composition disclosed herein, including a dry powdered, liquid, paste or colloidal composition disclosed herein, is used at a final concentration of 0.01% to 100%. In aspects of this embodiment, a composition disclosed herein is used at a final concentration by weight of, e.g., about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9% or about 10%. In other aspects of this embodiment, a composition disclosed herein is used at a final concentration by weight of, e.g., at least 0.01%, at least 0.02%, at least 0.03%, at least 0.04%, at least 0.05%, at least 0.06%, at least 0.07%, at least 0.08%, at least 0.09%, at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9% or at least 10%. In yet other aspects of this embodiment, a composition disclosed herein is used at a final concentration by weight of, e.g., at most 0.01%, at most 0.02%, at most 0.03%, at most 0.04%, at most 0.05%, at most 0.06%, at most 0.07%, at most 0.08%, at most 0.09%, at most 0.1%, at most 0.2%, at most 0.3%, at most 0.4%, at most 0.5%, at most 0.6%, at most 0.7%, at most 0.8%, at most 0.9%, at most 1%, at most 2%, at most 3%, at most 4%, at most 5%, at most 6%, at most 7%, at most 8%, at most 9% or at most 10%.

In aspects of this embodiment, a composition disclosed herein is used at a final concentration by weight of, e.g., about 0.01% to about 0.05%, about 0.01% to about 0.1%, about 0.01% to about 0.25%, about 0.01% to about 0.5%, about 0.01% to about 0.75%, about 0.01% to about 1%, about 0.01% to about 1.5%, about 0.01% to about 2%, about 0.01% to about 2.5%, about 0.01% to about 3%, about 0.01% to about 3.5%, about 0.01% to about 4%, about 0.01% to about 4.5%, about 0.01% to about 5%, about 0.05% to about 0.1%, about 0.05% to about 0.25%, about 0.05% to about 0.5%, about 0.05% to about 0.75%, about 0.05% to about 1%, about 0.05% to about 1.5%, about 0.05% to about 2%, about 0.05% to about 2.5%, about 0.05% to about 3%, about 0.05% to about 3.5%, about 0.05% to about 4%, about 0.05% to about 4.5%, about 0.05% to about 5%, about 0.1% to about 0.25%, about 0.1% to about 0.5%, about 0.1% to about 0.75%, about 0.1% to about 1%, about 0.1% to about 1.5%, about 0.1% to about 2%, about 0.1% to about 2.5%, about 0.1% to about 3%, about 0.1% to about 3.5%, about 0.1% to about 4%, about 0.1% to about 4.5%, about 0.1% to about 5%, about 0.25% to about 0.5%, about 0.25% to about 0.75%, about 0.25% to about 1%, about 0.25% to about 1.5%, about 0.25% to about 2%, about 0.25% to about 2.5%, about 0.25% to about 3%, about 0.25% to about 3.5%, about 0.25% to about 4%, about 0.25% to about 4.5%, about 0.25% to about 5%, about 0.5% to about 0.75%, about 0.5% to about 1%, about 0.5% to about 1.5%, about 0.5% to about 2%, about 0.5% to about 2.5%, about 0.5% to about 3%, about 0.5% to about 3.5%, about 0.5% to about 4%, about 0.5% to about 4.5%, about 0.5% to about 5%, about 0.75% to about 1%, about 0.75% to about 1.5%, about 0.75% to about 2%, about 0.75% to about 2.5%, about 0.75% to about 3%, about 0.75% to about 3.5%, about 0.75% to about 4%, about 0.75% to about 4.5%, about 0.75% to about 5%, about 1% to about 5%, about 1% to about 10% or about 5% to about 10%.

In aspects of this embodiment, a composition disclosed herein is used at a final concentration by weight of, e.g., about 10%, about 20%, about 30%, about 40%, about 50%, about 60%, about 70%, about 80%, about 90%, about 95%, or about 100%. In other aspects of this embodiment, an effective amount of a composition disclosed herein has a final concentration by weight of, e.g., at least 10%, at least 20%, at least 30%, at least 40%, at least 50%, at least 60%, at least 70%, at least 80%, at least 90%, at least 95%, or at least 100%. In yet other aspects of this embodiment, an effective amount of a composition disclosed herein has a final concentration by weight of, e.g., at most 10%, at most 20%, at most 30%, at most 40%, at most 50%, at most 60%, at most 70%, at most 80%, at most 90%, at most 95%, or at most 100%.

In yet other aspects of this embodiment, a composition disclosed herein is used at a final concentration by weight of, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, or about 90% to about 100%.

Whether an undiluted or diluted form, application of a composition, disclosed herein in controlling a fire is in an effective amount. An effective amount of a disclosed composition can be 1) an amount sufficient to cool a heat source of a fire, starve a fuel source of a fire and/or smother an oxidizer source of a fire in order to retard, suppress, and/or extinguish a fire already ignited; 2) an amount sufficient to cool a heat source of a fire, starve a fuel source of a fire and/or smother an oxidizer source of a fire in order to retard, suppress, and/or prevent an ignition point from creating a fire; 3) an amount sufficient to cool a heat source of a fire, starve a fuel source of a fire and/or smother an oxidizer source of a fire in order to deter, suppress, re-route, and/or prevent a fire from spreading to one or more areas not on fire. The actual effective amount of a disclosed composition is determined by routine screening procedures employed to evaluate controlling activity and efficacy of a composition disclosed herein in controlling a fire. Such screening procedures are well known by those skilled in the art. It is expected that a composition disclosed herein having a higher level of fire controlling activity (i.e., fire extinguishing capability) can be used in smaller amounts and concentrations, while a composition disclosed herein having a lower level of fire controlling activity may require larger amounts or concentrations in order to achieve the same controlling effect. Such amounts can be determined by routine assays/measurements of fire extinguishing effectiveness/activity. Exemplary fire extinguishing performance testing methods are known in the art and can be employed, examples of which can be found in U.S. Pat. Nos. 9,776,029; 9,974,992; 10,434,348 and 10,518,120 each of which is hereby incorporated by reference in its entirety. As one example, fire extinguishing performance can be evaluated by measuring fire-extinguishing speed, which is calculated as a time required for extinguishing a fire, and a fire-extinguishing efficiency, i.e. a degree of fire reduction of a fire extinguishing composition, which is calculated from an amount of a fire extinguishing composition, here a compositions disclosed herein as compared to conventional fire extinguishing compositions, to extinguish a fire.

In aspects of this embodiment, an effective amount of a disclosed composition is an amount sufficient an amount sufficient to cool a heat source of a fire, starve a fuel source of a fire and/or smother an oxidizer source of a fire in order to retard, suppress, and/or extinguish a fire already ignited by, e.g., at least about 10%, about 15%, about 20%, about 25%, about 30%, about 35%, about 40%, about 45%, about 50%, about 55%, about 60%, about 65%, about 70%, about 75%, about 80%, about 85%, about 90% or about 95%. In other aspects of this embodiment, an effective amount of a disclosed composition is an amount sufficient an amount sufficient to cool a heat source of a fire, starve a fuel source of a fire and/or smother an oxidizer source of a fire in order to retard, suppress, and/or extinguish a fire already ignited by, e.g., of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In still other aspects of this embodiment, an effective amount of a disclosed composition is an amount sufficient an amount sufficient to cool a heat source of a fire, starve a fuel source of a fire and/or smother an oxidizer source of a fire in order to retard, suppress, and/or extinguish a fire already ignited by, e.g., of about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, about 90% to about 95% or about 95% to about 100%.

In aspects of this embodiment, an effective amount of a disclosed composition is an amount sufficient to cool a heat source of a fire, starve a fuel source of a fire and/or smother an oxidizer source of a fire in order to retard, suppress, and/or prevent an ignition point from creating a fire by, e.g., at least about 10%, about 15%, about 20%, about 25%, about 30%, about 35%, about 40%, about 45%, about 50%, about 55%, about 60%, about 65%, about 70%, about 75%, about 80%, about 85%, about 90% or about 95%. In other aspects of this embodiment, an effective amount of a disclosed composition is an amount sufficient to cool a heat source of a fire, starve a fuel source of a fire and/or smother an oxidizer source of a fire in order to retard, suppress, and/or prevent an ignition point from creating a fire by, e.g., of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In still other aspects of this embodiment, an effective amount of a disclosed composition is an amount sufficient to cool a heat source of a fire, starve a fuel source of a fire and/or smother an oxidizer source of a fire in order to retard, suppress, and/or prevent an ignition point from creating a fire by, e.g., of about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, about 90% to about 95% or about 95% to about 100%.

In aspects of this embodiment, an effective amount of a disclosed composition is an amount sufficient to cool a heat source of a fire, starve a fuel source of a fire and/or smother an oxidizer source of a fire in order to deter, suppress, re-route, and/or prevent a fire from spreading to one or more areas not on fire by, e.g., at least about 10%, about 15%, about 20%, about 25%, about 30%, about 35%, about 40%, about 45%, about 50%, about 55%, about 60%, about 65%, about 70%, about 75%, about 80%, about 85%, about 90% or about 95%. In other aspects of this embodiment, an effective amount of a disclosed composition is an amount sufficient to cool a heat source of a fire, starve a fuel source of a fire and/or smother an oxidizer source of a fire in order to deter, suppress, re-route, and/or prevent a fire from spreading to one or more areas not on fire by, e.g., of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In still other aspects of this embodiment, an amount sufficient to cool a heat source of a fire, starve a fuel source of a fire and/or smother an oxidizer source of a fire in order to deter, suppress, re-route, and/or prevent a fire from spreading to one or more areas not on fire by, e.g., of about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, about 90% to about 95% or about 95% to about 100%.

In one embodiment, an effective amount of a composition disclosed herein, including a dry powdered, liquid, paste or colloidal composition disclosed herein, is a composition (g or L) to area size (m$^2$) ratio of, e.g., about 1:1 to about 1:5,000. An area size is the surface area of the one or more areas a composition disclosed herein is applied to achieve the desired fire controlling effect of a method or use disclosed herein. The composition to area size ratios are typically amounts that are an effective amount for the disclosed methods and uses of controlling a fire.

In aspects of this embodiments, an effective amount of a composition disclosed herein is a composition (g or L) to area size (m$^2$) ratio of, e.g., about 1:1, about 1:2, about 1:3, about 1:4, about 1:5, about 1:6, about 1:7, about 1:8, about 1:9, about 1:10, about 1:15, about 1:20, about 1:25, about 1:30, about 1:40, about 1:50, about 1:60, about 1:70, about 1:80, about 1:90, or about 1:100. In other aspects of this embodiments, an effective amount of a composition disclosed herein is a composition (g or L) to area size (m$^2$) ratio of, e.g., at least 1:1, at least 1:2, at least 1:3, at least 1:4, at least 1:5, at least 1:6, at least 1:7, at least 1:8, at least 1:9, at least 1:10, at least 1:15, at least 1:20, at least 1:25, at least 1:30, at least 1:40, at least 1:50, at least 1:60, at least 1:70, at least 1:80, at least 1:90, or at least 1:100. In yet other aspects of this embodiments, an effective amount of a composition disclosed herein is a composition (g or L) to area size (m$^2$) ratio of, e.g., at most 1:1, at most 1:2, at most 1:3, at most 1:4, at most 1:5, at most 1:6, at most 1:7, at most 1:8, at most 1:9, at most 1:10, at most 1:15, at most 1:20, at most 1:25, at most 1:30, at most 1:40, at most 1:50, at most 1:60, at most 1:70, at most 1:80, at most 1:90, or at most 1:100.

In still other aspects of this embodiments, an effective amount of a composition disclosed herein is a composition (g or L) to area size (m$^2$) ratio of, e.g., about 1:1 to about 1:2, about 1:1 to about 1:3, about 1:1 to about 1:4, about 1:1 to about 1:5, about 1:1 to about 1:6, about 1:1 to about 1:7, about 1:1 to about 1:8, about 1:1 to about 1:9, about 1:1 to about 1:10, about 1:1 to about 1:15, about 1:1 to about 1:20, about 1:1 to about 1:25, about 1:1 to about 1:30, about 1:1 to about 1:40, about 1:1 to about 1:50, about 1:1 to about 1:60, about 1:1 to about 1:70, about 1:1 to about 1:80, about 1:1 to about 1:90, about 1:1 to about 1:100, about 1:2 to about 1:3, about 1:2 to about 1:4, about 1:2 to about 1:5, about 1:2 to about 1:6, about 1:2 to about 1:7, about 1:2 to about 1:8, about 1:2 to about 1:9, about 1:2 to about 1:10, about 1:2 to about 1:15, about 1:2 to about 1:20, about 1:2 to about 1:25, about 1:2 to about 1:30, about 1:2 to about 1:40, about 1:2 to about 1:50, about 1:2 to about 1:60, about 1:2 to about 1:70, about 1:2 to about 1:80, about 1:2 to about 1:90, about 1:2 to about 1:100, about 1:3 to about 1:4, about 1:3 to about 1:5, about 1:3 to about 1:6, about 1:3 to about 1:7, about 1:3 to about 1:8, about 1:3 to about 1:9, about 1:3 to about 1:10, about 1:3 to about 1:15, about 1:3 to about 1:20, about 1:3 to about 1:25, about 1:3 to about 1:30, about 1:3 to about 1:40, about 1:3 to about 1:50, about 1:3 to about 1:60, about 1:3 to about 1:70, about 1:3 to about 1:80, about 1:3 to about 1:90, about 1:3 to about 1:100, about 1:4 to about 1:5, about 1:4 to about 1:6, about 1:4 to about 1:7, about 1:4 to about 1:8, about 1:4 to about 1:9, about 1:4 to about 1:10, about 1:4 to about 1:15, about 1:4 to about 1:20, about 1:4 to about 1:25, about 1:4 to about 1:30, about 1:4 to about 1:40, about 1:4 to about 1:50, about 1:4 to about 1:60, about 1:4 to about 1:70, about 1:4 to about 1:80, about 1:4 to about 1:90, about 1:4 to about 1:100, about 1:5 to about 1:6, about 1:5 to about 1:7, about 1:5 to about 1:8, about 1:5 to about 1:9, about 1:5 to about 1:10, about 1:5 to about 1:15, about 1:5 to about 1:20, about 1:5 to about 1:25, about 1:5 to about 1:30, about 1:5 to about 1:40, about 1:5 to about 1:50, about 1:5 to about 1:60, about 1:5 to about 1:70, about 1:5 to about 1:80, about 1:5 to about 1:90, about 1:5 to about 1:100, about 1:6 to about 1:7, about 1:6 to about 1:8, about 1:6 to about 1:9, about 1:6 to about 1:10, about 1:6 to about 1:15, about 1:6 to about 1:20, about 1:6 to about 1:25, about 1:6 to about 1:30, about 1:6 to about 1:40, about 1:6 to about 1:50, about 1:6 to about 1:60, about 1:6 to about 1:70, about 1:6 to about 1:80, about 1:6 to about 1:90, about 1:6 to about 1:100, about 1:7 to about 1:8, about 1:7 to about 1:9, about 1:7 to about 1:10, about 1:7 to about 1:15, about 1:7 to about 1:20, about 1:7 to about 1:25, about 1:7 to about 1:30, about 1:7 to about 1:40, about 1:7 to about 1:50, about 1:7 to about 1:60, about 1:7 to about 1:70, about 1:7 to about 1:80, about 1:7 to about 1:90, about 1:7 to about 1:100, about 1:8 to about 1:9, about 1:8 to about 1:10, about 1:8 to about 1:15, about 1:8 to about 1:20, about 1:8 to about 1:25, about 1:8 to about 1:30, about 1:8 to about 1:40, about 1:8 to about 1:50, about 1:8 to about 1:60, about 1:8 to about 1:70, about 1:8 to about 1:80, about 1:8 to about 1:90, about 1:8 to about 1:100, about 1:9 to about 1:10, about 1:9 to about 1:15, about 1:9 to about 1:20, about 1:9 to about 1:25, about 1:9 to about 1:30, about 1:9 to about 1:40, about 1:9 to about 1:50, about 1:9 to about 1:60, about 1:9 to about 1:70, about 1:9 to about 1:80, about 1:9 to about 1:90, about 1:9 to about 1:100, about 1:10 to about 1:15, about 1:10 to about 1:20, about 1:10 to about 1:25, about 1:10 to about 1:30, about 1:10 to about 1:40, about 1:10 to about 1:50, about 1:10 to about 1:60, about 1:10 to about 1:70, about 1:10 to about 1:80, about 1:10 to about 1:90, or about 1:10 to about 1:100.

In other aspects of this embodiment, an effective amount of a composition disclosed herein is a composition (g or L) to area size (m$^2$) ratio of, e.g., about 1:15 to about 1:20, about 1:15 to about 1:25, about 1:15 to about 1:30, about 1:15 to about 1:40, about 1:15 to about 1:50, about 1:15 to about 1:60, about 1:15 to about 1:70, about 1:15 to about 1:80, about 1:15 to about 1:90, about 1:15 to about 1:100, about 1:20 to about 1:25, about 1:20 to about 1:30, about 1:20 to about 1:40, about 1:20 to about 1:50, about 1:20 to about 1:60, about 1:20 to about 1:70, about 1:20 to about 1:80, about 1:20 to about 1:90, about 1:20 to about 1:100, about 1:30 to about 1:40, about 1:30 to about 1:50, about 1:30 to about 1:60, about 1:30 to about 1:70, about 1:30 to about 1:80, about 1:30 to about 1:90, about 1:30 to about 1:100, about 1:40 to about 1:50, about 1:40 to about 1:60, about 1:40 to about 1:70, about 1:40 to about 1:80, about 1:40 to about 1:90, about 1:40 to about 1:100, about 1:50 to about 1:60, about 1:50 to about 1:70, about 1:50 to about 1:80, about 1:50 to about 1:90, about 1:50 to about 1:100, about 1:60 to about 1:70, about 1:60 to about 1:80, about 1:60 to about 1:90, about 1:60 to about 1:100, about 1:70 to about 1:80, about 1:70 to about 1:90, about 1:70 to about 1:100, about 1:80 to about 1:90, about 1:80 to about 1:100, or about 1:80 to about 1:100.

In one embodiment, an effective amount of a composition disclosed herein, including a dry powder, paste or colloidal composition disclosed herein, is applied at an application rate of 1 L/min/m$^2$ to 500 L/min/m$^2$. In aspects of this embodiment, an effective amount of a composition disclosed herein, including a dry powder, paste or colloidal composition disclosed herein, is applied at an application rate of, e.g., about 0.25 kg/min/m$^2$, about 0.5 kg/min/m$^2$, about 0.75 kg/min/m$^2$, about 1.0 kg/min/m$^2$, about 2.0 kg/min/m$^2$, about 3.0 kg/min/m$^2$, about 4.0 kg/min/m$^2$, about 5.0 kg/min/m$^2$, or about 10.0 kg/min/m$^2$. In other aspects of this embodiment, an effective amount of a composition disclosed herein, including a dry powder, paste or colloidal composition disclosed herein, is applied at an application rate of, e.g., at least 0.25 kg/min/m$^2$, at least 0.5 kg/min/m$^2$, at least 0.75 kg/min/m$^2$, at least 1.0 kg/min/m$^2$, at least 2.0 kg/min/m$^2$, at least 3.0 kg/min/m$^2$, at least 4.0 kg/min/m$^2$, at least 5.0 kg/min/m$^2$, or at least 10.0 kg/min/m$^2$. In yet other aspects of this embodiment, an effective amount of a composition disclosed herein is applied at an application rate of, e.g., at most 0.25 kg/min/m$^2$, at most 0.5 kg/min/m$^2$, at most 0.75 kg/min/m$^2$, at most 1.0 kg/min/m$^2$, at most 2.0 kg/min/m$^2$, at most 3.0 kg/min/m$^2$, at most 4.0 kg/min/m$^2$, at most 5.0 kg/min/m$^2$, or at most 10.0 kg/min/m$^2$.

In still other aspects of this embodiment, an effective amount of a composition disclosed herein is applied at an application rate of, e.g., about 0.25 kg/min/m$^2$ to about 0.5 kg/min/m$^2$, about 0.25 kg/min/m$^2$ to about 1.0 kg/min/m$^2$, about 0.25 kg/min/m$^2$ to about 2.0 kg/min/m$^2$, about 0.25 kg/min/m$^2$ to about 3.0 kg/min/m$^2$, about 0.25 kg/min/m$^2$ to about 4.0 kg/min/m$^2$, about 0.25 kg/min/m$^2$ to about 5.0 kg/min/m$^2$, about 0.25 kg/min/m$^2$ to about 10.0 kg/min/m$^2$, about 0.5 kg/min/m$^2$ to about 1.0 kg/min/m$^2$, about 0.5 kg/min/m$^2$ to about 2.0 kg/min/m$^2$, about 0.5 kg/min/m$^2$ to about 3.0 kg/min/m$^2$, about 0.5 kg/min/m$^2$ to about 4.0 kg/min/m$^2$, about 0.5 kg/min/m$^2$ to about 5.0 kg/min/m$^2$, about 0.5 kg/min/m$^2$ to about 10.0 kg/min/m$^2$, about 1.0 kg/min/m$^2$ to about 2.0 kg/min/m$^2$, about 1.0 kg/min/m$^2$ to about 3.0 kg/min/m$^2$, about 1.0 kg/min/m$^2$ to about 4.0 kg/min/m$^2$, about 1.0 kg/min/m$^2$ to about 5.0 kg/min/m$^2$, about 1.0 kg/min/m$^2$ to about 10.0 kg/min/m$^2$, about 2.0 kg/min/m$^2$ to about 3.0 kg/min/m$^2$, about 2.0 kg/min/m$^2$ to about 4.0 kg/min/m$^2$, about 2.0 kg/min/m$^2$ to about 5.0 kg/min/m$^2$, about 2.0 kg/min/m$^2$ to about 10.0 kg/min/m$^2$, about 3.0 kg/min/m$^2$ to about 4.0 kg/min/m$^2$, about 3.0 kg/min/m$^2$ to about 5.0 kg/min/m$^2$, about 3.0 kg/min/m$^2$ to about 10.0 kg/min/m$^2$, about 4.0 kg/min/m$^2$ to about 5.0 kg/min/m$^2$, about 4.0 kg/min/m$^2$ to about 10.0 kg/min/m$^2$, or about 5.0 kg/min/m$^2$ to about 10.0 kg/min/m$^2$.

In one embodiment, an effective amount of a composition disclosed herein, including a liquid, paste or colloidal composition disclosed herein, is applied at an application rate of 1 L/min/m$^2$ to 500 L/min/m$^2$. In aspects of this embodiment, an effective amount of a composition disclosed herein is applied at an application rate of, e.g., about 1 L/min/m$^2$, about 2 L/min/m$^2$, about 3 L/min/m$^2$, about 4 L/min/m$^2$, about 5 L/min/m$^2$, about 6 L/min/m$^2$, about 7 L/min/m$^2$, about 8 L/min/m$^2$, about 9 L/min/m$^2$, about 10 L/min/m$^2$, about 11 L/min/m$^2$, about 12 L/min/m$^2$, about 13 L/min/m$^2$, about 14 L/min/m$^2$, about 15 L/min/m$^2$, about 16 L/min/m$^2$, about 17 L/min/m$^2$, about 18 L/min/m$^2$, about 19 L/min/m$^2$, or about 20 L/min/m$^2$. In other aspects of this embodiment, an effective amount of a composition disclosed herein, including a liquid, paste or colloidal composition disclosed herein, is applied at an application rate of, e.g., at least 1 L/min/m$^2$, at least 2 L/min/m$^2$, at least 3 L/min/m$^2$, at least 4 L/min/m$^2$, at least 5 L/min/m$^2$, at least 6 L/min/m$^2$, at least 7 L/min/m$^2$, at least 8 L/min/m$^2$, at least 9 L/min/m$^2$, at least 10 L/min/m$^2$, at least 11 L/min/m$^2$, at least 12 L/min/m$^2$, at least 13 L/min/m$^2$, at least 14 L/min/m$^2$, at least 15 L/min/m$^2$, at least 16 L/min/m$^2$, at least 17 L/min/m$^2$, at least 18 L/min/m$^2$, at least 19 L/min/m$^2$, or at least 20 L/min/m$^2$. In yet other aspects of this embodiment, an effective amount of a composition disclosed herein, including a liquid, paste or colloidal composition disclosed herein, is applied at an application rate of, e.g., at most 1 L/min/m$^2$, at most 2 L/min/m$^2$, at most 3 L/min/m$^2$, at most 4 L/min/m$^2$, at most 5 L/min/m$^2$, at most 6 L/min/m$^2$, at most 7 L/min/m$^2$, at most 8 L/min/m$^2$, at most 9 L/min/m$^2$, at most 10 L/min/m$^2$, at most 11 L/min/m$^2$, at most 12 L/min/m$^2$, at most 13 L/min/m$^2$, at most 14 L/min/m$^2$, at most 15 L/min/m$^2$, at most 16 L/min/m$^2$, at most 17 L/min/m$^2$, at most 18 L/min/m$^2$, at most 19 L/min/m$^2$, or at most 20 L/min/m$^2$. In still other aspects of this embodiment, an effective amount of a composition disclosed herein, including a liquid, paste or colloidal composition disclosed herein, is applied at an application rate of, e.g., about 1 L/min/m$^2$ to about 2.5 L/min/m$^2$, about 1 L/min/m$^2$ to about 5 L/min/m$^2$, about 1 L/min/m$^2$ to about 7.5 L/min/m$^2$, about 1 L/min/m$^2$ to about 10 L/min/m$^2$, about 1 L/min/m$^2$ to about 12.5 L/min/m$^2$, about 1 L/min/m$^2$ to about 15 L/min/m$^2$, about 1 L/min/m$^2$ to about 17.5 L/min/m$^2$, about 1 L/min/m$^2$ to about 20 L/min/m$^2$, about 2.5 L/min/m$^2$ to about 5 L/min/m$^2$, about 2.5 L/min/m$^2$ to about 7.5 L/min/m$^2$, about 2.5 L/min/m$^2$ to about 10 L/min/m$^2$, about 2.5 L/min/m$^2$ to about 12.5 L/min/m$^2$, about 2.5 L/min/m$^2$ to about 15 L/min/m$^2$, about 2.5 L/min/m$^2$ to about 17.5 L/min/m$^2$, about 2.5 L/min/m$^2$ to about 20 L/min/m$^2$, about 5 L/min/m$^2$ to about 7.5 L/min/m$^2$, about 5 L/min/m$^2$ to about 10 L/min/m$^2$, about 5 L/min/m$^2$ to about 12.5 L/min/m$^2$, about 5 L/min/m$^2$ to about 15 L/min/m$^2$, about 5 L/min/m$^2$ to about 17.5 L/min/m$^2$, about 5 L/min/m$^2$ to about 20 L/min/m$^2$, about 7.5 L/min/m$^2$ to about 10 L/min/m$^2$, about 7.5 L/min/m$^2$ to about 12.5 L/min/m$^2$, about 7.5 L/min/m$^2$ to about 15 L/min/m$^2$, about 7.5 L/min/m$^2$ to about 17.5 L/min/m$^2$, about 7.5 L/min/m$^2$ to about 20 L/min/m$^2$, about 10 L/min/m$^2$ to about 12.5 L/min/m$^2$, about 10 L/min/m$^2$ to about 15

L/min/m², about 10 L/min/m² to about 17.5 L/min/m², about 10 L/min/m² to about 20 L/min/m², about 12.5 L/min/m² to about 15 L/min/m², about 12.5 L/min/m² to about 17.5 L/min/m², about 12.5 L/min/m² to about 20 L/min/m², about 15 L/min/m² to about 17.5 L/min/m², about 15 L/min/in to about 20 L/min/m², or about 17.5 L/min/in to about 20 L/min/m².

In aspects of this embodiment, an effective amount of a composition disclosed herein, including a liquid, paste or colloidal composition disclosed herein, is applied at an application rate of, e.g., about 20 L/min/m², about 30 L/min/m², about 40 L/min/m², about 50 L/min/m², about 60 L/min/m², about 70 L/min/m², about 80 L/min/m², about 90 L/min/m², about 100 L/min/m², about 125 L/min/m², about 150 L/min/m², about 175 L/min/m², about 200 L/min/m², about 225 L/min/m², about 250 L/min/m², about 275 L/min/m², about 300 L/min/m², about 325 L/min/m², or about 350 L/min/m². In other aspects of this embodiment, an effective amount of a composition disclosed herein is applied at an application rate of, e.g., at least 20 L/min/m², at least 30 L/min/m², at least 40 L/min/m², at least 50 L/min/m², at least 60 L/min/m², at least 70 L/min/m², at least 80 L/min/m², at least 90 L/min/m², at least 100 L/min/m², at least 125 L/min/m², at least 150 L/min/m², at least 175 L/min/m², at least 200 L/min/m², at least 225 L/min/m², at least 250 L/min/m², at least 275 L/min/m², at least 300 L/min/m², at least 325 L/min/m², or at least 350 L/min/m². In yet other aspects of this embodiment, an effective amount of a composition disclosed herein is applied at an application rate of, e.g., at most 20 L/min/m², at most 30 L/min/m², at most 40 L/min/m², at most 50 L/min/m², at most 60 L/min/m², at most 70 L/min/m², at most 80 L/min/m², at most 90 L/min/m², at most 100 L/min/m², at most 125 L/min/m², at most 150 L/min/m², at most 175 L/min/m², at most 200 L/min/m², at most 225 L/min/m², at most 250 L/min/m², at most 275 L/min/m², at most 300 L/min/m², at most 325 L/min/m², or at most 350 L/min/m².

In still other aspects of this embodiment, an effective amount of a composition disclosed herein, including a liquid, paste or colloidal composition disclosed herein, is applied at an application rate of, e.g., about 20 L/min/m² to about 30 L/min/m², about 20 L/min/m² to about 40 L/min/m², about 20 L/min/m² to about 40 L/min/m², about 20 L/min/m² to about 50 L/min/m², about 20 L/min/m² to about 60 L/min/m², about 20 L/min/m² to about 70 L/min/m², about 20 L/min/m² to about 80 L/min/m², about 20 L/min/m² to about 90 L/min/m², about 20 L/min/m² to about 100 L/min/m², about 20 L/min/m² to about 125 L/min/m², about 20 L/min/m² to about 150 L/min/m², about 20 L/min/m² to about 175 L/min/m², about 20 L/min/m² to about 200 L/min/m², about 20 L/min/m² to about 225 L/min/m², about 20 L/min/m² to about 250 L/min/m², about 20 L/min/m² to about 275 L/min/m², about 20 L/min/m² to about 300 L/min/m², about 20 L/min/m² to about 325 L/min/m², about 20 L/min/m² to about 350 L/min/m², about 30 L/min/m² to about 40 L/min/m², about 30 L/min/m² to about 40 L/min/m², about 30 L/min/m² to about 50 L/min/m², about 30 L/min/m² to about 60 L/min/m², about 30 L/min/m² to about 70 L/min/m², about 30 L/min/m² to about 80 L/min/m², about 30 L/min/m² to about 90 L/min/m², about 30 L/min/m² to about 100 L/min/m², about 30 L/min/m² to about 125 L/min/m², about 30 L/min/m² to about 150 L/min/m², about 30 L/min/m² to about 175 L/min/m², about 30 L/min/m² to about 200 L/min/m², about 30 L/min/m² to about 225 L/min/m², about 30 L/min/m² to about 250 L/min/m², about 30 L/min/m² to about 275 L/min/m², about 30 L/min/m² to about 300 L/min/m², about 30 L/min/m² to about 325 L/min/m², about 30 L/min/m² to about 350 L/min/m², about 40 L/min/m² to about 50 L/min/m², about 40 L/min/m² to about 60 L/min/m², about 40 L/min/m² to about 70 L/min/m², about 40 L/min/m² to about 80 L/min/m², about 40 L/min/m² to about 90 L/min/m², about 40 L/min/m² to about 100 L/min/m², about 40 L/min/m² to about 125 L/min/m², about 40 L/min/m² to about 150 L/min/m², about 40 L/min/m² to about 175 L/min/m², about 40 L/min/m² to about 200 L/min/m², about 40 L/min/m² to about 225 L/min/m², about 40 L/min/m² to about 250 L/min/m², about 40 L/min/m² to about 275 L/min/m², about 40 L/min/m² to about 300 L/min/m², about 40 L/min/m² to about 325 L/min/m², about 40 L/min/m² to about 350 L/min/m², about 50 L/min/m² to about 60 L/min/m², about 50 L/min/m² to about 70 L/min/m², about 50 L/min/m² to about 80 L/min/m², about 50 L/min/m² to about 90 L/min/m², about 50 L/min/m² to about 100 L/min/m², about 50 L/min/m² to about 125 L/min/m², about 50 L/min/m² to about 150 L/min/m², about 50 L/min/m² to about 175 L/min/m², about 50 L/min/m² to about 200 L/min/m², about 50 L/min/m² to about 225 L/min/m², about 50 L/min/m² to about 250 L/min/m², about 50 L/min/m² to about 275 L/min/m², about 50 L/min/m² to about 300 L/min/m², about 50 L/min/m² to about 325 L/min/m², about 50 L/min/m² to about 350 L/min/m², about 60 L/min/m² to about 70 L/min/m², about 60 L/min/m² to about 80 L/min/m², about 60 L/min/m² to about 90 L/min/m², about 60 L/min/m² to about 100 L/min/m², about 60 L/min/m² to about 125 L/min/m², about 60 L/min/m² to about 150 L/min/m², about 60 L/min/m² to about 175 L/min/m², about 60 L/min/m² to about 200 L/min/m², about 60 L/min/m² to about 225 L/min/m², about 60 L/min/m² to about 250 L/min/m², about 60 L/min/m² to about 275 L/min/m², about 60 L/min/m² to about 300 L/min/m², about 60 L/min/m² to about 325 L/min/m², about 60 L/min/m² to about 350 L/min/m², about 70 L/min/m² to about 80 L/min/m², about 70 L/min/m² to about 90 L/min/m², about 70 L/min/m² to about 100 L/min/m², about 70 L/min/m² to about 125 L/min/m², about 70 L/min/m² to about 150 L/min/m², about 70 L/min/m² to about 175 L/min/m², about 70 L/min/m² to about 200 L/min/m², about 70 L/min/m² to about 225 L/min/m², about 70 L/min/m² to about 250 L/min/m², about 70 L/min/m² to about 275 L/min/m², about 70 L/min/m² to about 300 L/min/m², about 70 L/min/m² to about 325 L/min/m², about 70 L/min/m² to about 350 L/min/m², about 80 L/min/m² to about 90 L/min/m², about 80 L/min/m² to about 100 L/min/m², about 80 L/min/m² to about 125 L/min/m², about 80 L/min/m² to about 150 L/min/m², about 80 L/min/m² to about 175 L/min/m², about 80 L/min/m² to about 200 L/min/m², about 80 L/min/m² to about 225 L/min/m², about 80 L/min/m² to about 250 L/min/m², about 80 L/min/m² to about 275 L/min/m², about 80 L/min/m² to about 300 L/min/m², about 80 L/min/m² to about 325 L/min/m², about 80 L/min/m² to about 350 L/min/m², about 90 L/min/m² to about 100 L/min/m², about 90 L/min/m² to about 125 L/min/m², about 90 L/min/m² to about 150 L/min/m², about 90 L/min/m² to about 175 L/min/m², about 90 L/min/m² to about 200 L/min/m², about 90 L/min/m² to about 225 L/min/m², about 90 L/min/m² to about 250 L/min/m², about 90 L/min/m² to about 275 L/min/m², about 90 L/min/m² to about 300 L/min/m², about 90 L/min/m² to about 325 L/min/m², about 90 L/min/m² to about 350 L/min/m², about 100 L/min/m² to about 125 L/min/m², about 100 L/min/m² to about 150 L/min/m², about 100 L/min/m² to about 175 L/min/m², about 100 L/min/m² to about 200 L/min/m², about 100 L/min/m² to about 225 L/min/m², about 100 L/min/m² to about 250 L/min/m², about 100 L/min/m² to about 275 L/min/m², about 100

L/min/m² to about 300 L/min/m², about 100 L/min/m² to about 325 L/min/m², about 100 L/min/m² to about 350 L/min/m², about 125 L/min/m² to about 150 L/min/m², about 125 L/min/m² to about 175 L/min/m², about 125 L/min/m² to about 200 L/min/m², about 125 L/min/m² to about 225 L/min/m², about 125 L/min/m² to about 250 L/min/m², about 125 L/min/m² to about 275 L/min/m², about 125 L/min/m² to about 300 L/min/m², about 125 L/min/m² to about 325 L/min/m², about 125 L/min/m² to about 350 L/min/m², about 150 L/min/m² to about 175 L/min/m², about 150 L/min/m² to about 200 L/min/m², about 150 L/min/m² to about 225 L/min/m², about 150 L/min/m² to about 250 L/min/m², about 150 L/min/m² to about 275 L/min/m², about 150 L/min/m² to about 300 L/min/m², about 150 L/min/m² to about 325 L/min/m², about 150 L/min/m² to about 350 L/min/m², about 175 L/min/m² to about 200 L/min/m², about 175 L/min/m² to about 225 L/min/m², about 175 L/min/m² to about 250 L/min/m², about 175 L/min/m² to about 275 L/min/m², about 175 L/min/m² to about 300 L/min/m², about 175 L/min/m² to about 325 L/min/m², about 175 L/min/m² to about 350 L/min/m², about 200 L/min/m² to about 225 L/min/m², about 200 L/min/m² to about 250 L/min/m², about 200 L/min/m² to about 275 L/min/m², about 200 L/min/m² to about 300 L/min/m², about 200 L/min/m² to about 325 L/min/m², about 200 L/min/m² to about 350 L/min/m², about 225 L/min/m² to about 250 L/min/m², about 225 L/min/m² to about 275 L/min/m², about 225 L/min/m² to about 300 L/min/m², about 225 L/min/m² to about 325 L/min/m², about 225 L/min/m² to about 350 L/min/m², about 250 L/min/m² to about 275 L/min/m², about 250 L/min/m² to about 300 L/min/m², about 250 L/min/m² to about 325 L/min/m², about 250 L/min/m² to about 350 L/min/m², about 275 L/min/m² to about 300 L/min/m², about 275 L/min/m² to about 325 L/min/m², about 275 L/min/m² to about 350 L/min/m², about 300 L/min/m² to about 325 L/min/m², about 300 L/min/m² to about 350 L/min/m², or about 325 L/min/m² to about 350 L/min/m².

In one embodiment, an effective amount of a composition disclosed herein, including a dry powdered, liquid, paste or colloidal composition disclosed herein, is applied at a pressure rate of 30 kPa/m² to 1,500 kPa/m². In aspects of this embodiment, an effective amount of a composition disclosed herein is applied at a pressure rate of, e.g., about 50 kPa/m², about 100 kPa/m², about 200 kPa/m², about 300 kPa/m², about 400 kPa/m², about 500 kPa/m², about 600 kPa/m², about 700 kPa/m², about 800 kPa/m², about 900 kPa/m², about 1,000 kPa/m², about 1,100 kPa/m², about 1,200 kPa/m², about 1,300 kPa/m², about 1,400 kPa/m², or about 1,500 kPa/m². In other aspects of this embodiment, an effective amount of a composition disclosed herein is applied at a pressure rate of, e.g., at least 50 kPa/m², at least 100 kPa/m², at least 200 kPa/m², at least 300 kPa/m², at least 400 kPa/m², at least 500 kPa/m², at least 600 kPa/m², at least 700 kPa/m², at least 800 kPa/m², at least 900 kPa/m², at least 1,000 kPa/m², at least 1,100 kPa/m², at least 1,200 kPa/m², at least 1,300 kPa/m², at least 1,400 kPa/m², or at least 1,500 kPa/m². In yet other aspects of this embodiment, an effective amount of a composition disclosed herein is applied at a pressure rate of, e.g., at most 50 kPa/m², at most 100 kPa/m², at most 200 kPa/m², at most 300 kPa/m², at most 400 kPa/m², at most 500 kPa/m², at most 600 kPa/m², at most 700 kPa/m², at most 800 kPa/m², at most 900 kPa/m², at most 1,000 kPa/m², at most 1,100 kPa/m², at most 1,200 kPa/m², at most 1,300 kPa/m², at most 1,400 kPa/m², or at most 1,500 kPa/m².

In still other aspects of this embodiment, an effective amount of a composition disclosed herein is applied at a pressure rate of, e.g., about 50 kPa/m² to about 100 kPa/m², about 50 kPa/m² to about 200 kPa/m², about 50 kPa/m² to about 300 kPa/m², about 50 kPa/m² to about 400 kPa/m², about 50 kPa/m² to about 500 kPa/m², about 50 kPa/m² to about 600 kPa/m², about 50 kPa/m² to about 700 kPa/m², about 50 kPa/m² to about 800 kPa/m², about 50 kPa/m² to about 900 kPa/m², about 50 kPa/m² to about 1,000 kPa/m², about 50 kPa/m² to about 1,100 kPa/m², about 50 kPa/m² to about 1,200 kPa/m², about 50 kPa/m² to about 1,300 kPa/m², about 50 kPa/m² to about 1,400 kPa/m², about 50 kPa/m² to about 1,500 kPa/m², about 100 kPa/m² to about 200 kPa/m², about 100 kPa/m² to about 300 kPa/m², about 100 kPa/m² to about 400 kPa/m², about 100 kPa/m² to about 500 kPa/m², about 100 kPa/m² to about 600 kPa/m², about 100 kPa/m² to about 700 kPa/m², about 100 kPa/m² to about 800 kPa/m², about 100 kPa/m² to about 900 kPa/m², about 100 kPa/m² to about 1,000 kPa/m², about 100 kPa/m² to about 1,100 kPa/m², about 100 kPa/m² to about 1,200 kPa/m², about 100 kPa/m² to about 1,300 kPa/m², about 100 kPa/m² to about 1,400 kPa/m², about 100 kPa/m² to about 1,500 kPa/m², about 200 kPa/m² to about 300 kPa/m², about 200 kPa/m² to about 400 kPa/m², about 200 kPa/m² to about 500 kPa/m², about 200 kPa/m² to about 600 kPa/m², about 200 kPa/m² to about 700 kPa/m², about 200 kPa/m² to about 800 kPa/m², about 200 kPa/m² to about 900 kPa/m², about 200 kPa/m² to about 1,000 kPa/m², about 200 kPa/m² to about 1,100 kPa/m², about 200 kPa/m² to about 1,200 kPa/m², about 200 kPa/m² to about 1,300 kPa/m², about 200 kPa/m² to about 1,400 kPa/m², about 200 kPa/m² to about 1,500 kPa/m², about 300 kPa/m² to about 400 kPa/m², about 300 kPa/m² to about 500 kPa/m², about 300 kPa/m² to about 600 kPa/m², about 300 kPa/m² to about 700 kPa/m², about 300 kPa/m² to about 800 kPa/m², about 300 kPa/m² to about 900 kPa/m², about 300 kPa/m² to about 1,000 kPa/m², about 300 kPa/m² to about 1,100 kPa/m², about 300 kPa/m² to about 1,200 kPa/m², about 300 kPa/m² to about 1,300 kPa/m², about 300 kPa/m² to about 1,400 kPa/m², about 300 kPa/m² to about 1,500 kPa/m², about 400 kPa/m² to about 500 kPa/m², about 400 kPa/m² to about 600 kPa/m², about 400 kPa/m² to about 700 kPa/m², about 400 kPa/m² to about 800 kPa/m², about 400 kPa/m² to about 900 kPa/m², about 400 kPa/m² to about 1,000 kPa/m², about 400 kPa/m² to about 1,100 kPa/m², about 400 kPa/m² to about 1,200 kPa/m², about 400 kPa/m² to about 1,300 kPa/m², about 400 kPa/m² to about 1,400 kPa/m², about 400 kPa/m² to about 1,500 kPa/m², about 500 kPa/m² to about 600 kPa/m², about 500 kPa/m² to about 700 kPa/m², about 500 kPa/m² to about 800 kPa/m², about 500 kPa/m² to about 900 kPa/m², about 500 kPa/m² to about 1,000 kPa/m², about 500 kPa/m² to about 1,100 kPa/m², about 500 kPa/m² to about 1,200 kPa/m², about 500 kPa/m² to about 1,300 kPa/m², about 500 kPa/m² to about 1,400 kPa/m², about 500 kPa/m² to about 1,500 kPa/m², about 600 kPa/m² to about 700 kPa/m², about 600 kPa/m² to about 800 kPa/m², about 600 kPa/m² to about 900 kPa/m², about 600 kPa/m² to about 1,000 kPa/m², about 600 kPa/m² to about 1,100 kPa/m², about 600 kPa/m² to about 1,200 kPa/m², about 600 kPa/m² to about 1,300 kPa/m², about 600 kPa/m² to about 1,400 kPa/m², about 600 kPa/m² to about 1,500 kPa/m², about 700 kPa/m² to about 800 kPa/m², about 700 kPa/m² to about 900 kPa/m², about 700 kPa/m² to about 1,000 kPa/m², about 700 kPa/m² to about 1,100 kPa/m², about 700 kPa/m² to about 1,200 kPa/m², about 700 kPa/m² to about 1,300 kPa/m², about 700 kPa/m² to about 1,400 kPa/m², about 700 kPa/m² to about 1,500 kPa/m², about 800 kPa/m² to about 900 kPa/m², about 800 kPa/m$^2$ to about 1,000 kPa/m$^2$, about 800 kPa/m$^2$ to about 1,100 kPa/m$^2$, about 800 kPa/m$^2$ to about 1,200 kPa/m$^2$, about 800 kPa/m$^2$ to about 1,300 kPa/m$^2$, about 800 kPa/m$^2$ to about 1,400 kPa/m$^2$, about 800 kPa/m$^2$ to about 1,500 kPa/m$^2$, about 900 kPa/m$^2$ to about 1,000 kPa/m$^2$, about 900 kPa/m$^2$ to about 1,100 kPa/m$^2$, about 900 kPa/m$^2$ to about 1,200 kPa/m$^2$, about 900 kPa/m$^2$ to about 1,300 kPa/m$^2$, about 900 kPa/m$^2$ to about 1,400 kPa/m$^2$, about 900 kPa/m$^2$ to about 1,500 kPa/m$^2$, about 1,000 kPa/m$^2$ to about 1,100 kPa/m$^2$, about 1,000 kPa/m$^2$ to about 1,200 kPa/m$^2$, about 1,000 kPa/m$^2$ to about 1,300 kPa/m$^2$, about 1,000 kPa/m$^2$ to about 1,400 kPa/m$^2$, about 1,000 kPa/m$^2$ to about 1,500 kPa/m$^2$, about 1,100 kPa/m$^2$ to about 1,200 kPa/m$^2$, about 1,100 kPa/m$^2$ to about 1,300 kPa/m$^2$, about 1,100 kPa/m$^2$ to about 1,400 kPa/m$^2$, about 1,100 kPa/m$^2$ to about 1,500 kPa/m$^2$, about 1,200 kPa/m$^2$ to about 1,300 kPa/m$^2$, about 1,200 kPa/m$^2$ to about 1,400 kPa/m$^2$, about 1,200 kPa/m$^2$ to about 1,500 kPa/m$^2$, about 1,300 kPa/m$^2$ to about 1,400 kPa/m$^2$, about 1,300 kPa/m$^2$ to about 1,500 kPa/m$^2$, or about 1,400 kPa/m$^2$ to about 1,500 kPa/m$^2$.

A composition disclosed herein, can be applied to an area where control of a fire is desired using an wide variety of fire extinguishing delivery systems. A fire extinguishing delivery system includes low pressure and high-pressure systems that employ an undiluted or diluted form of a liquid, paste or colloidal composition disclosed herein. A fire extinguishing delivery system used to apply a composition disclosed herein will typically be the most suitable system that is best suited for the type of fire desired to be controlled. Exemplary fire extinguishing fire extinguishing are disclosed in, for example U.S. Pat. Nos. 5,762,145, 7,823,650, 7,905,296, 8,042,619, 8,087,488, 8,439,123, 8,453,751, 8,459,369, 8,505,642, 8,646,540, 8,733,461, 9,339,67, 9,802,069, 10,569,116, 10,350,443, and 10,105,562; the content of each of which is hereby incorporated by reference in its entirety.

In some embodiments, a composition disclosed herein may be used as an undiluted or diluted liquid compositions disclosed herein and applied using a portable fire extinguisher, an air-aspirating sprinkler head system, a non-air-aspirating sprinkler head system, a portable, pressure-feed device with a spray nozzle, a bubble generating nozzle or a water fog nozzle, or a large scale fire-fighting equipment, either stand alone or incorporated into a firefighting land vehicle, aircraft or watercraft, and the like. Liquid compositions disclosed herein may be applied directly to a fire or indirectly by applying to an adjacent area and allowing the foam to flow onto the fire. The dilution process may optionally involve any of a fixed or portable in-line educator, an in-line balanced pressure and pump pressure proportioning ski, a bladder tank balanced pressure proportioning system, an around the pump proportioner, or a handline air-aspirating nozzle with fixed educator pickup tube.

In some embodiments, a composition compositions disclosed herein may be used as an undiluted or diluted liquid composition and applied as a foam compositions disclosed herein using foam generating equipment, such as, e.g., an aspirated foam generating device, a non-aspirated foam generating device, a portable, pressure-feed device with a bubble generating nozzle or an air-aspirating foam nozzle, a foam gun, a foam chamber, a foam maker used with a Floating Roof storage tank for Dike/Bund protection system, an air-aspirating sprinkler head system, a non-air-aspirating sprinkler head system, a high back pressure foam making subsurface base injection systems, a large scale fire-fighting equipment, either stand alone or incorporated into a firefighting land vehicle, aircraft or watercraft, and the like as described in the above-referenced "Firefighters Guide to Foam", BS EN 13565 standards, or NFPA Standards, which is hereby incorporated by reference in its entirety. A method for foaming the fire extinguishing compositions is not particularly limited and exemplified by a method utilizing a nozzle that takes in air and generates foam when the fire extinguishing compositions are sprayed. Foam compositions disclosed herein may be applied directly to a fire or indirectly by applying to an adjacent area and allowing the foam to flow onto the fire. The dilution process may optionally involve any of a fixed or portable in-line educator, an in-line balanced pressure and pump pressure proportioning ski, a bladder tank balanced pressure proportioning system, an around the pump proportioner, or a handline air-aspirating nozzle with fixed educator pickup tube. In some embodiments, a foam composition disclosed herein comprises, consists essentially of, or consists of only an undiluted or diluted liquid composition disclosed herein and further foaming agents are not included. IN aspects of these embodiments, a foam composition disclosed herein comprises, consists essentially of, or consists of only an undiluted or diluted liquid composition disclosed herein and does not include fluorosurfactant foaming agents or fluoroprotein forming agents.

Another advantage of a composition disclosed herein when used in a fire suppression system, like a sprinkler head system, is that a composition disclosed herein also dissolve, disperse, or otherwise remove one or more components that disrupt water flow in the pipe and holding tank of the system. The presence of a composition disclosed herein provides adequate disruption of one or more components, including biofilm, blocking one or more pipes, sprinkler heads or other components of a fire suppression system. Without wishing to be limited by its theory, this mechanism of action is tied to the ability of a composition disclosed herein to dissolve or otherwise remove one or more components, including biofilm, blocking the pipeline network. For example, the presence of a composition disclosed herein creates "functionalized" microbubbles that increase oxygen dispersion resulting in higher dissolved oxygen levels and accelerate molecular interactions resulting in catalytic breakdown of one or more components, including biofilm, blocking one or more pipes, sprinkler heads or other components of a fire suppression system.

An area includes any location where fuel fora fire is present and includes, without limitation, a man-made structure or apparatus, or a natural structure or location. Non-limiting examples of a man-made structure include a bridge, a building, such as, e.g., residential, commercial, industrial, or agricultural, and the like. Non-limiting examples of a man-made apparatus include a land vehicle, such as, e.g., a motorcycle, automobile, truck, and the like, a watercraft, such as, e.g., a ship, tanker, passenger ship, boat, or submarine and the like, an aircraft, such as, e.g., an airplane, helicopter, drone, and the like, an appliance, an equipment, a device, and the like. Non-limiting examples of a natural structure or location include an agricultural field, a forest, a grassland, a bushland, or any other environmental area.

Application of a composition disclosed herein, including a dry powdered, liquid, paste or colloidal composition disclosed herein, can be achieved by any process that effectively creates microbubbles. For example, any method that can introduce large concentrations of a gas into a composition during application is suitable because such gas introduction enables the spontaneous formation of microbubbles. Suitable application processes include, without limitation, spraying, fogging, atomizing, vaporizing, scattering, watering, squirting, sprinkling and the like. One preferred method of application is by a manual or mechanical application by irrigation, spraying, fogging, atomizing or vaporizing. Such applications provide formation of finely divided mist with sufficient aeration during the application process to create microbubbles as disclosed herein. Microbubbles exposed to a dispersion of gas in a liquid display colloidal property and are referred to as colloidal gas aphrons (CGA). CGA differ from ordinary gas bubbles in that they contain a distinctive shell layer containing a low concentration of a surfactant.

The microbubbles formed with a composition disclosed herein appear to increase the mass transfer of oxygen in liquids. Without being bound by scientific theory, there are several possible explanations for this difference. First, the surfactants formulated into a composition disclosed herein include nonionic surfactants and/or biosurfactants which significantly alter the properties of bubble behavior. Second, a composition disclosed herein requires a much lower concentration of surfactants for microbubble formation. It has been suggested that surfactant concentrations must approach the critical micelles concentration (CMS) of a surfactant system. In a composition disclosed herein, microbubbles are formed below estimated CMCs for the surfactants used. This suggests that the microbubbles are the result of aggregates of surfactant molecules with a loose molecular packing more favorable to gas mass transfer characteristics. A surface containing fewer surfactant molecules would be more gas permeable than a well-organized micelle containing gas. Regardless of the mechanism, the tendency of a composition disclosed herein to organizes into clusters, aggregates, or gas-filled bubbles provides a platform for reactions to occur by increasing localized concentrations of reactants, lowering the transition of energy required for a catalytic reaction to occur, or some other mechanism which has not yet been described.

In aspects of this embodiment, a microbubbles disclosed herein have a mean diameter of, e.g., about 5 μm, about 10 μm, about 15 μm, about 20 μm, about 25 μm, about 30 μm, about 40 μm, about 50 μm, about 75 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm or about 1000 μm. In other aspects of this embodiment, a microbubbles disclosed herein have a mean diameter of, e.g., at least 5 μm, at least 10 μm, at least 15 μm, at least 20 μm, at least 25 μm, at least 30 μm, at least 40 μm, at least 50 μm, at least 100 μm, at least 150 μm, at least 200 μm, at least 250 μm, at least 300 μm, at least 350 μm, at least 400 μm, at least 450 μm, at least 500 μm, at least 550 μm, at least 600 μm, at least 650 μm, at least 700 μm, at least 750 μm, at least 800 μm, at least 850 μm, at least 900 μm, at least 950 μm or at least 1000 μm. In other aspects of this embodiment, a microbubbles disclosed herein have a mean diameter of, e.g., at most 5 μm, at most 10 μm, at most 15 μm, at most 20 μm, at most 25 μm, at most 30 μm, at most 40 μm, at most 50 μm, at most 100 μm, at most 150 μm, at most 200 μm, at most 250 μm, at most 300 μm, at most 350 μm, at most 400 μm, at most 450 μm, at most 500 μm, at most 550 μm, at most 600 μm, at most 650 μm, at most 700 μm, at most 750 μm, at most 800 μm, at most 850 μm, at most 900 μm, at most 950 μm or at most 1000 μm.

In aspects of this embodiment, a microbubbles disclosed herein have a mean diameter of, e.g., about 5 μm to about 10 μm, about 5 μm to about 15 μm, about 5 μm to about 20 μm, about 5 μm to about 25 μm, about 5 μm to about 30 μm, about 5 μm to about 40 μm, about 5 μm to about 50 μm, about 5 μm to about 75 μm, about 5 μm to about 100 μm, about 10 μm to about 15 μm, about 10 μm to about 20 μm, about 10 μm to about 25 μm, about 10 μm to about 30 μm, about 10 μm to about 40 μm, about 10 μm to about 50 μm, about 10 μm to about 75 μm, about 10 μm to about 100 μm, about 15 μm to about 20 μm, about 15 μm to about 25 μm, about 15 μm to about 30 μm, about 15 μm to about 40 μm, about 15 μm to about 50 μm, about 15 μm to about 75 μm, about 15 μm to about 100 μm, about 20 μm to about 25 μm, about 20 μm to about 30 μm, about 20 μm to about 40 μm, about 20 μm to about 50 μm, about 20 μm to about 75 μm, about 20 μm to about 100 μm, about 25 μm to about 30 μm, about 25 μm to about 40 μm, about 25 μm to about 50 μm, about 25 μm to about 75 μm, about 25 μm to about 100 μm, about 30 μm to about 40 μm, about 30 μm to about 50 μm, about 30 μm to about 75 μm, about 30 μm to about 100 μm, about 40 μm to about 50 μm, about 40 μm to about 75 μm, about 40 μm to about 100 μm, about 50 μm to about 75 μm, about 50 μm to about 100 μm, about 50 μm to about 150 μm, about 50 μm to about 200 μm, about 50 μm to about 250 μm, about 50 μm to about 300 μm, about 50 μm to about 350 μm, about 50 μm to about 400 μm, about 50 μm to about 450 μm, about 50 μm to about 500 μm, about 50 μm to about 550 μm, about 50 μm to about 600 μm, about 50 μm to about 650 μm, about 50 μm to about 700 μm, about 50 μm to about 750 μm, about 50 μm to about 800 μm, about 50 μm to about 850 μm, about 50 μm to about 900 μm, about 50 μm to about 950 μm, about 50 μm to about 1000 μm, about 100 μm to about 150 μm, about 100 μm to about 200 μm, about 100 μm to about 250 μm, about 100 μm to about 300 μm, about 100 μm to about 350 μm, about 100 μm to about 400 μm, about 100 μm to about 450 μm, about 100 μm to about 500 μm, about 100 μm to about 550 μm, about 100 μm to about 60 μm, about 100 μm to about 650 μm, about 100 μm to about 700 μm, about 100 μm to about 750 μm, about 100 μm to about 800 μm, about 100 μm to about 850 μm, about 100 μm to about 900 μm, about 100 μm to about 950 μm, about 100 μm to about 1000 μm, about 150 μm to about 200 μm, about 150 μm to about 250 μm, about 150 μm to about 300 μm, about 150 μm to about 350 μm, about 150 μm to about 400 μm, about 150 μm to about 450 μm, about 150 μm to about 500 μm, about 150 μm to about 550 μm, about 150 μm to about 600 μm, about 150 μm to about 650 μm, about 150 μm to about 700 μm, about 150 μm to about 750 μm, about 150 μm to about 800 μm, about 150 μm to about 850 μm, about 150 μm to about 900 μm, about 150 μm to about 950 μm, about 150 μm to about 1000 μm, about 200 μm to about 250 μm, about 200 μm to about 300 μm, about 200 μm to about 350 μm, about 200 μm to about 400 μm, about 200 μm to about 450 μm, about 200 μm to about 500 μm, about 200 μm to about 550 μm, about 200 μm to about 600 μm, about 200 μm to about 650 μm, about 200 μm to about 700 μm, about 200 μm to about 750 μm, about 200 μm to about 800 μm, about 200 μm to about 850 μm, about 200 μm to about 900 μm, about 200 μm to about 950 μm, about 200 μm to about 1000 μm, about 250 μm to about 300 μm, about 250 μm to about 350 μm, about 250 μm to about 400 μm, about 250 μm to about 450 μm, about 250 μm to about 500 μm, about 250 μm to about 550 μm, about 250 μm to about 600 μm, about 250 μm to about 650 μm, about 250 μm to about 700 μm, about 250 μm to about 750 μm, about 250 μm to about 800 μm, about 250 μm to about 850 μm, about 250 μm to about 900 μm, about 250 μm to about 950 μm, about 250 μm to about 1000 μm, about 300 μm to about 350 μm, about 300 μm to about 400 μm, about 300 μm to about 450 μm, about 300 μm to about 500 μm, about 300 μm to about 550 μm, about 300 μm to about 600 μm, about 300 μm to about 650 μm, about 300 μm to about 700 μm, about 300 μm to about 750 μm, about 300 μm to about 800 μm, about 300 μm to about 850 μm, about 300 μm to about 900 μm, about 300 μm to about 950 μm, about 300 μm to about 1000 μm, about 350 μm to about 400 μm, about 350 μm to about 450 μm, about 350 μm to about 500 μm, about 350 μm to about 550 μm, about 350 μm to about 600 μm, about 350 μm to about 650 μm, about 350 μm to about 700 μm, about 350 μm to about 750 μm, about 350 μm to about 800 μm, about 350 μm to about 850 μm, about 350 μm to about 900 μm, about 350 μm to about 950 μm, about 350 μm to about 1000 μm, about 400 μm to about 450 μm, about 400 μm to about 500 μm, about 400 μm to about 550 μm, about 400 μm to about 600 μm, about 400 μm to about 650 μm, about 400 μm to about 700 μm, about 400 μm to about 750 μm, about 400 μm to about 800 μm, about 400 μm to about 850 μm, about 400 μm to about 900 μm, about 400 μm to about 950 μm, about 400 μm to about 1000 μm, about 450 μm to about 500 μm, about 450 μm to about 550 μm, about 450 μm to about 600 μm, about 450 μm to about 650 μm, about 450 μm to about 700 μm, about 450 μm to about 750 μm, about 450 μm to about 800 μm, about 450 μm to about 850 μm, about 450 μm to about 900 μm, about 450 μm to about 950 μm, about 450 μm to about 1000 μm, about 500 μm to about 550 μm, about 500 μm to about 600 μm, about 500 μm to about 650 μm, about 500 μm to about 700 μm, about 500 μm to about 750 μm, about 500 μm to about 800 μm, about 500 μm to about 850 μm, about 500 μm to about 900 μm, about 500 μm to about 950 μm, about 500 μm to about 1000 μm, about 550 μm to about 600 μm, about 550 μm to about 650 μm, about 550 μm to about 700 μm, about 550 μm to about 750 μm, about 550 μm to about 800 μm, about 550 μm to about 850 μm, about 550 μm to about 900 μm, about 550 μm to about 950 μm, about 550 μm to about 1000 μm, about 600 μm to about 650 μm, about 600 μm to about 700 μm, about 600 μm to about 750 μm, about 600 μm to about 800 μm, about 600 μm to about 850 μm, about 600 μm to about 900 μm, about 600 μm to about 950 μm, about 600 μm to about 1000 μm, about 650 μm to about 700 μm, about 650 μm to about 750 μm, about 650 μm to about 800 μm, about 650 μm to about 850 μm, about 650 μm to about 900 μm, about 650 μm to about 950 μm, about 650 μm to about 1000 μm, about 700 μm to about 750 μm, about 700 μm to about 800 μm, about 700 μm to about 850 μm, about 700 μm to about 900 μm, about 700 μm to about 950 μm, about 700 μm to about 1000 μm, about 750 μm to about 800 μm, about 750 μm to about 850 μm, about 750 μm to about 900 μm, about 750 μm to about 950 μm, about 750 μm to about 1000 μm, about 800 μm to about 850 μm, about 800 μm to about 900 μm, about 800 μm to about 950 μm, about 800 μm to about 1000 μm, about 850 μm to about 900 μm, about 850 μm to about 950 μm, about 850 μm to about 1000 μm, about 900 μm to about 950 μm, about 900 μm to about 1000 μm or about 950 μm to about 1000 μm.

Aspects of the present specification can also be described by the following embodiments:

1. A method for controlling a fire, the method comprising: applying an effective amount of a composition to a fire, wherein the composition comprises a treated, fermented microbial supernatant including bio-nutrients, minerals, and amino acids and one or more nonionic surfactants.
2. The method according to embodiment 1, wherein the treated, fermented microbial supernatant is from a fermented yeast supernatant, a fermented bacterial supernatant, a fermented mold supernatant, or any combination thereof.
3. The method according to embodiment 2, wherein the fermented yeast supernatant is produced from a culture containing yeast belonging to the genus *Brettanomyces, Candida, Cyberlindnera, Cystofilobasidium, Debaryomyces, Dekkera, Fusarium, Geotrichum, Issatchenkia, Kazachstania, Kioeckera, Kluyveromyces, Lecanicillium, Mucor, Neurospora, Penicillium, Pichia, Rhizopus, Rhodosporidium, Rhodotorula, Saccharomyces, Schizosaccharomyces, Thrichosporon, Torulaspora, Torulopsis, Verticillium, Yarrowia, Zygosaccharomyces*, or *Zygotorulaspora*.
4. The method according to any one of embodiments 1-3, wherein the treated, fermented microbial supernatant lacks any active enzymes, activatable pro-enzymes, or any enzymatic activity.
5. The method according to any one of embodiments 1-4, wherein the one or more nonionic surfactants include one or more polyether nonionic surfactants, one or more polyhydroxyl nonionic surfactants, and/or one or more nonionic biosurfactants.
6. The method according to embodiment 5, wherein the one or more polyhydroxyl nonionic surfactant comprises a sucrose ester, an ethoxylated sucrose ester, a sorbital ester, an ethoxylated sorbital ester, an alkyl glucoside, an ethoxylated alkyl glucoside, a polyglycerol ester, or an ethoxylated polyglycerol ester.
7. The method according to any one of embodiments 1-4, wherein the one or more nonionic surfactants include one or more alcohol ethoxylate nonionic surfactants, one or more alkylphenol ethoxylate nonionic surfactant, alkene amide nonionic surfactant, or a combination thereof.
8. The method according to embodiment 7, wherein the one or more alcohol ethoxylate nonionic surfactants includes one or more linear secondary alcohol ethoxylates, one or more fatty alcohol ethoxylates, or a combination thereof.
9. The method according to embodiment 8, wherein the one or more fatty alcohol ethoxylates include an ethoxylated tridecyl alcohol, an ethoxylated dodecyl alcohol, or a combination thereof.
10. The method according to embodiment 7, wherein the one or more alkylphenol ethoxylate nonionic surfactant includes a nonylphenol ethoxylates, an octylphenol ethoxylates, or a combination thereof.
11. The method according to embodiment 5, wherein the one or more nonionic biosurfactant comprises one or more nonionic saponins.
12. The method according to embodiment 10, wherein the one or more saponins include a triterpenoid saponin, a steroidal saponin, or a combination thereof.
13. The method according to embodiment 11, wherein the triterpenoid saponin comprises a tetracyclic triterpenoid saponin, a pentacyclic triterpenoid saponin, or a combination thereof.
14. The method according to embodiment 12, wherein the tetracyclic triterpenoid saponin includes a cucurbitane, a cycloartane, a cycloartenol, a dammarane, a euphane, a lanostane, or a tirucallane.
15. The method according to embodiment 12, wherein the pentacyclic triterpenoid saponin includes an enoxolone, a hederagenin, a hopane, a lupane, a maslinic acid, an oleanane, an ursane, or a taraxasterane.
16. The method according to embodiment 11, wherein the steroidal saponin comprises a diosgenin, an eleutheroside, a ginsenoside, a sarsasapogenin, a yamogenin, or any combination thereof.

17. The method according to any one of embodiments 1-15, wherein the composition further comprises one or more anionic surfactants.
18. The method according to embodiment 17, wherein the one or more anionic surfactants include an alkane sulfonate anionic surfactant.
19. The method according to any one of embodiments 1-18, wherein the composition is formulated as a liquid composition, a dry powdered composition, a paste composition or a colloidal composition.
20. The method according to embodiment 19, wherein the colloidal composition is a form composition.
21. The method according to any one of embodiments 1-18, wherein the composition is a liquid composition comprising 15% to 50% by weight of a treated, fermented microbial supernatant and 3% to 15% by weight of one or more nonionic surfactants.
22. The method according to any one of embodiments 1-18, wherein the composition is a dry powdered composition comprising 6% to 15% by weight of a dried treated, fermented microbial supernatant, 6% to 20% by weight of a first dried nonionic biosurfactant, and 87.5% to 87.5% by weight of a second dried nonionic biosurfactant.
23. The method according to any one of embodiments 1-18, wherein the composition is a foam composition comprising 15% to 50% by weight of a treated, fermented microbial supernatant, 3% to 15% by weight of one or more nonionic surfactants.
24. The method according to embodiment 23, wherein the foam composition further comprises 1% to 6% by weight of one or more foaming agents, 2% to 10% by weight of one or more stabilizing agents, or both.
25. The method according to any one of embodiments 1-24, wherein the composition further comprises 1% to 3% by weight of one or more preservatives.
26. The method according to any one of embodiments 1-25, wherein the fire uses combustible solid substances as a fuel source, uses combustible liquid, liquefiable substances or gases as a fuel source, uses combustible metals and metal alloys as a fuel source, or uses combustible cooking liquids as a fuel source.
27. The method according to any one of embodiments 1-26, wherein the fire involve electrical components and/or energized equipment.
28. The method according to any one of embodiments 1-26, wherein the composition is applied to one or more areas where control of a fire is desired.
29. The method according to embodiment 28, wherein the one or more areas is a man-made structure or apparatus, or a natural structure or location.
30. The method according to embodiment 29, wherein the man-made structure include a bridge or a building.
31. The method according to embodiment 29, wherein the man-made apparatus include a land vehicle, a watercraft, an aircraft, an appliance, an equipment, or a device.
32. The method according to embodiment 29, wherein the natural structure or location include an agricultural field, a forest, a grassland, a bushland, or any other environmental area.
33. A liquid composition for use in controlling a fire, the liquid composition comprising 15% to 50% by weight of a treated, fermented microbial supernatant and 3% to 15% by weight of one or more nonionic surfactants.
34. A dry powdered composition for use in controlling a fire, the dry powdered composition comprising 6% to 15% by weight of a dried treated, fermented microbial supernatant, 6% to 20% by weight of a first dried nonionic biosurfactant, and 67.5% to 87.5% by weight of a second dried nonionic biosurfactant.
35. A foam composition for use in controlling a fire, the foam composition comprising 15% to 50% by weight of a treated, fermented microbial supernatant. 3% to 15% by weight of one or more nonionic surfactants, and optionally 1% to 6% by weight of one or more foaming agents, and optionally 1% to 10% by weight of one or more stabilizing agents.
36. A liquid composition for use in controlling a fire, the liquid composition comprising 0.25% to 50% by weight of a treated, fermented microbial supernatant and 10% to 20% by weight of one or more nonionic surfactants, 2% to 8% by weight of one or more anionic surfactants, and 1% to 10% propylene glycol.
37. A foam composition for use in controlling a fire, the foam composition comprising 0.25% to 50% by weight of a treated, fermented microbial supernatant and 10% to 20% by weight of one or more nonionic surfactants, 2% to 8% by weight of one or more anionic surfactants, and 1% to 10% propylene glycol.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the fire extinguishing compositions, or methods or uses disclosed herein.

Example 1

Preparation of Treated Fermented Yeast Supernatant 1

To prepare a treated fermented yeast supernatant, a fermentation reaction is set up in which about 1,000 L of warm water having a temperature of between about 29° C. to about 38° C. was placed in a large, jacketed mixing kettle. To the water was added about 84.9 kg black untreated cane molasses, about 25.2 kg raw cane sugar and about 1.2 kg magnesium sulfate. The mixture was thoroughly blended, after which about 11.4 kg diastatic malt and about 1.2 kg baker's yeast were added and agitated slightly. The mixture is incubated at about 26° C. to about 42° C. for about 3 days, after which the effervescent reaction had subsided, indicating essentially complete fermentation. At the end of the fermentation the yeast fermentation composition is centrifuged to remove the "sludge" formed during the fermentation. The resulting fermentation supernatant (about 98.59%, by weight) was collected and sterilized by autoclaving. The treated fermented yeast supernatant can then be stored in liquid form for subsequent use. Alternatively, the treated fermented yeast supernatant can be spray dried by methods known in the art to produce a dry powder. The dry powder form can also be stored for subsequent use.

Example 2

Preparation of Treated Fermented Yeast Supernatant 2

To prepare a treated fermented yeast supernatant, a fermentation reaction is set up in which about 1,000 L of warm water having a temperature of between about 29° C. to about 38° C. was placed in a large, jacketed mixing kettle. To the water was added about 42.5 kg black untreated cane molasses, about 12.6 kg raw cane sugar and about 1.2 kg magnesium sulfate. The mixture was thoroughly blended, after which about 10.3 kg diastatic malt and about 1.2 kg bakers yeast were added and agitated slightly. The mixture is incubated at about 26° C. to about 42° C. for about 3 days, after which the effervescent reaction had subsided, indicating essentially complete fermentation. At the end of the fermentation the yeast fermentation culture is centrifuged to remove the "sludge" formed during the fermentation. The resulting fermentation yeast supernatant (about 98.59%, by weight) was collected and treated by autoclaving. The treated fermented yeast supernatant can then be stored in liquid form for subsequent use. Alternatively, the treated fermented yeast supernatant can be spray dried by methods known in the art to produce a dry powder. The dry powder form can also be stored for subsequent use.

Example 3

Preparation of Treated Fermented Yeast Supernatant 3

To prepare a treated fermented yeast supernatant, a fermentation reaction is set up in which about 1,000 L of warm water having a temperature of between about 29° C. to about 38° C. was placed in a large, jacketed mixing kettle. To the water was added about 21.3 kg black untreated cane molasses, about 6.3 kg raw cane sugar and about 1.2 kg magnesium sulfate. The mixture was thoroughly blended, after which about 9.3 kg diastatic malt and about 1.2 kg bakers yeast were added and agitated slightly. The mixture is incubated at about 26° C. to about 42° C. for about 3 days, after which the effervescent reaction had subsided, indicating essentially complete fermentation. At the end of the fermentation the yeast fermentation culture is centrifuged to remove the "sludge" formed during the fermentation. The resulting fermentation supernatant (about 98.59%, by weight) was collected and treated by autoclaving. The treated fermented yeast supernatant can then be stored in liquid form for subsequent use. Alternatively, the treated fermented yeast supernatant can be spray dried by methods known in the art to produce a dry powder. The dry powder form can also be stored for subsequent use.

Example 4

Preparation of a Liquid Composition

This example shows exemplary formulations of liquid compositions disclosed herein.

To manufacture an exemplary batch size of 4,500 L of an liquid composition disclosed herein, 1,000 L of hot sterile water (about 60° C. to about 65° C.) was added to 675 L to 2,250 L of treated fermented microbial supernatant (15% to 50% final concentration) in a large, jacketed mixing kettle (see Tables 1-5). To this mixture was added 135 kg to 675 kg of non-ionic surfactants (3% to 15% final concentration) (see Tables 1-5). This mixture was thoroughly blended to effect solution. Additional water was then added to bring a final volume of the mixture to about 4,500 L and stirred until complete mixing was obtained. The pH of the resulting liquid composition was adjusted using any suitable acid, such as, e.g., phosphoric acid. The pH adjusted liquid composition was then filter sterilized to remove any microbial contamination and packaged for distribution. Liquid compositions produced according to this process were found to be nonirritating to skin tissue, nontoxic and could be stored in a cool location over periods of months without any discernible loss in effectiveness or deterioration.

As a specific example of the above, formulation LF3 was prepared by adding 1,000 L of hot sterile water (about 60° C. to about 65° C.) was added to 1,000 L of treated fermented microbial supernatant (22% final concentration) in a large, jacketed mixing kettle. To this mixture was added 168.8 kg of a first linear secondary alcohol ethoxylate (TERGITOL™ 15-S-5, a polyethylene glycol trimethylnonyl ether) (3.75% final concentration) and 168.8 kg of a second linear secondary alcohol ethoxylate (TERGITOL™ 15-S-7, a polyethylene glycol trimethylnonyl ether) (3.75% final concentration) to bring the total nonionic surfactant amount to 337.6 kg (7.5% final concentration). This mixture was thoroughly blended to effect solution. Additional water was then added to bring a final volume of the mixture to about 4,500 L and stirred until complete mixing was obtained. The pH of the resulting liquid composition was adjusted to pH 7.0 using phosphoric acid. The pH adjusted liquid composition was then filter sterilized to remove any microbial contamination and packaged for distribution. Liquid compositions of formulation LF3 produced according to this process were found to be nonirritating to skin tissue, nontoxic and could be stored in a cool location over periods of months without any discernible loss in effectiveness or deterioration.

TABLE 1

Liquid Composition Formulations

| Component | LF1 | LF2 | LF3 | LF4 | LF5 | LF6 | LF7 |
| --- | --- | --- | --- | --- | --- | --- | --- |
| Treated, Fermented Supernatant | 675 L-2,250 L | 675 L-2,250 L | 675 L-2,250 L | 675 L-2,250 L | 675 L-2,250 L | 675 L-2,250 L | 675 L-2,250 L |
| Water | 1,000 L | 1,000 L | 1,000 L | 1,000 L | 1,000 L | 1,000 L | 1,000 L |
| Alcohol ethoxylate nonionic surfactant[1] | 67.5 kg | 101.3 kg | 135 kg | 168.8 kg | 225 kg | 281.2 kg | 337.5 kg |
| Alcohol ethoxylate nonionic surfactant[2] | 67.5 kg | 101.3 kg | 135 kg | 168.8 kg | 225 kg | 281.2 kg | 337.5 kg |
| Water | q.s. | q.s. | q.s. | q.s. | q.s. | q.s. | q.s. |
| pH | 6.5-8.0 | 6.5-8.0 | 6.5-8.0 | 6.5-8.0 | 6.5-8.0 | 6.5-8.0 | 6.5-8.0 |

[1] Linear secondary alcohol ethoxylate (TERGITOL ™ 15-S-5, a polyethylene glycol trimethylnonyl ether).
[2] Linear secondary alcohol ethoxylate (TERGITOL ™ 15-S-7, a polyethylene glycol trimethylnonyl ether).

TABLE 2

Liquid Composition Formulations

| Component | LF8 | LF9 | LF10 | LF11 | LF12 | LF13 | LF14 |
|---|---|---|---|---|---|---|---|
| Treated, Fermented Supernatant | 675 L-2,250 L | 675 L-2,250 L | 675 L-2,250 L | 675 L-2,250 L | 675 L-2,250 L | 675 L-2,250 L | 675 L-2,250 L |
| Water | 1,000 L | 1,000 L | 1,000 L | 1,000 L | 1,000 L | 1,000 L | 1,000 L |
| Alcohol ethoxylate nonionic surfactant[3] | 135 kg | 225 kg | 315 kg | 405 kg | 495 kg | 585 kg | 675 kg |
| Water | q.s. | q.s. | q.s. | q.s. | q.s. | q.s. | q.s. |
| pH | 6.5-8.0 | 6.5-8.0 | 6.5-8.0 | 6.5-8.0 | 6.5-8.0 | 6.5-8.0 | 6.5-8.0 |

[3] Fatty alcohol ethoxylate (ethoxylated dodecyl alcohol).

TABLE 3

Liquid Composition Formulations

| Component | LF15 | LF16 | LF17 | LF18 | LF19 | LF20 | LF21 |
|---|---|---|---|---|---|---|---|
| Treated, Fermented Supernatant | 675 L-2,250 L | 675 L-2,250 L | 675 L-2,250 L | 675 L-2,250 L | 675 L-2,250 L | 675 L-2,250 L | 675 L-2,250 L |
| Water | 1,000 L | 1,000 L | 1,000 L | 1,000 L | 1,000 L | 1,000 L | 1,000 L |
| Alcohol ethoxylate nonionic surfactant[4] | 135 kg | 225 kg | 315 kg | 405 kg | 495 kg | 585 kg | 675 kg |
| Water | q.s. | q.s. | q.s. | q.s. | q.s. | q.s. | q.s. |
| pH | 6.5-8.0 | 6.5-8.0 | 6.5-8.0 | 6.5-8.0 | 6.5-8.0 | 6.5-8.0 | 6.5-8.0 |

[4] Fatty alcohol ethoxylate (ethoxylated tridecyl alcohol).

TABLE 4

Liquid Composition Formulations

| Component | LF22 | LF23 | LF24 | LF25 | LF26 | LF27 | LF28 |
|---|---|---|---|---|---|---|---|
| Treated, Fermented Supernatant | 675 L-2,250 L | 675 L-2,250 L | 675 L-2,250 L | 675 L-2,250 L | 675 L-2,250 L | 675 L-2,250 L | 675 L-2,250 L |
| Water | 1,000 L | 1,000 L | 1,000 L | 1,000 L | 1,000 L | 1,000 L | 1,000 L |
| Alkylphenol ethoxylate nonionic surfactant[5] | 135 kg | 225 kg | 315 kg | 405 kg | 495 kg | 585 kg | 675 kg |
| Water | q.s. | q.s. | q.s. | q.s. | q.s. | q.s. | q.s. |
| pH | 6.5-8.0 | 6.5-8.0 | 6.5-8.0 | 6.5-8.0 | 6.5-8.0 | 6.5-8.0 | 6.5-8.0 |

[5] Nonylphenol ethoxylate.

TABLE 5

Liquid Composition Formulations

| Component | LF29 | LF30 | LF31 | LF32 | LF33 | LF34 | LF35 |
|---|---|---|---|---|---|---|---|
| Treated, Fermented Supernatant | 675 L-2,250 L | 675 L-2,250 L | 675 L-2,250 L | 675 L-2,250 L | 675 L-2,250 L | 675 L-2,250 L | 675 L-2,250 L |
| Water | 1,000 L | 1,000 L | 1,000 L | 1,000 L | 1,000 L | 1,000 L | 1,000 L |
| Alkylphenol ethoxylate nonionic surfactant[6] | 135 kg | 225 kg | 315 kg | 405 kg | 495 kg | 585 kg | 675 kg |
| Water | q.s. | q.s. | q.s. | q.s. | q.s. | q.s. | q.s. |
| pH | 6.5-8.0 | 6.5-8.0 | 6.5-8.0 | 6.5-8.0 | 6.5-8.0 | 6.5-8.0 | 6.5-8.0 |

[6] Octylphenol ethoxylate.

Optionally, 2% to 6% final concentration of an anionic surfactant can be incorporated into a liquid composition of Tables 1-5 prior to adjusting the volume to 4,500 L with additional water. For example, DOWFAX™ 2A1 or an anionic biosurfactant such as, e.g., STEPONOL® AM 30-KE, an ammonium lauryl sulfate, STEPONOL® EHS, a sodium 2-ethyl hexyl sulfate, or a combination thereof can be added to the liquid composition.

Optionally, 0.5% to 3% final concentration of one or more preservatives can be incorporated into a liquid composition of Tables 1-5 prior to adjusting the volume to 4,500 L with additional water. For example, about 1% by weight sodium benzoate, about 0.01% by weight imidazolidinyl urea, about 0.15% by weight diazolidinyl urea, about 0.25% by weight calcium chloride, or about 0.5% sodium hydroxymethylglycinate (Nuosept 44). In this case, the preservatives are added to the liquid mixture and the temperature of the mixture is then slowly raised to about 40° C. for about one hour with continuous agitation to ensure that all the components of the mixture are dissolved. The mixture is then cooled to from about 20° C. to about 25° C. and additional water is then added to bring the final volume of the liquid composition to about 4,500 L and stirred until complete mixing had been obtained. The pH of the resulting liquid composition was adjusted using any suitable acid, such as, e.g., phosphoric acid. The pH adjusted liquid composition was then filter sterilized to remove any microbial contamination and packaged for distribution. Liquid compositions produced according to this process were found to be nonirritating to skin tissue, nontoxic and could be stored in a cool location over periods of months without any discernible loss in effectiveness or deterioration.

To manufacture an exemplary batch size of 3,785 L of an liquid composition disclosed herein, 13.25 kg to 113.6 kg of dry powder fermented microbial supernatant (0.35% to 3.0% final concentration) was added with agitation to 1,000 L of hot sterile water (about 60° C. to about 65° C.) in a large, jacketed mixing kettle (see Table 6). To this mixture was added 113.6 kg to 454.2 kg of propylene glycol (3.0% to 12.0% final concentration) which was blended until uniform. In successive order, 113.6 kg to 454.2 kg of a secondary alcohol ethoxylate nonionic surfactant, TERGITOL™ 15-S-9, a polyethylene glycol trimethylnonyl ether, (3.0% to 12.0% final concentration) was added and blended until uniform, 56.8 kg to 283.9 kg of a secondary alcohol ethoxylate nonionic surfactant, TERGITOL™ 15-S-7, a polyethylene glycol trimethylnonyl ether, (1.5% to 7.5% final concentration) was added and blended until uniform, 94.6 kg to 378.5 kg of an alkane sulfonate anionic surfactant, BIO-TERGE® PAS-8S, a sodium caprylyl sulfonate, (2.5% to 10.0% final concentration) was added and blended until uniform, and 18.9 kg to 170.3 kg of an alkene amide nonionic surfactant, STEPOSOL® MET-10U, a N,N-dimethyl 9-decanamide, (0.5% to 4.5% final concentration) was added and blended until uniform. The mixture is then cooled to from about 20° C. to about 25° C. and additional water is then added to bring the final volume of the liquid composition to about 3,785 L and stirred until complete mixing had been obtained. The pH of the resulting liquid composition was adjusted using any suitable acid, such as, e.g., phosphoric acid. The pH adjusted liquid composition was then filter sterilized to remove any microbial contamination and packaged for distribution. Liquid compositions produced according to this process were found to be nonirritating to skin tissue, nontoxic and could be stored in a cool location over periods of months without any discernible loss in effectiveness or deterioration.

Optionally, 0.5% to 3% final concentration of one or more preservatives can be incorporated into a liquid composition of Table 6 prior to adjusting the volume to 3,785 L with additional water. For example, 18.9 kg of sodium hydroxymethylglycinate (Nuosept 44)(0.5% final concentration) can be added to the liquid mixture and the temperature of the mixture is then slowly raised to about 40° C. for about one hour with continuous agitation to ensure that all the components of the mixture are dissolved. The mixture is then cooled to from about 20° C. to about 25° C. and additional water is then added to bring the final volume of the liquid composition to about 3,785 L and stirred until complete mixing had been obtained. The pH of the resulting liquid composition was adjusted using any suitable acid, such as, e.g., phosphoric acid. The pH adjusted liquid composition was then filter sterilized to remove any microbial contamination and packaged for distribution. Liquid compositions produced according to this process were found to be nonirritating to skin tissue, nontoxic and could be stored in a cool location over periods of months without any discernible loss in effectiveness or deterioration.

TABLE 6

Liquid Composition Formulations

| Component | LF36 | LF37 | LF38 | LF39 | LF40 | LF41 | LF42 |
| --- | --- | --- | --- | --- | --- | --- | --- |
| Dry Powder Fermented Supernatant[7] | 0.35%-2.0% | 0.35% | 0.77% | 2.0% | 0.70% | 1.5% | 3.0% |
| Alcohol ethoxylate nonionic surfactant[8] | 3.0%-9.0% | 3.0% | 6.0% | 9.0% | 6.0% | 9.0% | 12.0% |
| Alcohol ethoxylate nonionic surfactant[9] | 1.5%-6.0% | 1.5% | 3.0% | 6.0% | 3.0% | 6.0% | 7.5% |
| Alkene amide nonionic surfactant[10] | 0.5%-4.5% | 0.5% | 2.0% | 4.5% | 1.0% | 2.0% | 3.0% |
| Alkane sulfonate anionic surfactant[11] | 2.5%-8.0% | 2.5% | 4.5% | 8.0% | 5.0% | 7.5% | 10.0% |

TABLE 6-continued

| Liquid Composition Formulations | | | | | | | |
|---|---|---|---|---|---|---|---|
| Component | LF36 | LF37 | LF38 | LF39 | LF40 | LF41 | LF42 |
| Propylene glycol | 3.0%-9.0% | 3.0% | 6.0% | 9.0% | 6.0% | 9.0% | 12.0% |
| Water[12] | q.s. | q.s. | q.s. | q.s. | q.s. | q.s. | q.s. |
| pH | 6.5-8.0 | 6.5-8.0 | 6.5-8.0 | 6.5-8.0 | 6.5-8.0 | 6.5-8.0 | 6.5-8.0 |

[7]TASTONE 154.
[8]Linear secondary alcohol ethoxylate (TERGITOL™ 15-S-9, a polyethylene glycol trimethylnonyl ether).
[9]Linear secondary alcohol ethoxylate (TERGITOL™ 15-S-7, a polyethylene glycol trimethylnonyl ether).
[10]Alkene di-substituted amide (STEPOSOL® MET-10U).
[11]Sodium caprylyl sulfonate (BIO-TERGE® PAS-8S).
[12]Optionally 0.5% of a preservative can be added.

The formulations of Tables 1-6 are manufactured with the intent to be sold as ready to use, although such ready-to-use products are typically diluted further still when used in a method of use disclosed herein. A concentrate formulation can also be produced. In this case, a liquid composition is manufactured by adding 2,250 L to 4,365 L of treated fermented microbial supernatant (50% to 97% final concentration) in a large jacketed mixing kettle and the volume of water adjusted accordingly. When producing a liquid composition concentrate, the treated fermented microbial supernatant may require heating to about 40° C. to about 65° C. before the nonionic surfactants are added to facilitate dissolvement and proper mixing of the surfactants.

Example 5

Preparation of Dry Powdered Composition

This example shows exemplary formulations of dry powdered compositions disclosed herein.

To manufacture an exemplary batch size of 1000 kg of a dry powdered composition, a powder blender such as a rotor stator or rotary drum mixer is pre-treated by spraying internal surfaces with a 1% bleach solution, incubating for 10 minutes and then wiping surfaces dry. Next, 60 kg to 200 kg of a dried biosurfactant comprising saponins extracted from *Quillaja saponaria* (final concentration 6% to 20%) 60 kg to 150 kg of a dried treated fermented microbial supernatant (final concentration 6% to 15%), and 5 kg to 15 kg of Citric Acid (final concentration 0.5% to 1.5%) were added to the powder blender (see Tables 7-15) and the components blended to achieve a uniform color and appearance of the mixture. To this mixture was added 675 kg to 875 kg of a dried biosurfactant comprising saponins extracted from *Yucca schidigera* (final concentration 67.5% to 87.5%)(see Tables 7-15), and blending continued until a uniform color and appearance of the mixture was achieved. Dry powdered compositions produced according to this process were found to be nonirritating to skin tissue, nontoxic and could be stored in a cool location over periods of months without any discernible loss in effectiveness or deterioration.

As a specific example of the above, formulation PF3 was prepared by adding 90.0 kg of *Quillaja* Dry 100 (a dried biosurfactant comprising saponins extracted from *Quillaja saponaria*) (final concentration 9%), 92.0 kg of TASTONE® 154 (a dried treated fermented microbial supernatant) (final concentration 9.2%), and 10.0 kg of Citric Acid (final concentration 1%) were added to the powder bender and the components blended to achieve a uniform color and appearance of the mixture. To this mixture was added 808.0 kg of *Yucca* SD Powder (a dried biosurfactant comprising saponins extracted from *Yucca schidigera*) (final concentration 80.8%), and blending continued until a uniform color and appearance of the mixture was achieved. Dry powdered compositions of formulation PF3 produced according to this process were found to be nonirritating to skin tissue, nontoxic and could be stored in a cool location over periods of months without any discernible loss in effectiveness or deterioration.

TABLE 7

| Dry Powdered Composition Formulations | | | | | | |
|---|---|---|---|---|---|---|
| Component | PF1 | PF2 | PF3 | PF4 | PF5 | PF6 |
| Dried Fermented Supernatant[1] | 6-9% | 7-10% | 8-11% | 9-12% | 10-13% | 11-14% |
| Dried Biosurfactant[2] | 6-9% | 7-10% | 8-11% | 9-12% | 10-13% | 11-14% |
| Dried Biosurfactant[3] | 80.5-87.5% | 78.5-85.5% | 76.5-83.5% | 74.5-81.5% | 72.5-79.5% | 70.5-77.5% |
| Dried Citric Acid | 0.5-1.5% | 0.5-1.5% | 0.5-1.5% | 0.5-1.5% | 0.5-1.5% | 0.5-1.5% |

[1]a dried yeast supernatant (TASTONE® 154).
[2]a dried biosurfactant comprising saponins extracted from *Quillaja saponaria* (Quillaja Dry 100).
[3]a dried biosurfactant comprising saponins extracted from *Yucca schidigera* (Yucca SD Powder).

TABLE 8

Dry Powdered Composition Formulations

| Component | PF7 | PF8 | PF9 | PF10 | PF11 | PF12 |
|---|---|---|---|---|---|---|
| Dried Fermented Supernatant[1] | 6-9% | 6-9% | 6-9% | 6-9% | 6-9% | 6-9% |
| Dried Biosurfactant[2] | 7-10% | 8-11% | 9-12% | 10-13% | 11-14% | 12-15% |
| Dried Biosurfactant[3] | 79.5-86.5% | 78.5-85.5% | 77.5-84.5% | 76.5-83.5% | 75.5-82.5% | 74.5-81.5% |
| Dried Citric Acid | 0.5-1.5% | 0.5-1.5% | 0.5-1.5% | 0.5-1.5% | 0.5-1.5% | 0.5-1.5% |

[1] a dried yeast supernatant (TASTONE ® 154).
[2] a dried biosurfactant comprising saponins extracted from *Quillaja saponaria* (Quillaja Dry 100).
[3] a dried biosurfactant comprising saponins extracted from *Yucca schidigera* (Yucca SD Powder).

TABLE 9

Dry Powdered Composition Formulations

| Component | PF13 | PF14 | PF15 | PF16 | PF17 | PF18 |
|---|---|---|---|---|---|---|
| Dried Fermented Supernatant[1] | 7-10% | 7-10% | 7-10% | 7-10% | 7-10% | 7-10% |
| Dried Biosurfactant[2] | 6-9% | 8-11% | 9-12% | 10-13% | 11-14% | 12-15% |
| Dried Biosurfactant[3] | 79.5-86.5% | 77.5-84.5% | 76.5-83.5% | 75.5-82.5% | 74.5-81.5% | 73.5-80.5% |
| Dried Citric Acid | 0.5-1.5% | 0.5-1.5% | 0.5-1.5% | 0.5-1.5% | 0.5-1.5% | 0.5-1.5% |

[1] a dried yeast supernatant (TASTONE ® 154).
[2] a dried biosurfactant comprising saponins extracted from *Quillaja saponaria* (Quillaja Dry 100).
[3] a dried biosurfactant comprising saponins extracted from *Yucca schidigera* (Yucca SD Powder).

TABLE 10

Dry Powdered Composition Formulations

| Component | PF19 | PF20 | PF21 | PF22 | PF23 | PF24 |
|---|---|---|---|---|---|---|
| Dried Fermented Supernatant[1] | 8-11% | 8-11% | 8-11% | 8-11% | 8-11% | 8-11% |
| Dried Biosurfactant[2] | 6-9% | 7-10% | 9-12% | 10-13% | 11-14% | 12-15% |
| Dried Biosurfactant[3] | 78.5-85.5% | 77.5-84.5% | 75.5-82.5% | 74.5-81.5% | 73.5-80.5% | 72.5-79.5% |
| Dried Citric Acid | 0.5-1.5% | 0.5-1.5% | 0.5-1.5% | 0.5-1.5% | 0.5-1.5% | 0.5-1.5% |

[1] a dried yeast supernatant (TASTONE ® 154).
[2] a dried biosurfactant comprising saponins extracted from *Quillaja saponaria* (Quillaja Dry 100).
[3] a dried biosurfactant comprising saponins extracted from *Yucca schidigera* (Yucca SD Powder).

TABLE 11

Dry Powdered Composition Formulations

| Component | PF25 | PF26 | PF27 | PF28 | PF29 | PF30 |
|---|---|---|---|---|---|---|
| Dried Fermented Supernatant[1] | 9-12% | 9-12% | 9-12% | 9-12% | 9-12% | 9-12% |
| Dried Biosurfactant[2] | 6-9% | 7-10% | 8-11% | 10-13% | 11-14% | 12-15% |
| Dried Biosurfactant[3] | 79.5-84.5% | 76.5-83.5% | 75.5-82.5% | 73.5-80.5% | 72.5-79.5% | 71.5-78.5% |
| Dried Citric Acid | 0.5-1.5% | 0.5-1.5% | 0.5-1.5% | 0.5-1.5% | 0.5-1.5% | 0.5-1.5% |

[1] a dried yeast supernatant (TASTONE ® 154).
[2] a dried biosurfactant comprising saponins extracted from *Quillaja saponaria* (Quillaja Dry 100).
[3] a dried biosurfactant comprising saponins extracted from *Yucca schidigera* (Yucca SD Powder).

TABLE 12

Dry Powdered Composition Formulations

| Component | PF31 | PF32 | PF33 | PF34 | PF35 | PF36 |
|---|---|---|---|---|---|---|
| Dried Fermented Supernatant[1] | 10-13% | 10-13% | 10-13% | 10-13% | 10-13% | 10-13% |
| Dried Biosurfactant[2] | 6-9% | 7-10% | 8-11% | 9-12% | 11-14% | 12-15% |
| Dried Biosurfactant[3] | 76.5-83.5% | 75.5-82.5% | 74.5-81.5% | 73.5-80.5% | 71.5-78.5% | 70.5-77.5% |
| Dried Citric Acid | 0.5-1.5% | 0.5-1.5% | 0.5-1.5% | 0.5-1.5% | 0.5-1.5% | 0.5-1.5% |

[1] a dried yeast supernatant (TASTONE ® 154).
[2] a dried biosurfactant comprising saponins extracted from *Quillaja saponaria* (Quillaja Dry 100).
[3] a dried biosurfactant comprising saponins extracted from *Yucca schidigera* (Yucca SD Powder).

TABLE 13

Dry Powdered Composition Formulations

| Component | PF37 | PF38 | PF39 | PF40 | PF41 | PF42 |
|---|---|---|---|---|---|---|
| Dried Fermented Supernatant[1] | 11-14% | 11-14% | 11-14% | 11-14% | 11-14% | 11-14% |
| Dried Biosurfactant[2] | 6-9% | 7-10% | 8-11% | 9-12% | 10-13% | 12-15% |
| Dried Biosurfactant[3] | 75.5-82.5% | 74.5-81.5% | 73.5-80.5% | 72.5-79.5% | 71.5-78.5% | 69.5-76.5% |
| Dried Citric Acid | 0.5-1.5% | 0.5-1.5% | 0.5-1.5% | 0.5-1.5% | 0.5-1.5% | 0.5-1.5% |

[1] a dried yeast supernatant (TASTONE ® 154).
[2] a dried biosurfactant comprising saponins extracted from *Quillaja saponaria* (Quillaja Dry 100).
[3] a dried biosurfactant comprising saponins extracted from *Yucca schidigera* (Yucca SD Powder).

TABLE 14

Dry Powdered Composition Formulations

| Component | PF43 | PF44 | PF45 | PF46 | PF47 | PF48 |
|---|---|---|---|---|---|---|
| Dried Fermented Supernatant[1] | 12-15% | 12-15% | 12-15% | 12-15% | 12-15% | 12-15% |
| Dried Biosurfactant[2] | 6-9% | 7-10% | 8-11% | 9-12% | 10-13% | 11-14% |
| Dried Biosurfactant[3] | 74.5-81.5% | 73.5-80.5% | 72.5-79.5% | 71.5-78.5% | 70.5-77.5% | 69.5-76.5% |
| Dried Citric Acid | 0.5-1.5% | 0.5-1.5% | 0.5-1.5% | 0.5-1.5% | 0.5-1.5% | 0.5-1.5% |

[1] a dried yeast supernatant (TASTONE ® 154).
[2] a dried biosurfactant comprising saponins extracted from *Quillaja saponaria* (Quillaja Dry 100).
[3] a dried biosurfactant comprising saponins extracted from *Yucca schidigera* (Yucca SD Powder).

TABLE 15

Dry Powdered Composition Formulations

| Component | PF49 | PF50 | PF51 | PF52 | PF53 | PF54 |
|---|---|---|---|---|---|---|
| Dried Fermented Supernatant[1] | 12-15% | 8-11% | 8-11% | 8-11% | 8-11% | 8-11% |
| Dried Biosurfactant[2] | 12-15% | 13-16% | 14-17% | 15-18% | 16-19% | 17-20% |
| Dried Biosurfactant[3] | 68.5-75.5% | 71.5-78.5% | 70.5-77.5% | 69.5-76.5% | 68.5-75.5% | 67.5-74.5% |
| Dried Citric Acid | 0.5-1.5% | 0.5-1.5% | 0.5-1.5% | 0.5-1.5% | 0.5-1.5% | 0.5-1.5% |

[1] a dried yeast supernatant (TASTONE ® 154).
[2] a dried biosurfactant comprising saponins extracted from *Quillaja saponaria* (Quillaja Dry 100).
[3] a dried biosurfactant comprising saponins extracted from *Yucca schidigera* (Yucca SD Powder).

Example 6

Preparation of Dry Powdered Composition

This example shows exemplary formulations of dry powdered compositions disclosed herein.

To manufacture an exemplary batch size of 1000 kg of a dry powdered composition, a powder blender such as a rotor stator or rotary drum mixer is pre-treated by spraying internal surfaces with a 1% bleach solution, incubating for 10 minutes and then wiping surfaces dry. Next, 60 kg to 150 kg of a dried treated fermented microbial supernatant (final concentration 6% to 15%) and 5 kg to 15 kg of Citric Acid (final concentration 0.5% to 1.5%) were added to the powder blender (see Tables 16-17) and the components blended to achieve a uniform color and appearance of the mixture. To this mixture was added 835 kg to 935 kg of a dried biosurfactant comprising saponins extracted from *Yucca schidigera* (final concentration 83.5% to 93.5%)(see Tables 16-17), and blending continued until a uniform color and appearance of the mixture was achieved. Dry powdered compositions produced according to this process were found to be nonirritating to skin tissue, nontoxic and could be stored in a cool location over periods of months without any discernible loss in effectiveness or deterioration.

As a specific example of the above, formulation PF57 was prepared by adding 92.0 kg of TASTONE® 154 (a dried treated fermented microbial supernatant) (final concentration 9.2%), and 10.0 kg of Citric Acid (final concentration 1%) were added to the powder blender and the components blended to achieve a uniform color and appearance of the mixture. To this mixture was added 907.0 kg of *Yucca* SD Powder (a dried biosurfactant comprising saponins extracted from *Yucca schidigera*) (final concentration 90.7%), and blending continued until a uniform color and appearance of the mixture was achieved. Dry powdered compositions of formulation PF57 produced according to this process were found to be nonirritating to skin tissue, nontoxic and could be stored in a cool location over periods of months without any discernible loss in effectiveness or deterioration.

Similar procedures are used to manufacture a liquid composition using any of the other formulations of a dry powdered composition described in Tables 7-17. In addition, the amount of dry powdered composition added to 1 L of water can also be varied. For example, 5 g to 500 g of a dry powdered composition can be added to 1 L of water to produce a 0.5% to 50% solution of a liquid composition using a dry powdered composition.

Optionally, 2% to 8% final concentration of an anionic biosurfactant can be incorporated into a liquid composition of this example. For example, STEPONOL® AM 30-KE, an ammonium lauryl sulfate, STEPONOL® EHS, a sodium 2-ethyl hexyl sulfate, or a combination thereof can be added to the liquid composition.

Optionally, 0.5% to 3% final concentration of one or more preservatives can be incorporated into a liquid composition of Tables 1-5 prior to adjusting the volume to 4,500 L with additional water. For example, about 1% by weight sodium benzoate, about 0.01% by weight imidazolidinyl urea, about 0.15% by weight diazolidinyl urea, about 0.25% by weight calcium chloride, or about 0.5% sodium hydroxymethylglycinate (Nuosept 44). In this case, the preservatives are added to the liquid mixture and the temperature of the mixture is then slowly raised to about 40° C. for about one hour with continuous agitation to ensure that all the components of the mixture are dissolved. The mixture is then cooled to from about 20° C. to about 25° C. and the pH of the resulting liquid composition was adjusted using any suitable acid, such as, e.g., phosphoric acid. The pH adjusted liquid composition was then filter sterilized to remove any microbial contamination and packaged for distribution. Liquid compositions produced according to this process were found to be nonirritating to skin tissue, nontoxic and could be stored in a cool location over periods of months without any discernible loss in effectiveness or deterioration.

TABLE 16

Dry Powdered Composition Formulations

| Component | PF55 | PF56 | PF57 | PF58 | PF59 | PF60 |
| --- | --- | --- | --- | --- | --- | --- |
| Dried Fermented Supernatant[1] | 6-9% | 7-10% | 8-11% | 9-12% | 10-13% | 11-14% |
| Dried Biosurfactant[3] | 89.5-93.5% | 88.5-92.5% | 87.5-91.5% | 86.5-90.5% | 85.5-89.5% | 84.5-88.5% |
| Dried Citric Acid | 0.5-1.5% | 0.5-1.5% | 0.5-1.5% | 0.5-1.5% | 0.5-1.5% | 0.5-1.5% |

[1] a dried yeast supernatant (TASTONE ® 154).
[2] a dried biosurfactant comprising saponins extracted from *Quillaja saponaria* (Quillaja Dry 100).
[3] a dried biosurfactant comprising saponins extracted from *Yucca schidigera* (Yucca SD Powder).

TABLE 17

Dry Powdered Composition Formulations

| Component | PF61 |
| --- | --- |
| Dried Fermented Supernatant[1] | 12-15% |
| Dried Biosurfactant[2] | 83.5-87.5% |
| Dried Citric Acid | 0.5-1.5% |

[1] a dried yeast supernatant (TASTONE ® 154).
[2] a dried biosurfactant comprising saponins extracted from *Yucca schidigera* (Yucca SD Powder).

Example 7

Preparation of Liquid Composition

This example shows exemplary procedures to make a liquid composition disclosed herein using a dry powdered composition disclosed herein.

To produce 1 L of an exemplary liquid composition disclosed herein, 30 g of an exemplary dry powdered composition covered under formulation PF3 as described in Example 5 or formulation PF57 as described in Example 6 is added to 1 L of water and mixed until the dry powdered composition is dissolved completely. This makes a 3% solution of a liquid composition using a dry powdered composition. The pH of the liquid composition can be checked and the pH adjusted to 6.5 to 8.0 using any suitable acid, such as, e.g., phosphoric acid.

Example 8

Preparation of a Foam Composition

To prepare a foam composition, a liquid composition is prepared, for example as described in Examples 4 or 7, except that suitable foaming agents like the ones disclosed herein, stabilizing agents, like the ones disclosed herein, or both are added to the liquid composition at a final concentration of 1% to 6% and mixed until completely incorporated.

Example 9

Controlling Fire Using a Liquid Composition

This example shows exemplary use of a liquid composition disclosed herein in controlling a fire using a method disclosed herein.

A building has a wet chemical fire suppression system installed on its premises. A liquid composition disclosed herein, including the one described in Examples 4 and 7, is diluted with water or similar solvent to a final concentration of about 1% to about 5% and is filled into the tank reservoirs of the wet chemical fire suppression system, with or without known wet chemical fire suppression agents, like aqueous potassium carbonate, and pressurized. The tank includes a high-pressured nitrogen cartridge that when activated, will discharge and open the valve on the pressurized tank with the liquid composition, releasing the composition into the piping and out of the nozzles of the suppression system to suppress the fire. Upon an occurrence of a fire, heat sensors of the wet chemical fire suppression system will detect the fire. This detection will activate the system and a liquid composition disclosed herein will be sprayed or otherwise discharged into the area where the fire is located, thereby suppressing or otherwise extinguishing the fire.

An individual has a portable fire extinguisher on his premises. The fire extinguisher contains a liquid composition disclosed herein, including the ones described in Examples 4 and 7, diluted with water or similar solvent to a final concentration of about 1% to about 5% within its reservoir. The fire extinguisher includes a high-pressured gas canister of carbon dioxide in its interior operably linked to the reservoir. When the handle of the fire extinguisher is compressed, it opens the high-pressure gas canister expelling the carbon dioxide into the reservoir which forces the liquid composition from the reservoir through a siphon tube and out the nozzle. When the individual requires the use of the portable fire extinguisher to control a fire, he depresses the handle and sprays the liquid composition over the fire, extinguishing it.

An individual has a liquid fire suppression pump device comprising a reservoir for holding a liquid composition disclosed herein and fitted with the level gauge to monitor the composition levels, a pump which pumps the liquid composition from reservoir to a water line, and a proportioner to control the amount of liquid composition injected into the water line. A liquid composition disclosed herein, including the ones described in Examples 4 and 7, is filled into the reservoir of the liquid fire suppression pump device, with or without known foam fire suppression agents. In operation, the liquid fire suppression pump device is connected to a water source like a fire hydrant, a plumbed water supply or a portable or installed water tank fitted with a pump. The pump then takes suction from the reservoir and injects the liquid composition into the water line, with the amount of liquid composition injected into the water line controlled by the proportioner, a typical dilution range is 1% to 5% of the starting liquid composition contained in the reservoir. The liquid solution is carried through a hose, in a portable system, or a hard-piped network, in an installed system, to the desired location. A nozzle is provided at end of the pipe or pipe network. When the individual requires the use of the liquid fire suppression device to control a fire, he operated the device and sprays the liquid solution using the liquid composition over the fire, extinguishing it.

A liquid composition disclosed herein, including the ones described in Examples 4 and 7, can also be used in an aerial fire suppression system such as the ones described in U.S. Pat. Nos. 6,474,564, 7,748,662, and 10,406,390 and US Patent Publication Nos. 2014/0069666 and 2014/0374537, the content of each of which are hereby incorporated by reference in its entirety. In one example, an aircraft, such as a helicopter, airship, drone or airplane, comprises a first tank holding water, a second tank holding liquid composition disclosed herein, nozzles, and piping in fluid communication with both the first and second tanks and the nozzles. As the aircraft files over a fire, water is pumped out of the first tank and through the nozzles, creating a Venturi effect which will draw the liquid composition from the second tank and into the piping where it mixes with the water in the nozzle, which is then directed onto the fire below.

Likewise, further examples include land-based vehicles, such as firefighting engines and trucks where such an arrangement can be provided to mix a liquid composition from a reservoir and into water to be applied and directed onto a fire and/or areas/object that are near a fire or predicted to be in the path of a fire.

Example 10

Controlling Fire Using a Foam Composition

This example shows exemplary use of a foam composition disclosed herein in controlling a fire using a method disclosed herein.

A building has a foam fire suppression system installed on its premises. A foam composition disclosed herein, made by diluting a liquid composition disclosed herein, including the ones described in Examples 4 and 7, with water or similar solvent to a final concentration of about 1% to about 5% is filled into the tank reservoirs of the foam fire suppression system, with or without known foam fire suppression agents. Optionally suitable foaming agents like the ones disclosed herein, stabilizing agents, like the ones disclosed herein, or both may be incorporated at a final concentration of 1% to 6%, e.g., the foam compositions described in Example 8. The tank includes a high-pressured carbon dioxide or nitrogen cartridge that when activated, will discharge and open the valve on the pressurized tank with the foam composition, releasing the composition into the piping and out of the nozzles of the suppression system to suppress the fire. Upon an occurrence of a fire, heat sensors of the foam fire suppression system will detect the fire. This detection will activate the system and a foam composition disclosed herein will be sprayed or otherwise discharged into the area where the fire is located, thereby suppressing or otherwise extinguishing the fire.

An individual has a portable fire extinguisher on his premises. The fire extinguisher contains a foam composition disclosed herein, made by diluting a liquid composition disclosed herein, including the ones described in Examples 4 and 7, with water or similar solvent to a final concentration of about 1% to about 5%. Optionally suitable foaming agents like the ones disclosed herein, stabilizing agents, like the ones disclosed herein, or both may be incorporated at a final concentration of 1% to 6%, e.g., the foam compositions described in Example 8. The fire extinguisher includes a high-pressured gas canister of carbon dioxide in its interior operably linked to the reservoir. When the handle of the fire extinguisher is compressed, it opens the high-pressure gas canister expelling the carbon dioxide into the reservoir which forces the foam composition from the reservoir through a siphon tube and out the nozzle. As the pumped foam solution passes through the monitor or nozzle, it creates a low-pressure zone that causes air to rush inside through holes of monitor or nozzle to create foam. When the individual requires the use of the portable fire extinguisher to control a fire, he depresses the handle and sprays the foam composition over the fire, extinguishing it.

An individual has a foam fire suppression device comprising a foam tank for holding a foam composition disclosed herein and fitted with the level gauge to monitor the composition levels, a centrifugal foam pump which pumps the foam composition from foam tank to the water line, and a proportioner to control the amount of foam composition mixing with water to form a foam solution. A foam composition disclosed herein, made by diluting a liquid composition disclosed herein, including the ones described in Examples 4 and 7, with water or similar solvent to a final concentration of about 1% to about 5%, is filled into the foam tank of the foam fire suppression device, with or without known foam fire suppression agents. Optionally suitable foaming agents like the ones disclosed herein, stabilizing agents, like the ones disclosed herein, or both may be incorporated at a final concentration of 1% to 6%, e.g., the foam compositions described in Example 8. In operation, the foam fire suppression device is connected to a water source like a fire hydrant, a plumbed water supply or a water tank fitted with a pump. The foam pump then takes suction from the foam tank and injects the foam composition into the water line, with the amount of foam composition injected into the water line controlled by the proportioner. The foam solution is carried through a hose, in a portable system, or a hard-piped network, in an installed system, to the desired location. A foam monitor or nozzle is provided at end of the pipe or pipe network. As the pumped foam solution passes through the monitor or nozzle, it creates a low-pressure zone that causes air to rush inside through holes of monitor or nozzle to create foam. When the individual requires the use of the foam fire suppression device to control a fire, he operated the device and sprays the foam formed using the foam composition over the fire, extinguishing it.

Example 11

Controlling Fire Using a Dry Powdered Composition

This example shows exemplary use of a dry powdered composition disclosed herein in controlling a fire using a method disclosed herein.

A building has a dry chemical fire suppression system installed on its premises. A dry powdered composition disclosed herein, including the ones described in Examples 5 and 6, is filled in the tank reservoirs of the dry chemical fire suppression system, with or without known dry chemical powder fire suppression agents like monoammonium phosphate, sodium bicarbonate, or potassium bicarbonate, and pressurized. The tank includes a high-pressured nitrogen cartridge that when activated, will discharge and open the valve on the pressurized tank with the dry powdered composition, releasing the composition into the piping and out of the nozzles of the suppression system to suppress the fire. Upon an occurrence of a fire, heat sensors of the dry chemical fire suppression system will detect the fire. This detection will activate the system and a dry powdered composition disclosed herein will be sprayed or otherwise discharged into the area where the fire is located, thereby suppressing or otherwise extinguishing the fire.

An individual has a portable fire extinguisher on his premises. The fire extinguisher contains a dry powdered composition disclosed herein, including the ones described in Examples 5 and 6, within its reservoir. The fire extinguisher includes a high-pressured gas canister of carbon dioxide in its interior operably linked to the reservoir. When the handle of the fire extinguisher is compressed, it opens the high-pressure gas canister expelling the carbon dioxide into the reservoir which forces the dry powdered composition from the reservoir through a siphon tube and out the nozzle. When the individual requires the use of the portable fire extinguisher to control a fire, he depresses the handle and sprays the dry powdered composition over the fire, extinguishing it.

A dry powdered composition disclosed herein, including the ones described in Examples 5 and 6, can also be used in an aerial fire suppression system such as the ones described in U.S. Pat. Nos. 6,474,564, 7,748,662, and 10,406,390 and US Patent Publication Nos. 2014/0069666 and 2014/0374537, the content of each of which are hereby incorporated by reference in its entirety.

Example 12

Controlling Fire Using a Fire Extinguishing Composition

This example shows exemplary efficacy of a fire extinguishing composition disclosed herein in extinguishing a fire fueled by tires as the combustible material employing a method disclosed herein.

In an area devoid of all vegetative growth, a pit having dimensions of approximately 3.5 m in width×2.5 m in length×1.5 m in depth was dug in the ground. Three automobile tires we placed in the center of the pit and dosed in gasoline. A firefighter ignited the tires using a torch and the combustible materials were allowed to burn for 1 minute. The entire pit was engulfed in flames with peak heights reaching about 5 m above ground level and extensive thick black billowing smoke emanating from the fire. At this point the firefighter began hosing the fire down with a liquid solution comprising a fire extinguishing composition disclosed herein, such as the ones described in Examples 4 and 7, by spraying the solution over the entire pit area using a broad nozzle. The fire was extinguished in about 20 to 25 seconds. The firefighter than tried to reignite the tires using the torch, but was unable to do so, indicating that a fire extinguishing composition disclosed herein was not only significantly effective in extinguishing the initial fire, but also prevent reignition of the combustible material coated with a fire extinguishing composition disclosed herein.

The above experiment was repeated using different combustible materials, including wood and oil with similar fire extinguishing effects. With respect to the experiments conducted with oil, a fire extinguishing composition disclosed herein also resulted in a significant remediation of hydrocarbons.

These experiments demonstrate that a fire extinguishing composition disclosed herein is extremely effective in extinguishes a fire fueled by a wide variety of combustible materials. In addition, as non-toxic compositions, a fire extinguishing composition disclosed herein has a significant technical advantage in that it does not pollute the environment, expose humans and other living beings to toxic substances, and further degrades residual combustible materials remaining after the fire is extinguished.

In closing, foregoing descriptions of embodiments of the present invention have been presented for the purposes of illustration and description. It is to be understood that, although aspects of the present invention are highlighted by referring to specific embodiments, one skilled in the art will readily appreciate that these described embodiments are only illustrative of the principles comprising the present invention. As such, the specific embodiments are not intended to be exhaustive or to limit the invention to the precise forms disclosed. Therefore, it should be understood that embodiments of the disclosed subject matter are in no way limited to a particular element, compound, composition, component, article, apparatus, methodology, use, protocol, step, and/or limitation described herein, unless expressly stated as such.

In addition, groupings of alternative embodiments, elements, steps and/or limitations of the present invention are not to be construed as limitations. Each such grouping may be referred to and claimed individually or in any combination with other groupings disclosed herein. It is anticipated that one or more alternative embodiments, elements, steps and/or limitations of a grouping may be included in, or deleted from, the grouping for reasons of convenience and/or patentability. When any such inclusion or deletion occurs, the specification is deemed to contain the grouping as modified, thus fulfilling the written description of all Markush groups used in the appended claims.

Furthermore, those of ordinary skill in the art will recognize that certain changes, modifications, permutations, alterations, additions, subtractions and sub-combinations thereof can be made in accordance with the teachings herein without departing from the spirit of the present invention. Furthermore, it is intended that the following appended claims and claims hereafter introduced are interpreted to include all such changes, modifications, permutations, alterations, additions, subtractions and sub-combinations as are within their true spirit and scope. Accordingly, the scope of the present invention is not to be limited to that precisely as shown and described by this specification.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

The words, language, and terminology used in this specification is for the purpose of describing particular embodiments, elements, steps and/or limitations only and is not intended to limit the scope of the present invention, which is defined solely by the claims. In addition, such words, language, and terminology are to be understood not only in the sense of their commonly defined meanings, but to include by special definition in this specification structure, material or acts beyond the scope of the commonly defined meanings. Thus, if an element, step or limitation can be understood in the context of this specification as including more than one meaning, then its use in a claim must be understood as being generic to all possible meanings supported by the specification and by the word itself.

The definitions and meanings of the elements, steps or limitations recited in a claim set forth below are, therefore, defined in this specification to include not only the combination of elements, steps or limitations which are literally set forth, but all equivalent structure, material or acts for performing substantially the same function in substantially the same way to obtain substantially the same result. In this sense it is therefore contemplated that an equivalent substitution of two or more elements, steps or limitations may be made for any one of the elements, steps or limitations in a claim set forth below or that a single element, step or limitation may be substituted for two or more elements, steps or limitations in such a claim. Although elements, steps or limitations may be described above as acting in certain combinations and even initially claimed as such, it is to be expressly understood that one or more elements, steps or limitations from a claimed combination can in some cases be excised from the combination and that the claimed combination may be directed to a sub-combination or variation of a sub-combination. As such, notwithstanding the fact that the elements, steps and/or limitations of a claim are set forth below in a certain combination, it must be expressly understood that the invention includes other combinations of fewer, more or different elements, steps and/or limitations, which are disclosed in above even when not initially claimed in such combinations. Furthermore, insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. Accordingly, the claims are thus to be understood to include what is specifically illustrated and described above, what is conceptually equivalent, what can be obviously substituted and also what essentially incorporates the essential idea of the invention.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as, e.g., "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as, e.g., "comprise" and "comprises", and equivalent open-ended transitional phrases thereof like "including," "containing" and "having", encompass all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as, e.g., "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim, whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such, the embodiments described herein or so claimed with the phrase "comprising" expressly and unambiguously provide description, enablement, and support for the phrases "consisting essentially of" and "consisting of."

Lastly, all patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents are based on the information available to the applicant and do not constitute any admission as to the correctness of the dates or contents of these documents.

The invention claimed is:

1. A method for controlling a fire, the method comprising: applying an effective amount of a composition to a fire, wherein the composition comprises a treated, fermented microbial supernatant including bio-nutrients, minerals, and amino acids and one or more nonionic surfactants, wherein the treated, fermented microbial supernatant lacks any active enzymes, activatable pro-enzymes, or any enzymatic activity.

2. The method according to claim 1, wherein the treated, fermented microbial supernatant is from a fermented yeast supernatant, a fermented bacterial supernatant, a fermented mold supernatant, or any combination thereof.

3. The method according to claim 2, wherein the fermented yeast supernatant is produced from a culture containing yeast belonging to the genus *Brettanomyces, Candida, Cyberlindnera, Cystofilobasidium, Debaryomyces, Dekkera, Fusarium, Geotrichum, Issatchenkia, Kazachstania, Kloeckera, Kluyveromyces, Lecanicillium, Mucor, Neurospora, Penicillium, Pichia, Rhizopus, Rhodosporidium, Rhodotorula, Saccharomyces, Schizosaccharomyces, Thrichosporon, Torulaspora, Torulopsis, Verticillium, Yarrowia, Zygosaccharomyces*, or *Zygotorulaspora*.

4. The method according to claim 1, wherein the one or more nonionic surfactants include one or more polyether nonionic surfactants, one or more polyhydroxyl nonionic surfactants, and/or one or more nonionic biosurfactants.

5. The method according to claim 1, wherein the one or more nonionic surfactants include one or more alcohol ethoxylate nonionic surfactants, one or more alkylphenol ethoxylate nonionic surfactant, alkene amide nonionic surfactant, or a combination thereof.

6. The method according to claim 1, wherein the composition further comprises one or more anionic surfactants.

7. The method according to claim 6, wherein the one or more anionic surfactants include an alkane sulfonate anionic surfactant.

8. The method according to claim 1, wherein the composition is formulated as a liquid composition, a dry powdered composition, a paste composition or a colloidal composition.

9. The method according to claim 8, wherein the colloidal composition is a foam composition.

10. The method according to claim 1, wherein the composition is a liquid composition comprising 15% to 50% by weight of a treated, fermented microbial supernatant and 3% to 15% by weight of one or more nonionic surfactants.

11. The method according to claim 1, wherein the composition is a dry powdered composition comprising 6% to 15% by weight of a dried treated, fermented microbial supernatant, and the one or more nonionic surfactants comprise 6% to 20% by weight of a first dried nonionic biosurfactant, and 67.5% to 87.5% by weight of a second dried nonionic biosurfactant.

12. The method according to claim 1, wherein the composition is a foam composition comprising 15% to 50% by weight of a treated, fermented microbial supernatant, 3% to 15% by weight of one or more nonionic surfactants.

13. The method according to claim 12, wherein the foam composition further comprises 1% to 6% by weight of one or more foaming agents, 2% to 10% by weight of one or more stabilizing agents, or both.

14. The method according to claim 1, wherein the composition further comprises 1% to 3% by weight of one or more preservatives.

15. The method according to claim 1, wherein the fire uses combustible solid substances as a fuel source, uses combustible liquid, liquefiable substances or gases as a fuel source, uses combustible metals and metal alloys as a fuel source, or uses combustible cooking liquids as a fuel source.

16. The method according to claim 1, wherein the fire involve electrical components and/or energized equipment.

17. The method according to claim 1, wherein the composition is applied to one or more areas where control of a fire is desired.

18. The method according to claim 17, wherein the one or more areas is a man-made structure or apparatus, or a natural structure or location.

* * * * *